(12) United States Patent
Kumar et al.

(10) Patent No.: US 11,164,082 B2
(45) Date of Patent: *Nov. 2, 2021

(54) METHODS FOR USING ARTIFICIAL NEURAL NETWORK ANALYSIS ON FLOW CYTOMETRY DATA FOR CANCER DIAGNOSIS

(71) Applicant: Anixa Diagnostics Corporation, San Jose, CA (US)

(72) Inventors: Amit Kumar, San Jose, CA (US); John Roop, Ben Lomond, CA (US); Anthony J. Campisi, Setauket, NY (US); George Dominguez, Voorhees, NJ (US)

(73) Assignee: ANIXA DIAGNOSTICS CORPORATION, San Jose, CA (US)

( * ) Notice: Subject to any disclaimer, the term of this patent is extended or adjusted under 35 U.S.C. 154(b) by 375 days.

This patent is subject to a terminal disclaimer.

(21) Appl. No.: 16/433,912

(22) Filed: Jun. 6, 2019

(65) Prior Publication Data

US 2019/0303760 A1 Oct. 3, 2019

Related U.S. Application Data

(63) Continuation of application No. 15/912,511, filed on Mar. 5, 2018, now Pat. No. 10,360,499, which is a (Continued)

(51) Int. Cl.
*G06N 3/08* (2006.01)
*G06N 3/12* (2006.01)
(Continued)

(52) U.S. Cl.
CPC ............. *G06N 3/08* (2013.01); *G06N 3/0454* (2013.01); *G06N 3/126* (2013.01); *G16B 40/00* (2019.02)

(58) Field of Classification Search
CPC ........ G06N 3/0454; G06N 3/08; G06N 3/126; G16B 40/00
See application file for complete search history.

(56) References Cited

U.S. PATENT DOCUMENTS 5,117,466 A * 5/1992 Buican ............... G01N 15/1434
250/458.1
5,753,014 A 5/1998 Van Rijn
(Continued)

FOREIGN PATENT DOCUMENTS

CN 103984958 A 8/2014
WO WO-2011002649 A1 1/2011
(Continued)

OTHER PUBLICATIONS

Jiang et al. Comparison study of distinguishing cancerous and normal prostate epithelial cells by confocal and polarization diffraction imaging. J Biomed Opt 21(7):71102 (2016).
(Continued)

*Primary Examiner* — Li B. Zhen
*Assistant Examiner* — Peter D Coughlan
(74) *Attorney, Agent, or Firm* — Wilson Sonsini Goodrich & Rosati

(57) ABSTRACT

The present disclosure provides methods for applying artificial neural networks to flow cytometry data generated from biological samples to diagnose and characterize cancer in a subject. The disclosure also provides methods of training, testing, and validating artificial neural networks.

49 Claims, 19 Drawing Sheets
(5 of 19 Drawing Sheet(s) Filed in Color)

Related U.S. Application Data continuation-in-part of application No. 15/445,913, filed on Feb. 28, 2017, now Pat. No. 9,934,364.

(51) Int. Cl.
  *G06N 3/04* (2006.01)
  *G16B 40/00* (2019.01)

(56) References Cited

U.S. PATENT DOCUMENTS

| | | | |
|---|---|---|---|
| 5,809,490 | A | 9/1998 | Guiver et al. |
| 5,837,115 | A | 11/1998 | Austin et al. |
| 6,251,343 | B1 | 6/2001 | Dubrow et al. |
| 6,598,750 | B2 | 7/2003 | Tai et al. |
| 8,341,100 | B2 | 12/2012 | Miller et al. |
| 8,921,102 | B2 | 12/2014 | Fuchs et al. |
| 8,980,568 | B2 | 3/2015 | Lin et al. |
| 9,182,387 | B2 | 11/2015 | Goldkorn et al. |
| 9,739,783 | B1 | 8/2017 | Kumar et al. |
| 9,934,364 | B1 | 4/2018 | Kumar et al. |
| 10,360,499 | B2 | 7/2019 | Kumar et al. |
| 2003/0184730 | A1* | 10/2003 | Price .................... G06T 5/50 356/39 |
| 2004/0199482 | A1 | 10/2004 | Wilson |
| 2009/0181384 | A1 | 7/2009 | Nekarda et al. |
| 2009/0204557 | A1 | 8/2009 | Zhang |
| 2010/0105074 | A1 | 4/2010 | Covey et al. |
| 2011/0236903 | A1 | 9/2011 | McClelland et al. |
| 2012/0082362 | A1 | 4/2012 | Diem et al. |
| 2012/0183946 | A1 | 7/2012 | Tang et al. |
| 2012/0276555 | A1 | 11/2012 | Kuhn et al. |
| 2013/0071876 | A1 | 3/2013 | Hao et al. |
| 2013/0173618 | A1 | 7/2013 | Banville et al. |
| 2013/0255361 | A1 | 10/2013 | Juncker et al. |
| 2013/0266959 | A1 | 10/2013 | Kaiser et al. |
| 2013/0309662 | A1 | 11/2013 | Park |
| 2014/0030799 | A1 | 1/2014 | Yu et al. |
| 2014/0178890 | A1 | 6/2014 | Kanbara et al. |
| 2015/0010924 | A1* | 1/2015 | Duda ............... G01N 33/56966 435/7.24 |
| 2015/0213302 | A1 | 7/2015 | Madabhushi et al. |
| 2015/0356238 | A1 | 12/2015 | Sen et al. |
| 2016/0123964 | A1 | 5/2016 | Tumeh et al. |
| 2016/0136552 | A1 | 5/2016 | Nakanishi et al. |
| 2016/0169786 | A1 | 6/2016 | Albitar et al. |
| 2016/0314281 | A1 | 10/2016 | Apte et al. |
| 2016/0334401 | A1 | 11/2016 | Lockton et al. |
| 2017/0032017 | A1 | 2/2017 | Morinaga et al. |
| 2017/0044264 | A1 | 2/2017 | Fricke et al. |
| 2017/0044265 | A1 | 2/2017 | Ahmadi et al. |
| 2018/0247715 | A1 | 8/2018 | Kumar et al. |

FOREIGN PATENT DOCUMENTS

| | | | |
|---|---|---|---|
| WO | WO-2011139445 | A1 | 11/2011 |
| WO | WO-2013158045 | A1 | 10/2013 |
| WO | WO-2013181532 | A1 | 12/2013 |
| WO | WO-2015112932 | A1 | 7/2015 |
| WO | WO-2015177268 | A1 | 11/2015 |
| WO | WO-2018160751 | A1 | 9/2018 |
| WO | WO-2019173233 | A1 | 9/2019 |

OTHER PUBLICATIONS

U.S. Appl. No. 15/881,558 Office Action dated Oct. 26, 2020.
Adams et al. Circulating Cancer-Associated Macrophage-Like Cells Differentiate Malignant Breast Cancer and Benign Breast Condition. Cancer Epidemiol Biomarkers Prev 25:1037-1042 (2016).
Adams et al. Circulating giant macrophages as a potential biomarker of solid tumors. PNAS USA 111:3514-3519 (2014).
Amato et al. Artificial neural networks in medical diagnosis. J. Appl. Biomed. 11:47-58 (2013).
Arnold. Non-invasive glucose monitoring. Curr Opin Biotech. 7:46-49 (1996).
Atkov et al. Coronary heart disease diagnosis by artificial neural networks including genetic polymorphisms and clinical parameters. J Cardiol. 59:190-194 (2012).
Banjar et al. Intelligent Techniques Using Molecular Data Analysis in Leukaemia: An Opportunity for Personalized Medicine Support System. Biomed Res Int 2017:3587309 (2017).
Barbosa et al. Automatic small bowel tumor diagnosis by using multi-scale wavelet-based analysis in wireless capsule endoscopy images. Biomed Eng Online. 11:3 (2012).
Barnett et al. CD4 immunophenotyping in HIV infection. Nat Rev Microbiol 6(11 Suppl.):S7-S15 (2008).
Barwad et al. Artificial neural network in diagnosis of metastatic carcinoma in effusion cytology. Cytometry B Clyn Cytom. 82:107-111 (2012).
Brock et al. Liquid biopsy for cancer screening, patient stratification and monitoring. Transl Cancer Res 4(3):280-290 (2015).
Buyssens et al. Chapter 27. Multiscale Convolutional Neural Networks for Vision-Based Classification of Cells. Computer Vision—ACCV 2012, Part II, LNCS 7725, pp. 342-353 (2013).
Chen et al. Single-Cell Analysis of Circulating Tumor Cells. Cancer Biol Med 12:184-192 (2015).
Ciresan et al. Chapter 51. Mitosis Detection in Breast Cancer Histology Images with Deep Neural Networks. MICCAI 2013 8150:411-418 (2013).
Coumans et al. Filter Characteristics Influencing Circulating Tumor Cell Enrichment from Whole Blood. PLoS One 8(4):e61770 (2013).
De Bruijn et al. Artificial neural network analysis to assess hypernasality in patients treated for oral or oropharyngeal cancer. Logoped Phoniatr Vocol. 36:168-174 (2011).
Dominguez et al. Poster No. 1032. The Coupling of MDSCs with a Computational Analytic Method to Detect Solid Tumors. Keystone: Combinations, Mar. 23-27, 2018 Montreal, Quebec, Canada (1 pg.).
Dominguez et al. Poster No. 24. The Coupling of MDSCs with a Computational Analytic Method to Detect Solid Tumors. ASCO-SITC Clinical Immuno-oncology Symposium Jan. 25-27, 2018 San Francisco, CA. (1 pg.).
Dong et al. Deep Learning for Automatic Cell Detection in Wide-Field Microscopy Zebrafish Images. 2015 IEEE 12th International Symposium on Biomedical Imaging (ISBI) (5 pgs) (Apr. 16-19, 2015).
Faber et al. Activated macrophages containing tumor marker in colon carcinoma: immunohistochemical proof of a concept. Tumor Biol 33(2):435-441 (2012).
Fernandez-Blanco et al. Automatic seizure detection based on star graph topological indices. J Neurosci Methods. 209:410-419 (2012).
Frankel et al. Application of neural networks to flow cytometry data analysis and real-time cell classification. Cytometry 23(4):290-302 (1996).
Harouaka et al. Circulating Tumor Cell Enrichment Based on Physical Properties. Journal of Laboratory Automation 18(6):455-468 (2013).
Ho et al. Disease-free survival after hepatic resection in hepatocellular carcinoma patients: a prediction approach using artificial neural network. PloS One 7:e29179 (2012).
Kraus et al. Classifying and Segmenting Microscopy Images Using Convolutional Multiple Instance Learning. Bioinformatics 32(12):i52-i59 (2016).
Krombach et al. Cell Size of Alveolar Macrophages: An Interspecies Comparison. Environ Health Perspect 105(Supp 5):1261-1263 (1997).
Kumar et al. Abstract No. 667. Immuno-profiling Circulating Blood as a Means to early Detection of Solid Tumors. Poster. ITUS Corporation (2017)Kumar et al. Abstract No. 667. Immuno-profiling Circulating Blood as a Means to early Detection of Solid Tumors. Poster. ITUS Corporation.
Lu et al. A study of the autofluorescence of parylene materials for µTAS applications. Lab Chip 10:1826-1834 (2010).
Lucas et al. Rapid diagnosis of chronic myeloid leukemia by flow cytometric detection of BCR-ABL1 protein. Haematologica 96(7):1077-1078 (2011).
Malon et al. Identifying histological elements with convolutional neural networks. Proceeding CSTST '08 Proceedings of the 5th

(56) References Cited

OTHER PUBLICATIONS international conference on Soft computing as transdisciplinary science and technology. pp. 450-456 (2008).

Mehrotra et al. Elements of artificial neural networks. MIT press (351 pgs) (1997).

Nagrath et al. Isolation of rare circulating tumour cells in cancer patients by microchip technology. Nature 450(7173):1235-1239 (2007).

PCT/US2018/20303 International Search Report and Written Opinion dated Apr. 20, 2018.

PCT/US2019/020588 International Search Report and Written Opinion dated May 17, 2019.

Ranzato et al. Automatic Recognition of Biological Particles in Microscopic Images. Pattern Recognition Letters 28(1):31-39 (2007).

Recktenwald. Teaching Notes from Multidimensional Flow Cytometric Analysis of Bone Marrow and Peripheral Blood Stem Cells. J Hematother 2:387-394 (1993).

Romaszko. Signal Correlation Prediction Using Convolutional Neural Networks. JMLR: Workshop and Conference Proceedings 46:45-56 (2015).

Sanborn. Detection of fluorescent neuron cell bodies using convolutional neural networks. Stanford University—Final Report. (7 pgs.) (2015).

Schmid et al. Myeloid cell trafficking and tumor angiogenesis. Cancer Lett 250(1):1-8 (2007).

Shi. Classification of leukemia diseased cells. MATEC Web of Conferences 44:02081 (2016).

Sollier et al. Size-selective collection of circulating tumor cells using Vortex technology. Lab Chip 14(1):63-77 (2014).

Sorokina. Image Classification with Convolutional Neural Networks. Available at https://medium.com/aksusorokina/image-classification-with-convolutional-neural-networks-496815db12a8 (Nov. 19, 2017) (Retrieved on May 4, 2019).

Uguz. A biomedical system based on artificial neural network and principal component analysis for diagnosis of the heart valve diseases. J Med Syst. 36:61-72 (2012).

U.S. Appl. No. 15/209,616 Office Action dated Nov. 7, 2016.

U.S. Appl. No. 15/445,913 Office Action dated Jun. 13, 2017.

U.S. Appl. No. 15/912,511 Office Action dated Dec. 20, 2018.

U.S. Appl. No. 15/912,511 Office Action dated May 30, 2018.

Xie et al. Microscopy Cell Counting with Fully Convolutional Regression Networks. Department of Engineering Science, University of Oxford, UK. (8 pgs.) (no date provided).

Xu et al. A Cancer Detection Platform Which Measures Telomerase Activity from Live Circulating Tumor Cells Captured on a Microfilter. Cancer Res 70(16):6420-6426 (2010).

Zheng et al. 3D microfilter device for viable circulating tumor cell (CTC) enrichment from blood. Biomed Microdevices 13(1):203-213 (2011).

Zheng et al. Membrane microfilter device for selective capture, electrolysis and genomic analysis of human circulating tumor cells. J Chromatogr A 1162(2):154-161 (2007).

* cited by examiner

METHODS FOR USING ARTIFICIAL NEURAL NETWORK ANALYSIS ON FLOW CYTOMETRY DATA FOR CANCER DIAGNOSIS

CROSS REFERENCE

This application is a continuation application of U.S. Patent Application No. 15/912,511, filed Mar. 5, 2018, which is a continuation-in-part of U.S. Patent Application No. 15/445,913, filed Feb. 28, 2017, issued as U.S. Pat. No. 9,934,364, on Apr. 3, 2018, each of which is incorporated herein by reference in its entirety.

BACKGROUND OF THE INVENTION

In the course of a lifetime, cancer will strike about one in three women and one in two men. More than 560,000 die from it each year in the United States alone. Early detection and treatment is currently the leading method to reduce cancer death, especially if the cancer is detected before metastasis. For nearly all types of cancer, the 5-year relative survival rate is substantially lower if the disease is caught at an advanced stage. Moreover, the financial costs of cancer treatment at an advanced stage can be an additional burden. By 2020, the cost of cancer treatment is expected to be $207 billion annually in the United States. Accordingly, early detection of cancer is important for increasing cancer survival rates and reducing the cost of treatment.

However, methods for early detection often lack sensitivity and generate numerous false positives and negatives. False negatives lead to missed opportunities to intervene early, and false positives lead to additional unnecessary testing, which can include biopsies and other painful, stressful and expensive procedures. The overall health burden borne by test subjects who register as false positives can outweigh the benefits to those patients who benefit from early detection of their cancers. This is especially true for screening tests where the incidence of disease is low. In addition, conventional screening tests, such as colonoscopies, are often invasive; hence, individuals are often resistant to undertake them. Thus, there is a need for a cancer diagnostic test that produces an unambiguous result, is low cost and minimally invasive, and has few false negatives and few false positives. Such a test would be useful for recurrence testing, validation or confirmatory testing, and other situations where an initial indication of cancer needs to be verified before an expensive and aggressive follow-up procedure is performed. When considering a confirmatory test, it is well known that up to 95% of biopsies return negative results (meaning the early indication of cancer was not verified by the painful, expensive procedure). Consequently, a simple, non-invasive, inexpensive test that could either confirm the need for a biopsy or eliminate the need for one, would be very valuable to patients and the healthcare system.

Currently, a type of diagnostic called Liquid Biopsy is being investigated as a technique for determining the presence of cancer in a test subject by analysis of a blood sample or other easily obtained bodily fluid. Many different characteristics of the blood sample are being investigated. These include analysis of deoxyribonucleic acid (DNA), ribonucleic acid (RNA), proteins, microRNA, exosomes, and other potential biomarkers of cancer. However, many of these liquid biopsy methodologies rely on expensive analytical techniques such as DNA or RNA sequencing. These tests often require extensive levels of multiplexing that make them expensive, difficult to operate, and also difficult to interpret. Myeloid-Derived Suppressor Cells (MDSCs) are a type of cell known to be highly correlated with the presence of malignant solid tumors, and they are present at low levels in the blood. Studies have shown that MDSCs are concentrated in the tumor environment and function to suppress immune response to the tumor. Their presence in peripheral circulation is believed to be due to spilling of these immature cells from the tumor into the vasculature. Extensive work has shown that shifts in the MDSC population that are correlated with cancer can be detected using Flow Cytometry, an inexpensive, widely used, and reliable method of cellular population analysis. However, conventional methods of flow cytometry data analysis as applied to MDSCs in blood samples are not sufficiently accurate to allow MDSCs to be used as a sole biomarker for a cancer detection screening test for the general public. Flow cytometers can process a sample containing hundreds of thousands of cells, or more, suspended in a fluid medium and provide detailed distinguishing information on each individual cell in the sample. The conventional method of analysis of flow cytometry data relies on a technique called gating. Gating is a method of sequentially applying threshold cutoffs to one- or two-dimensional projections of the multidimensional data set in order to isolate a specific population or populations and count the number of cells in the isolated populations. While this method is suitable for research studies and some diagnostic applications, for cancer detection, this method of analysis can be labor intensive, subjective, and results in a very coarse representation of the flow cytometer output data, often obscuring or ignoring a great deal of information available regarding the relative distributions of all the cell populations and the shape of the distributions of the isolated cell populations. Thus, a flow cytometer analysis method that can be utilized to identify target cells indicative of cancer reliably, economically, and with the required specificity and sensitivity is needed.

SUMMARY OF THE INVENTION

Described herein are methods relating to flow cytometry data analysis that use flow cytometer output data to classify characteristics of cell populations. Described herein are methods relating to flow cytometry that eliminate the need for most manual or automatic gating of cell populations. Described herein are methods relating to flow cytometry data analysis for diagnosing cancer by analyzing target cell populations, such as MDSCs, in concert with other cell populations including myeloid cells and lymphoid cells. A diagnosis of cancer as used hereinafter means a diagnosis of there being a malignant tumor present. Described herein are methods of flow cytometry data analysis that include a computationally efficient representation of cell populations in a multidimensional data space, wherein the axes of the data space are the measurement channels of a flow cytometer or a transformation thereof. The methods may further comprise a neural network analysis that classifies samples based on the learned characteristics of the distributions of target cells in a multidimensional data space. Described herein are methods relating to flow cytometry data analysis that can be performed on an entirety of a target cell distribution and therefore detect distinctions between samples that are undetectable by conventional flow cytometry data gating. Data analysis methods as described herein can be used for malignant tumor detection by detecting cell population and subpopulation distribution differences, including differentiation of MDSC subpopulations present, for example, in peripheral blood samples taken from non-tumor-bearing subjects and subjects having malignant tumors (tumor-bearing subjects). By providing sensitive and specific methods and devices for differentiating various cell types and detecting cell population differences, cancer diagnostic devices and assays can be developed for early cancer detection in subjects or various patients.

In various embodiments, specific cell population detection is based on neural networks used to analyze flow cytometry data. Technologies for analyzing multidimensional flow cytometry data using neural networks disclosed herein include automatic gating and cast a new paradigm for identifying specific cell populations and their distributions with higher accuracy.

In one aspect, provided herein are systems and methods for applying artificial neural networks to a plurality of events of interest in a biological sample from a subject to generate a medical diagnosis and a treatment recommendation of a cancer in the subject, comprising: (a) performing, by a computer, analysis of the biological sample from the subject, the analysis comprising: 1) obtaining measurements of a plurality of event features for each of the plurality of events of interest with a flow cytometer instrument, 2) using four or more flow cytometer measurement channels to define a feature coordinate space, the feature coordinate space comprising four or more axes, each axis corresponding to a different channel of the four or more flow cytometer measurement channels, wherein each of the four or more flow cytometer measurement channels produces measurements of the plurality of event features, and 3) using the measurements of the plurality of event features for the plurality of events of interest to define locations for the plurality of events of interest in the feature coordinate space to form a distribution in the feature coordinate space indicative of an event population of interest; (b) applying, by the computer, an artificial neural network detection structure to the distribution in the feature coordinate space indicative of the event population of interest, the detection structure employing an artificial neural network to correlate the distribution in the feature coordinate space indicative of the event population of interest with a distribution in a reference feature coordinate space indicative of a reference event population; (c) determining, by the computer, whether the biological sample contains cells indicative of the cancer in the subject, thereby diagnosing the cancer in the subject; (d) identifying, by the computer, characteristic cell features of cells indicative of cancer; and (e) automatically generating, by the computer, a report comprising the medical diagnosis and the treatment recommendation for the cancer in the subject, wherein the generating is based on the cancer cell features.

In some embodiments, the treatment recommendation of the automatically generated report comprises an effective amount of a therapeutic agent, which effective amount of the therapeutic agent is administered to the subject to treat the cancer in the subject. In other embodiments, the artificial neural network comprises a convolutional neural network. In yet other embodiments, the methods and systems further comprise applying a dimensionality reduction algorithm to the feature coordinate space to: (a) generate a computed coordinate space, and (b) map each of the plurality of events of interest from a location in the feature coordinate space to a corresponding location in the computed coordinate space. In still other embodiments, the computed coordinate space is generated with a number of dimensions fewer than the number of dimensions of the feature coordinate space.

In some embodiments, the dimensionality reduction algorithm comprises a principal component analysis. In other embodiments, the plurality of events of interest comprises one or more cells, the plurality of event features comprises one or more cell features, and the event population of interest comprises one or more cell populations of interest. In still other embodiments, the one or more cell features are selected from the group consisting of a morphological feature, a cell marker, a protein concentration, a lipid content, an axial light loss, an optical phase, an optical loss, and combinations thereof; and wherein the one or more cell populations of interest are selected from the group consisting of polymorphonuclear myeloid derived suppressor cells (PMN-MDSCs), monocytic MDSCs (M-MDSCs), early-stage MDSCs (e-MDSCs), granulocytic MDSCs (g-MDSCs), and combinations thereof. In still other embodiments, the artificial neural network comprises an additional test result as an input, wherein the additional test is a prostate-specific antigen (PSA) test; a prostate specific membrane antigen (PSMA) test; a Carcino-embryonic antigen (CEA) test; a Cancer antigen 125 (CA-125) test; a peripheral blood mononuclear cell (PBMC)-to-neutrophil ratio test; another protein, nucleic acid, or other biomarker test; an X-ray; or a computed tomography (CT) scan.

In some embodiments, the therapeutic agent to treat the cancer in the subject comprises a radiation therapy, a chemotherapy, an immunotherapy, a targeted therapy, a hormone therapy, a stem cell therapy, or combinations thereof. In still other embodiments, the distribution in the feature coordinate space indicative of the event population of interest is formed by: (a) dividing each axis of the feature coordinate space into a plurality of segments, thereby dividing the coordinate space into a plurality of hypervoxels; and (b) for each hypervoxel of the plurality of hypervoxels, determining a count of a number of events of interest comprising an event feature value that locates the event of interest in the hypervoxel.

Also included herein are systems and methods for applying artificial neural networks to a first plurality and a second plurality of events of interest in a plurality of biological samples from a subject to generate a medical diagnosis and a treatment recommendation of a cancer in the subject, comprising: (a) performing, by a computer, analysis of the plurality of biological samples from the subject, the analysis comprising: 1) obtaining measurements of a first biological sample of a first plurality of event features for each of the first plurality of events of interest with a flow cytometer instrument, 2) using four or more flow cytometer measurement channels to define a first feature coordinate space, the first feature coordinate space comprising four or more axes, each axis corresponding to a different channel of the four or more flow cytometer measurement channels, wherein each of the four or more flow cytometer measurement channels produces measurements of the first plurality of event features, 3) using the measurements of the first plurality of event features for the first plurality of events of interest to define locations for the first plurality of events of interest in the first feature coordinate space to form a first distribution in the first feature coordinate space indicative of a first event population of interest, 4) obtaining measurement values of a second biological sample of a second plurality of event features for each of the second plurality of events of interest with a flow cytometer instrument, 5) using a plurality of flow cytometer measurement channels to define a second feature coordinate space, the second feature coordinate space comprising a plurality of axes, each axis corresponding to a different channel of the plurality of flow cytometer measurement channels, wherein each of the plurality of flow cytometer measurement channels produces measurements of the second plurality of event features, and 6) using the measurement values of the second plurality of event features for the second plurality of events of interest to define locations for the second plurality of events of interest in the second feature coordinate space to form a second distribution in the second feature coordinate space indicative of a second event population of interest; (b) applying, by the computer, an artificial neural network detection structure to the distribution in the first feature coordinate space indicative of the first event population of interest, the detection structure employing an artificial neural network to correlate the distribution in the first feature coordinate space indicative of the first event population of interest with a distribution of a first reference event population; (c) applying, by the computer, an artificial neural network detection structure to the distribution in the second feature coordinate space indicative of the second event population of interest, the detection structure employing an artificial neural network to correlate the distribution in the second feature coordinate space indicative of the second event population of interest with a distribution of a second reference event population; (d) determining, by the computer, whether the biological sample contains cells indicative of a cancer in the subject, thereby diagnosing the cancer in the subject; (e) identifying, by the computer, characteristic cell features of cells indicative of cancer; and (f) automatically generating, by the computer, a report comprising the medical diagnosis and the treatment recommendation for the cancer in the subject, wherein the generating is based on the cancer cell features.

In some embodiments, the methods and systems provided herein further comprises performing an algorithmic calculation using the additional test result to improve a medical diagnostic result. In yet other embodiments, a therapeutic agent to treat the cancer in the subject comprises a radiation therapy, a chemotherapy, an immunotherapy, a targeted therapy, a hormone therapy, a stem cell therapy, or combinations thereof. In still other embodiments, the distribution in the first feature coordinate space indicative of the first event population is formed by: (a) dividing each axis of the first feature coordinate space into a plurality of segments, thereby dividing the first feature coordinate space into a first plurality of hypervoxels; (b) for each hypervoxel of the first plurality of hypervoxels, determining a count of a number of first events of interest comprising an event feature value that locates the first event of interest in the hypervoxel; (c) dividing each axis of the second feature coordinate space into a plurality of segments, thereby dividing the second feature coordinate space into a second plurality of hypervoxels; and (d) for each hypervoxel of the second plurality of hypervoxels, determining a count of a number of second events of interest comprising an event feature value that locates the second feature of interest in the hypervoxel. In other embodiments, the distribution in the first feature coordinate space indicative of the first event population distribution comprises a cell population distribution.

In some embodiments, provided herein are systems and methods for training an improved artificial neural network to generate a medical diagnosis and a treatment recommendation of a cancer in a subject, comprising: (a) receiving a sample from a subject at a remote site; (b) obtaining flow cytometry data from the sample with a flow cytometer instrument; (c) transmitting the flow cytometry data to a central repository; (d) transmitting a subject status from the remote site to the central repository; (e) performing, by a computer, analysis of the flow cytometry data at a central site using an artificial neural network to determine a classification for the flow cytometry data; (f) transmitting the classification to the remote site, wherein the classification comprises a medical diagnosis of a cancer in the subject; (g) automatically generating, by the computer, a report comprising the medical diagnosis and a treatment recommendation of the cancer in the diagnosed subject, wherein the generating is based on the medical diagnosis; and (h) administering an effective amount of a therapeutic agent to the diagnosed subject to treat the cancer in the diagnosed subject.

In some embodiments, the systems and methods further comprises:(a) using the subject status and the flow cytometry data to augment a training data set and a target data set, and (b) using the augmented training data set and the augmented target data set to train an improved artificial neural network. In still other embodiments, the flow cytometry data is obtained from an MDSC cell population. In yet other embodiments, the therapeutic agent to treat the cancer in the subject comprises a radiation therapy, a chemotherapy, an immunotherapy, a targeted therapy, a hormone therapy, a stem cell therapy, or combinations thereof.

Also included herein are computer-implemented systems comprising: a digital processing device comprising: at least one processor, an operating system configured to perform executable instructions, a memory, and a computer program including instructions executable by the digital processing device to create an application applying artificial neural networks to a plurality of events of interest in a biological sample from a subject to generate a medical diagnosis and a treatment recommendation of a cancer in the subject, comprising: (a) measurements of a plurality of event features for each of the plurality of events of interest, the measurements obtained with a flow cytometer instrument; and (b) a software module performing analysis of the biological sample from the subject, the analysis comprising: 1) using four or more flow cytometer measurement channels to define a feature coordinate space, the feature coordinate space comprising four or more axes, each axis corresponding to a different channel of the four or more flow cytometer measurement channels, wherein each of the four or more flow cytometer measurement channels produces measurements of the plurality of event features, 2) using the measurements of the plurality of event features for the plurality of events of interest to define locations for the plurality of events of interest in the feature coordinate space to form a distribution in the feature coordinate space indicative of an event population of interest, and 3) applying an artificial neural network detection structure to the distribution in the feature coordinate space indicative of the event population of interest, the detection structure employing an artificial neural network to correlate the distribution in the feature coordinate space indicative of the event population of interest with a distribution in a reference feature coordinate space indicative of a reference event population; (c) a software module determining whether the biological sample contains cells indicative of the cancer in the subject, thereby diagnosing the cancer in the subject; (d) a software module identifying characteristic cell features of cells indicative of cancer; and (e) a software module automatically generating a report comprising the medical diagnosis and the treatment recommendation for the cancer in the subject, wherein the generating is based on the cancer cell features.

In some embodiments, provided herein are systems and methods of training an artificial neural network, the method comprising: (a) performing, by a computer, an augmentation process comprising: (1) obtaining a biological data sample comprising measurements from a flow cytometer instrument of a plurality of event features for a plurality of events of interest of a biological sample; (2) generating a sub-sample, wherein the generating comprises selecting measurements of event features from a subset of the events of interest from the biological data sample; and (b) applying, by the computer, a training process to an artificial neural network, wherein the training process comprises analyzing the sub-sample. In some embodiments, the method further comprises the artificial neural network that is capable of continually training. In some embodiments, the step (a) of the method further comprises: using four or more flow cytometer measurement channels to define a feature coordinate space, the feature coordinate space comprising four or more axes, each axis corresponding to a different channel of the four or more flow cytometer measurement channels, wherein each of the four or more flow cytometer measurement channels produces measurements of the event features of the sub-sample, and using the measurements of the event features of the sub-sample to define locations for the subset of events of interest in the feature coordinate space to form a distribution in the feature coordinate space indicative of an event population of interest, wherein the distribution in the feature coordinate space indicative of the event population of interest is formed by: (i) dividing each axis of the feature coordinate space into a plurality of segments, thereby dividing the coordinate space into a plurality of hypervoxels, and (ii) for each hypervoxel of the plurality of hypervoxels, determining a count of a number of events of interest comprising an event feature value that locates the event of interest in the hypervoxel. In some embodiments, the method comprises repeating step (a)(2) at least one time to generate sibling samples, wherein the sibling samples are at least two sub-samples generated from the biological data sample. In some embodiments, the sibling samples comprise a first sibling sample and a second sibling sample, wherein the first sibling sample has a different subset of the events of interest than the second sibling sample. In some embodiments, the sibling samples comprise a first sibling sample and a second sibling sample, wherein the first sibling sample comprises a number (N) of measurements of the biological sample and a second sibling sample, wherein the second sibling sample comprises at least N/4 measurements of the biological sample. In some embodiments, the number (N) of measurements comprises at least 5,000 events. In some embodiments, the number (N) of measurements is between 5,000 to 100,000 events. In some embodiments, the method improves a performance characteristic of the artificial neural network in detecting a condition in the biological sample, wherein the performance characteristic comprises at least one of a sensitivity and a specificity of detecting the condition in the biological sample, by at least 0.1% as compared to a sensitivity and a specificity of detecting the condition in the biological sample without the augmentation process. In some embodiments, the augmentation process (a) further comprises: obtaining a second biological data sample comprising measurements from a flow cytometer instrument of a plurality of event features for a plurality of events of interest of a second biological sample; generating a sub-sample of the second biological data sample, wherein generating comprises selecting measurements of event features from a subset of the events of interest from the second biological data sample; and the training process further comprises analyzing the sub-sample of the second biological data sample. In some embodiments, the method further comprises: (c) determining a status of a condition in a subject by applying, by the computer, the artificial neural network to data obtained from a naïve biological sample from the subject, wherein the data comprise a plurality of event features for a plurality of events from the subject; and (d) generating, by the computer, a report comprising the status of the condition in the subject. In some embodiments, the method comprises applying, by the computer, an artificial neural network detection structure to the distribution in the feature coordinate space indicative of the event population of interest, the detection structure employing an artificial neural network to correlate the distribution in the feature coordinate space indicative of the event population of interest with a distribution in a reference feature coordinate space indicative of a reference event population. In some embodiments, determining the status of the condition in the subject further comprises determining, by the computer, whether the biological sample contains cells indicative of the condition in the subject. In some embodiments, the method comprises identifying, by the computer, characteristic cell features of cells indicative of the condition. In some embodiments, the method comprises using the status of the condition in the subject and cell feature data to further train the artificial neural network. In some embodiments, the status of the condition comprises a presence of the condition, an absence of the condition, an increase in severity of the condition, a decrease in severity of the condition, a stage of the condition, a status associated with a prognosis, or a response to a therapy. In some embodiments, the training process in (b) further comprises updating the artificial neural network to improve a performance characteristic of the artificial neural network. In some embodiments, the method improves a performance characteristic of the artificial neural network in detecting a condition in the biological sample, wherein the performance characteristic comprises at least one of a sensitivity and a specificity of detecting the condition in the biological sample by at least 0.1% as compared to a sensitivity and a specificity of detecting the condition in the biological sample without the augmentation process. In some embodiments, a sibling sample is used for one of training, validating, and testing during the training process of the artificial neural network. In some embodiments, the sibling samples are used for one of training, validating, and testing during the training process of the artificial neural network. In some embodiments, the artificial neural network is a previously trained artificial neural network. In some embodiments, selecting measurements of event features from the subset of the events of interest from the biological data sample comprises randomly selecting a measurement of an event feature from the subset of events of interest. In some embodiments, the augmentation process is performed in at least two successive training processes of the artificial neural network. In some embodiments, an additional sibling sample is generated for an additional successive training process of the artificial neural network. In some embodiments, the additional sibling sample is generated for every M artificial neural networks trained, wherein M is at least 5. In some embodiments, the additional sibling sample is generated for every M artificial neural networks trained, wherein M is between 3 and 30. In some embodiments, the artificial neural network comprises a convolutional neural network. In some embodiments, the method further comprises applying a dimensionality reduction algorithm to the feature coordinate space to (a) generate a computed coordinate space and (b) map each of the plurality of events of interest from a location in the feature coordinate space to a corresponding location in the computed coordinate space. In some embodiments, the dimensionality reduction algorithm comprises a principal component analysis. In some embodiments, the events of interest comprise one or more cells, the event features comprise one or more cell features, and the event population of interest comprises one or more cell populations of interest. In some embodiments, the one or more cell features are selected from the group consisting of a morphological feature, a cell marker, a protein concentration, a lipid content, an axial light loss, an optical phase, an optical loss, and combinations thereof; and wherein the one or more cell populations of interest are selected from the group consisting of polymorphonuclear myeloid derived suppressor cells (PMN-MDSCs), monocytic MDSCs (M-MDSCs), early-stage MDSCs (e-MDSCs), granulocytic MDSCs (g-MDSCs), and combinations thereof.

In another aspect, provided herein are a computer-implemented method of using a trained artificial neural network to determine a status of a condition of a subject, the method comprising: (a) performing, by a computer, an analysis of a biological sample from a subject, the analysis comprising: (1) obtaining a biological data sample comprising measurements obtained from a flow cytometer instrument of a plurality of event features for a plurality of events of interest from the biological sample; (b) determining a status of a condition of the subject by applying, by the computer, an artificial neural network to the biological data sample. In some embodiments, the method further comprises performing, by the computer, an augmentation process comprising: (a)(2) generating a sub-sample, wherein the generating comprises selecting measurements of event features from a subset of the events of interest; and (a)(3) repeating step (a)(2) to generate sibling samples, wherein the sibling samples are two or more sub-samples from the biological data sample. In some embodiments, step (a) of the method further comprises: using four or more flow cytometer measurement channels to define a feature coordinate space, the feature coordinate space comprising four or more axes, each axis corresponding to a different channel of the four or more flow cytometer measurement channels, wherein each of the four or more flow cytometer measurement channels produces measurements of the event features of the sub-sample, and using the measurements of the event features of the sub-sample to define locations for the subset of events of interest in the feature coordinate space to form a distribution in the feature coordinate space indicative of an event population of interest, wherein the distribution in the feature coordinate space indicative of the event population of interest is formed by: (i) dividing each axis of the feature coordinate space into a plurality of segments, thereby dividing the coordinate space into a plurality of hypervoxels, and (ii) for each hypervoxel of the plurality of hypervoxels, determining a count of a number of events of interest comprising an event feature value that locates the event of interest in the hypervoxel. In some embodiments, the method further comprises applying a dimensionality reduction algorithm to the feature coordinate space to (a) generate a computed coordinate space and (b) map each of the plurality of events of interest from a location in the feature coordinate space to a corresponding location in the computed coordinate space. In some embodiments, the dimensionality reduction algorithm comprises a principal component analysis. In some embodiments, the events of interest comprise one or more cells, the event features comprise one or more cell features, and the event population of interest comprises one or more cell populations of interest. In some embodiments, the one or more cell features are selected from the group consisting of a morphological feature, a cell marker, a protein concentration, a lipid content, an axial light loss, an optical phase, an optical loss, and combinations thereof; and wherein the one or more cell populations of interest are selected from the group consisting of polymorphonuclear myeloid derived suppressor cells (PMN-MDSCs), monocytic MDSCs (M-MDSCs), early-stage MDSCs (e-MDSCs), granulocytic MDSCs (g-MDSCs), and combinations thereof. In some embodiments, applying comprises comprising applying, by the computer, an artificial neural network detection structure to the distribution in the feature coordinate space indicative of the event population of interest, the detection structure employing an artificial neural network to correlate the distribution in the feature coordinate space indicative of the event population of interest with a distribution in a reference feature coordinate space indicative of a reference event population. In some embodiments, determining the status of the condition in the subject further comprises determining, by the computer, whether the biological sample contains cells indicative of the condition in the subject. In some embodiments, the method further comprises identifying, by the computer, characteristic cell features of cells indicative of the condition. In some embodiments, the artificial neural network is capable of continually training. In some embodiments, the method further comprises using the status of the condition in the subject and cell feature data to further train the artificial neural network. In some embodiments, the sibling samples comprise a first sibling sample and a second sibling sample, wherein the first sibling sample comprises a number (N) of measurements of the biological sample and the second sibling sample comprises at least N/4 measurements of the biological sample. In some embodiments, the number (N) of measurements is at least 5,000 events. In some embodiments, the number (N) of measurements is between 5,000 and 100,000 events. In some embodiments, a plurality of sibling samples is tested by the artificial neural network, wherein the testing provides a status of a condition, wherein the status of the condition indicates a presence or an absence of a disease condition. In some embodiments, the status of the condition of a first sibling sample of a plurality of sibling samples is determined independently of the status of the condition of a second sibling sample of the plurality of sibling samples from the same biological data sample, wherein the statuses of the condition for the plurality of the sibling samples are provided by the same artificial neural network. In some embodiments, the artificial neural network provides the status of the condition for at least three sibling samples from the same biological data sample to give a global status category of the biological data sample, wherein the global status category comprises the most probable category based on a frequency of the statuses of the condition of the sibling samples. In some embodiments, the artificial neural network is one of at least three artificial neural networks that are used by a master network where the at least three artificial networks vary in at least one of number of network layers, number of neurons used, training function, method of output error calculation, weight and bias updating method, number of inputs, type of inputs, and combinations thereof In some embodiments, method further comprises (c) identifying, by the computer, characteristic event features indicative of the status of the condition, thereby providing the status of the condition of the biological data sample and diagnosing the status of the condition in the subject. In some embodiments, the method further comprises (d) automatically generating, by the computer, a report comprising the status of the condition and a treatment recommendation for the status of the condition in the subject, wherein the generating is based on characteristic event features indicative of the status of the condition. In some embodiments, the artificial neural network is a previously trained artificial neural network. In some embodiments, the selecting measurements of event features from a subset of the events of interest comprises randomly selecting a measurement of an event feature from the subset of events of interest. In some embodiments, the status of the condition comprises a presence of the condition, an absence of the condition, an increase in severity of the condition, a decrease in severity of the condition, a stage of the condition, a status associated with a prognosis, or a response to a therapy. In some embodiments, multiple artificial neural networks are applied to the biological data sample and used to provide multiple statuses of the condition, wherein the multiple artificial neural networks are trained separately, wherein the multiple artificial neural networks provide an independent status of the condition. In some embodiments, the statuses of the condition by the multiple artificial neural networks are analyzed by a master neural network to give a global status category of the biological sample, wherein the global status category is the most probable category based on a frequency of the statuses of the condition of the biological data sample. In some embodiments, the multiple artificial neural networks used by the master neural network vary in number of network layers, number of neurons used, training function, method of output error calculation, weight and bias updating method, number of inputs, type of inputs, or combinations thereof. In some embodiments, the artificial neural network comprises a network output classifier, the network output classifier comprising a sigmoid activation function, wherein the sigmoid activation function comprising a network sigmoid output value over a threshold is classified into a first status and the value at or below the threshold is classified into a second status. In some embodiments, the threshold is between 0.3 and 0.7. In some embodiments, the threshold is 0.5. In some embodiments, a transformation is applied, the transformation rescaling the network sigmoid output value to give the status of the condition for a chosen threshold. In some embodiments, the network output classifier is adjusted to improve at least one of sensitivity and specificity of the biological sample by at least 0.1% as compared to classification without the network output classifier adjustment. In some embodiments, the analysis of the biological sample from the subject further comprises: (a)(2) grouping the measurements of the plurality of event features into a plurality of bins, a bin representing a subset associated with a range of measured values; (a)(3) applying a filter to the plurality of bins, wherein application of the filter comprises: (i) identifying the bins populated with no measurements and the bins populated with measurements of undesired event features; and (ii) creating a biological data sample of desired bins, wherein the bins identified in (i) are removed from the biological data sample prior to training the artificial neural network. In some embodiments, a number of the plurality of bins in the biological data sample is reduced by at least 50%.

In another aspect, provided herein are a computer-implemented method of applying an artificial neural network to a biological data sample from a biological sample from a subject to generate a status of a condition and a treatment recommendation, the method comprising: (a) performing, by a computer, analysis of a biological data sample from a biological sample from a subject, the analysis comprising: (1) obtaining the biological data sample from measurements obtained from a flow cytometer instrument of a plurality of event features for a plurality of events of interest in the biological sample; (b) applying, by the computer, an artificial neural network to the biological data sample, wherein the artificial neural network provides a status of a condition in the subject. In some embodiments, the method further comprises automatically generating, by the computer, a report comprising the status of the condition in the subject. In some embodiments, the method further comprises generating, by the computer, a treatment recommendation for the condition in the subject, wherein the generating is based on identification of cell features indicative of the condition. In some embodiments, the status of the condition comprises a presence of the condition, an absence of the condition, an increase in severity of the condition, a decrease in severity of the condition, a stage of the condition, a status associated with a prognosis, or a response to a therapy. In some embodiments, the biological data sample comprises measurements from the biological sample from the subject collected at a first time point and wherein the method further comprises repeating steps (a) and (b) on at least a second biological sample from the subject collected at one or more subsequent time points. In some embodiments, the status of the condition collected at the first time point provides a baseline status of the subject and the status of the condition of the second biological sample is monitored for a change from the baseline status. In some embodiments, the baseline status indicates a diagnosis of the condition in the subject and the status of the condition of the second biological sample is used to monitor a response of the subject to a treatment for the condition in the subject, wherein the response is used to adjust the treatment, wherein the adjusting the treatment comprises changing a dose, frequency, type of treatment, or combination thereof. In some embodiments, the artificial neural network further provides a prediction of a response of the subject to a treatment based on the analysis of the biological data sample. In some embodiments, the artificial neural network is capable of continually training. In some embodiments, the artificial neural network is a previously trained artificial neural network. In some embodiments, providing a status of a condition in the subject comprises providing a diagnosis. In some embodiments, the condition comprises cancer, diabetes, Parkinson's disease, Alzheimer's disease, pancreatitis, multiple sclerosis, hepatitis, tuberculosis, or HIV, or combinations thereof. In some embodiments, the method is performed in conjunction with a screening test for the condition. In some embodiments, the screening test comprises a mammogram, a rectal exam, a prostate-specific antigen test, a computed tomography, an X-ray, or combinations thereof. In some embodiments, the method further comprises a DNA sequencing diagnostic test for the condition, wherein the DNA sequencing diagnostic test identifies the status of the condition or mutations indicative of the condition. In some embodiments, the method further comprises assessing the events for biomarkers of the condition. In some embodiments, the biological data sample further comprises data of a result of a biomarker assay, wherein the biomarker assay detects biomarkers of the condition. In some embodiments, the artificial neural network comprises a convolutional neural network.

In another aspect, provided herein are a computer-implemented method of updating an artificial neural network for generating a status of a condition of a biological sample, the method comprising: (a) obtaining a biological data sample, the biological data sample comprising measurements obtained from a flow cytometer instrument of a plurality of event features for a plurality of events of interest in a biological sample; (b) performing, by a computer, an analysis of measurements of the biological sample, the analysis comprising applying, by the computer, a training process to an artificial neural network; (c) updating the artificial neural network by iteratively performing steps (a) and (b) with a biological data sample from at least one additional biological sample. In some embodiments, the method further comprises using the updated artificial neural networks to provide a status of a condition of at least one additional biological sample. In some embodiments, the method further comprises automatically generating, by the computer, a report comprising the status of the condition. In some embodiments, the method further comprises generating, by the computer, a treatment recommendation for the condition, wherein the generating is based on identification of the event features indicative of the condition. In some embodiments, the updating of the artificial neural network occurs on a continual basis. In some embodiments, the at least one additional biological sample comprises at least 100 biological data samples. In some embodiments, the method is performed at least one time a year. In some embodiments, the updating adds biological data samples from one or more biological samples to the training process. In some embodiments, the method further comprises performing an augmentation process to the biological data sample to generate a sub-sample before performing the analysis of measurement, wherein generating comprises selecting measurements of event features from the events of interest from the biological data sample.

In another aspect, provided herein are a computer-implemented method of updating an artificial neural network for a status of a condition of a biological sample, the method comprising: (a) obtaining a biological data sample, the biological data sample comprising measurements obtained from a flow cytometer instrument of a plurality of event features for a plurality of events of interest in a biological sample; (b) performing an augmentation process on the biological data sample to generate a sub-sample before performing the analysis of measurement, wherein generating comprises selecting measurements of event features of the events of interest from the biological data sample; (c) performing, by a computer, analysis of the sub-sample, the analysis comprising applying, by the computer, a training process to an artificial neural network; (d) updating the artificial neural network by iteratively performing steps (a) to (c) with at least one additional biological data sample. In some embodiments, the method further comprises using the updated artificial neural network to provide a status of a condition of the biological data sample. In some embodiments, updating the artificial neural network occurs on a continual basis. In some embodiments, the method further comprises automatically generating, by the computer, a report comprising a medical diagnosis. In some embodiments, the method further comprises generating, by the computer, a treatment recommendation for the condition, wherein the generating is based on identification of the event features indicative of a condition. In some embodiments, the at least one additional biological data sample comprises at least 100 biological data samples. In some embodiments, the updating is performed at least one time a year. In some embodiments, the updating adds biological data samples from one or more biological samples to the training process.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE INVENTION

Figure 1:
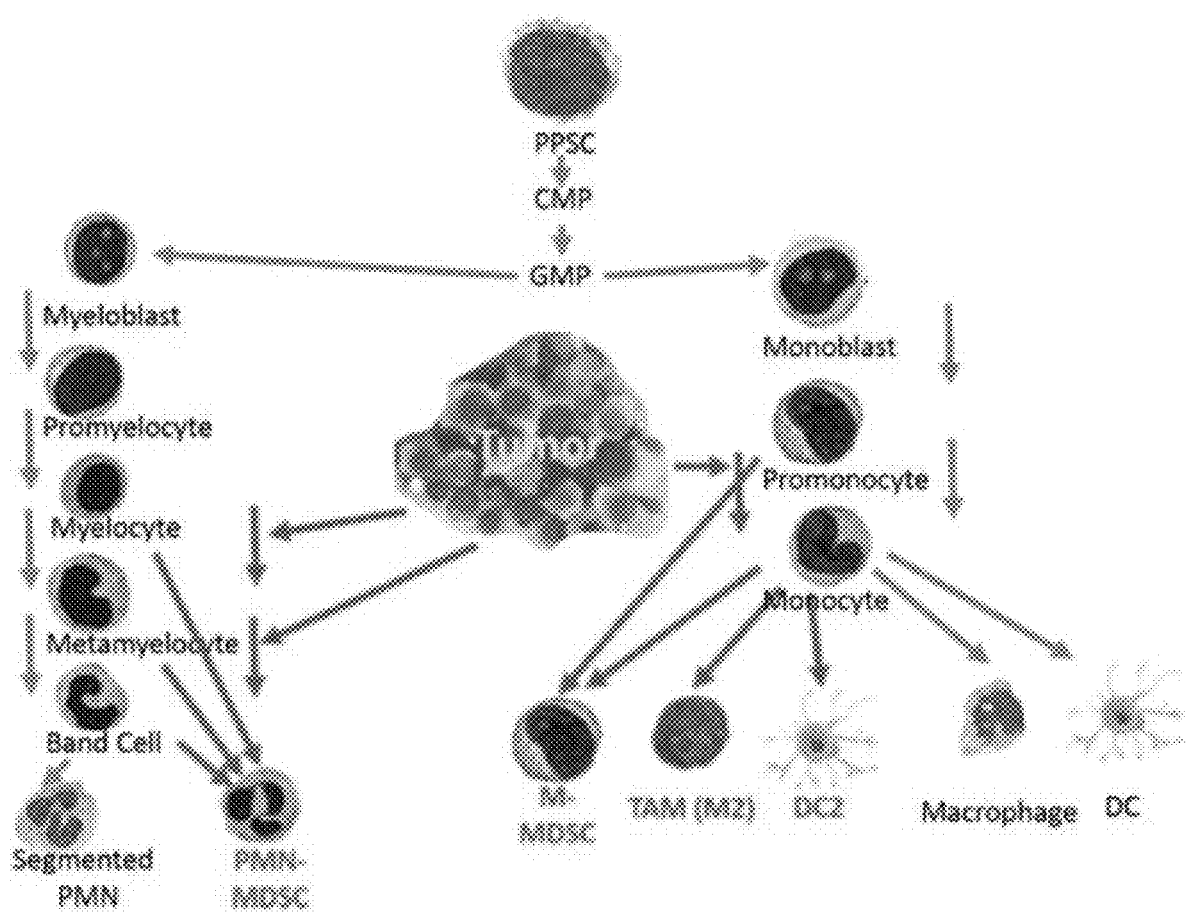
FIG. 1 is an illustration of the proposed development of myeloid-derived suppressor cells (MDSCs), including subtypes of MDSCs, from pluripotent stem cells.

Characterizing cells and cell populations in a biological study is an important step in understanding disease presence and progression. Flow cytometry is used to investigate cells, for example in cancer studies. The present disclosure is directed toward methods and systems for detecting cells of interest in peripheral blood. The technology can be used in various settings, e.g., cancer detection, disease diagnosis, disease staging, etc.

Target Cells

In various aspects, provided herein are systems and methods for identifying and optionally characterizing a cell of interest as a target cell by analyzing a signature of the cell of interest and comparing it to a signature of the target cell. A signature of a cell may include a feature of the cell, such as cell morphology, as well as the presence, absence, or relative amount of one or more biomarkers within and/or associated with the cell. Biomarkers cover a broad range of biochemical entities, such as nucleic acids, proteins, lipids, carbohydrates, small metabolites, and cytogenetic and cytokinetic parameters. A signature of a cell of interest is useful for diagnosing or otherwise characterizing a status of a disease or a condition in a patient from which the potential target cell was isolated. As used herein, an isolated cell refers to a cell separated from other material in a biological sample using any separation method. An isolated cell may be present in an enriched fraction from the biological sample, and thus its use is not meant to be limited to a purified cell. In some embodiments, the morphology of an isolated cell is analyzed. In some embodiments, analyzing comprises determining the presence or absence of a biomarker in or on the surface of the cell. In some embodiments, analyzing comprises determining a level of a biomarker within or associated with the cell. For target cells indicative of cancer, analysis of a cell signature is useful for a number of methods including diagnosing cancer, determining a stage of cancer, determining a type of cancer, and monitoring progression of cancer with a given treatment. Some of these methods may involve monitoring a change in the signature of the target cell, which includes an increase and/or decrease of a biomarker and/or any change in morphology.

In some embodiments, the signature of a cell of interest is analyzed in a fraction of a biological sample of a subject, wherein the biological sample has been processed to enrich for a target cell. In some cases, the enriched fraction lacks the target cell and the absence of a signature of a target cell in the enriched fraction indicates this absence. Target cells include tumor-associated cells, such as myeloid-derived suppressor cells (MDSCs) and other myeloid-derived cells, and lymphoid cells, such as Natural killer cells, T lymphocytes, B lymphocytes, and other lymphoid cells.

Target Cell Populations and Population Distributions

The identified target cells in aggregate form target cell populations and form target cell population distributions. These populations can be thought of as point clouds that display characteristic shapes and have aggregate locations in a multidimensional space. In the multidimensional space disclosed herein, an axis is defined by a flow cytometry measurement channel, which is a source of signal measurements in flow cytometry. Signals measured in flow cytometry may include, but are not limited to, optical signals and biomarker measurements. Exemplary channels of optical signals include, but are not limited to, one or more of the following: forward scatter channels, side scatter channels, and laser fluorescence channels. Exemplary channels of biomarker measurements include, but are not limited to, one or more of the following biomarkers: B7-H4, CCR2, CXCR4, CXCR2, CD1d, CD1d1, CD3, CD4, CD8, CD11a, CD11b, CD11c, CD14, CD15, CD16, CD16a, CD16b, CD16, CD19, CD21, CD31, CD32, CD32a, CD32b, CD32b/c, CD32c, CD33, CD34, CD35, CD38, CD39, CD40, CD44, CD45, CD49d, CD56, CD62L, CD62b, CD66b, CD80, CD86, CD115, CD117, CD124, CD162, CD172a, CD192, CD301a, CD301a/b, CD301b, Complement Component C5a RI, EMR1, F4/80, Galectin-3, gp130, Gf-1, HLA-DR$^-$, ICAM-1/CD54, IL1RI, IL4Rα, IL-6Rα, LOX-1 (OLR1), Ly6, M-CSFR, nitric oxide, KIT, LIN$^-$, MHC I, PD-L1, TIE2, Transferrin R, VEGFR1, VEGFR2, Arginase I, B7-H4, CLEC5A, HLA-DR, MRP-14, NF-kB p50, SHIP-1, SSEA-1, STAT1, STAT3, LOX-1 (OLR1), and Integrin α4β1.

All flow cytometry instrument channels or a subset of the channels may be used for the axes in the multidimensional space. A population of cells may be considered to have changed in the multidimensional channel space when the channel values of its individual cell members change, and in particular when a large number of the cells in the population have changed channel values. For example, the point cloud representing a population of cells can be seen to vary in location on a 2-dimensional (2D) dot plot or intensity plot when samples are taken from the same individual at different times. Similarly, the point cloud representing a population of cells can shift, translate, rotate, or otherwise change shape in multidimensional space. Whereas conventional gating provides total cell count within a gate region, the location and other spatial parameters of certain cell population point clouds in multidimensional space, in addition to providing total cell count, provide additional information which can also be used distinguish between non-tumor-bearing subjects (e.g., subjects without malignant tumors) and cancer patients (e.g., subjects with malignant tumors).

Myeloid-Derived Suppressor Cells

An exemplary cell population that forms distributions in multidimensional flow cytometer channel space is myeloid-derived suppressor cells (MDSCs). MDSCs are a group of pathologically activated immature myeloid cells with immunosuppressive capability. MDSCs are generally defined as immature myeloid cells (e.g. immature and progenitor myeloid cells) that differ from terminally differentiated mature myeloid cells. MDSCs are morphologically and phenotypically similar to monocytes such as monocytic MDSCs (M-MDSCs) and polymorphonuclear (PMN) neutrophils such as polymorphonuclear MDSCs (PMN-MDSCs). They are defined functionally based on the inhibition of T-cell function and viability, but they may exhibit broad phenotypic, functional, and morphologic heterogeneity.

Expansion of MDSC populations in the peripheral blood has been shown to be associated with tumor growth. The absolute and relative distributions of sub-populations of MDSCs can be used to provide an indication of the presence, absence, or stage of cancer. For example, early-stage MDSCs (e-MDSCs), PMN-MDSCs, and M-MDSCs can form sub-population distributions that can be used for cancer diagnosis.

Figure 2A:
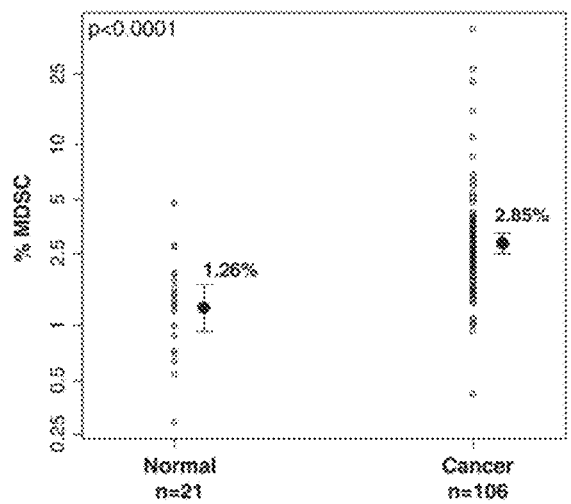
FIG. 2A is a graph illustrating that subjects with cancer have a significantly higher percentage of circulating MDSCs than subjects without cancer.
Figure 2B:
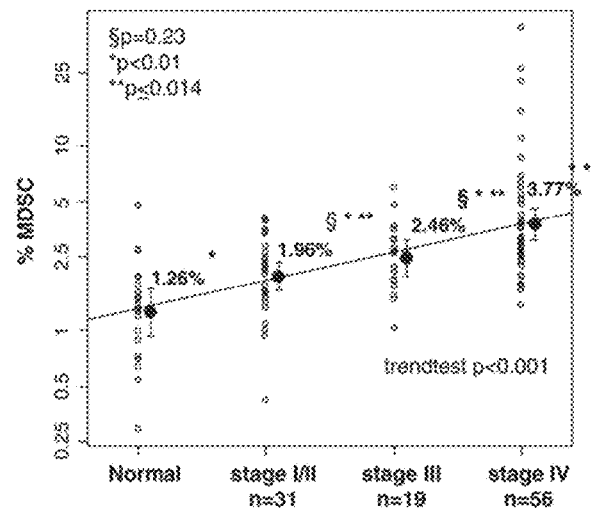
FIG. 2B is a graph correlating circulating MDSC percentage with cancer stage, and demonstrating that as a cancer progresses, the percentage of circulating MDSCs increases.
Figure 2C:
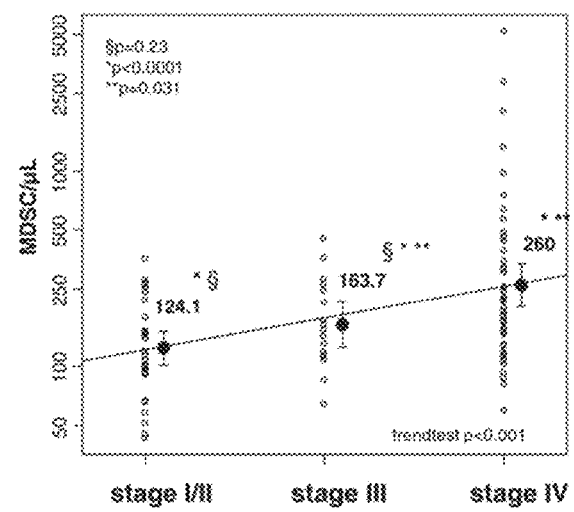
FIG. 2C is a graph reporting a significant trend in an increasing number of MDSCs per microliter of blood.

One proposed developmental tree of myeloid and lymphoid cells derived from pluripotent stem cells is shown in FIG. 1. MDSCs are believed to diverge from the granulocytic and monocytic development sequences and remain immature, while acquiring immunosuppressive functionality. The sub-population of e-MDSC is thought to branch off earlier in the granulocytic development sequence and can be isolated from the sub-population of PMN-MDSC, which diverges later. Once they have diverged from the standard development sequence, their differentiation into mature myeloid cells is arrested. Increases in circulating MDSCs have been shown to be positively correlated with clinical cancer stage and metastatic tumor burden (FIGS. 2A, 2B and 2C). Factors produced by tumor cells promote the expansion of MDSCs through stimulation of myelopoiesis and inhibiting differentiation of mature myeloid cells. MDSCs have also been shown to be activated by factors produced by activated T cells.

Flow Cytometry

Provided herein are systems and methods for identifying and optionally characterizing a cell of interest (e.g., an event of interest) as a target cell by analyzing a signature of the cell of interest. In some instances, a cell of interest is an MDSC cell. One or more biomarkers of a myeloid-derived suppressor cell in some cases are used to distinguish the cell from another tumor-derived cell or from a non-tumor-derived cell. In some instances, flow cytometry is used to measure a signature of a cell such as the presence, absence, or relative amount of one or more biomarkers within and/or associated with the cell, or through differentiating physical or functional characteristics of the target cells of interest.

Cells of interest identified using the systems and methods as described herein include cell types implicated in a disease or a non-disease state. Exemplary types of cells include, but are not limited to, cancer cells of all types including cancer stem cells, cardiomyocytes, dendritic cells, endothelial cells, epithelial cells, lymphocytes (T cell, NK cell, and B cell), mast cells, eosinophils, basophils, neutrophils, natural killer cells, erythrocytes, hepatocytes, leukocytes including mononuclear leukocytes, and stem cells such as hematopoietic, neural, skin, and monocyte stem cells. In some instances, cells of interest are at least one of lymphoid lineage or derived cells, myeloblast lineage or derived cells, neural stem cell lineage or derived cells, endodermal stem cell lineage or derived cells, mesenchymal stem cell lineage or derived cells. In some instances, cells of interest are disease state cells, such as cancer cells. In some cases, cells of interest are circulating cells, such as circulating tumor cells (CTCs).

Cells of interest in some cases are identified by at least one of alterations in cell morphology, cell volume, cell size and shape, amounts of cellular components such as total DNA, newly synthesized DNA, gene expression as the amount messenger RNA for a particular gene, amounts of specific surface receptors, amounts of intracellular proteins, signaling events, or binding events in cells. In some cases, cells of interest are identified by the presence or absence of biomarkers such as proteins, lipids, carbohydrates, and small metabolites.

Non-limiting examples of biomarkers within and/or associated with a cell that are measured using the methods and systems as described herein are B7-H4, CCR2, CXCR4, CXCR2, CD1d, CD1d1, CD3, CD4, CD8, CD11a, CD11b, CD11c, CD14, CD15, CD16, CD16a, CD16b, CD16, CD19, CD21, CD31, CD32, CD32a, CD32b, CD32b/c, CD32c, CD33, CD34, CD35, CD38, CD39, CD40, CD44, CD45, CD49d, CD56, CD62L, CD62b, CD80, CD86, CD115, CD117, CD124, CD162, CD301a, CD301a/b, CD301b, Complement Component C5a R1, EMR1, F4/80, Galectin-3, gp130, Gf-1, HLA-DR⁻, ICAM-1/CD54, IL1RI, IL4Rα, IL-6Rα, LOX-1 (OLR1), Ly6, M-CSFR, nitric oxide, KIT, LIN⁻, MHC I, PD-L1, SSEA-1, TIE2, Transferrin R, VEGFR1, VEGFR2, and Integrin α4β1. Alternately, or in combination, signaling proteins are measured by flow cytometry. For example, signaling proteins including, but not limited to, kinases, kinase substrates (e.g., phosphorylated substrates), phosphatases, phosphatase substrates, binding proteins (such as 14-3-3), receptor ligands, and receptors (e.g., cell surface receptor tyrosine kinases and nuclear receptors).

In some instances, the presence of a biomarker is measured. Alternately, the absence of a biomarker is measured. In some instances, a relative amount of a biomarker is measured. For example, presence of surface markers such as CD11b, CD15, CD66, or CD14 on MDSCs is determined. In some instances, an absence of surface markers CD14, HLA-DR, or CD15 on MDSCs is determined. Sometimes expression of surface markers of MDSCs is in a relative amount such as for HLA-DR. In some instances, the presence of markers such as CD3, CD14, SSEA-1, CD16, CD33, HLA-DR, CD19, CD56, LOX-1 (OLR1), or CD11b on MDSCs is determined. In some instances, the presence of markers such as CD3, CD19, CD56, CD4, or CD8 on lymphocytes is determined.

In some instances, cells are acquired from a subject by a blood draw, a marrow draw, or a tissue extraction. Often, cells are acquired from peripheral blood of a subject. Sometimes, a blood sample is centrifuged using a density centrifugation to obtain mononuclear cells, erythrocytes, and granulocytes. In some instances, the peripheral blood sample is treated with an anticoagulant. In some cases, the peripheral blood sample is collected in, or transferred into, an anticoagulant-containing container. Non-limiting examples of anticoagulants include heparin, sodium heparin, potassium oxalate, EDTA, and sodium citrate. Sometimes a peripheral blood sample is treated with a red blood cell lysis agent.

Alternately or in combination, cells are acquired by a variety of other techniques and include sources, such as bone marrow, solid tumors, ascites, washes, and the like. In some cases, tissue is taken from a subject using a surgical procedure. Tissue may be fixed or unfixed, fresh or frozen, whole or disaggregated. For example, disaggregation of tissue occurs either mechanically or enzymatically. In some instances, cells are cultured. The cultured cells may be developed cell lines or patient-derived cell lines. Procedures for cell culture are commonly known in the art.

Systems and methods as described herein can involve analysis of one or more samples from a subject. A sample may be any suitable type that allows for the analysis of different discrete populations of cells. A sample may be any suitable type that allows for analysis of a single cell population. Samples may be obtained once or multiple times from a subject. Multiple samples may be obtained from different locations in the individual (e.g., blood samples, bone marrow samples, and/or tissue samples), at different times from the individual (e.g., a series of samples taken to diagnose a disease or to monitor for return of a pathological condition), or any combination thereof. These and other possible sampling combinations based on sample type, location, and time of sampling allow for the detection of the presence of pre-pathological or pathological cells and monitoring for disease.

When samples are obtained as a series, e.g., a series of blood samples obtained after treatment, the samples may be obtained at fixed intervals, at intervals determined by status of a most recent sample or samples, by other characteristics of the individual, or some combination thereof. For example, samples may be obtained at intervals of approximately 1, 2, 3, or 4 weeks, at intervals of approximately 1, 2, 3, 4, 5, 6, 7, 8, 9, 10, or 11 months, at intervals of approximately 1, 2, 3, 4, 5, or more than 5 years, or some combination thereof.

To prepare cells for analysis using the methods and systems described herein, cells can be prepared in a single-cell suspension. For adherent cells, both mechanical or enzymatic digestion and an appropriate buffer can be used to remove cells from a surface to which they are adhered. Cells and buffer can then be pooled into a sample collection tube. For cells grown in suspension, cells and medium can be pooled into a sample collection tube. Adherent and suspension cells can be washed by centrifugation in a suitable buffer. The cell pellet can be re-suspended in an appropriate volume of suitable buffer and passed through a cell strainer to ensure a suspension of single cells in suitable buffer. The sample can then be vortexed prior to performing a method using the flow cytometry system on the prepared sample.

Once cell samples have been collected they may be processed and stored for later usage, processed and used immediately, or simply used immediately. In some cases, processing includes various methods of treatment, isolation, purification, filtration, or concentration. In some instances, fresh or cryopreserved samples of blood, bone marrow, peripheral blood, tissue, or cell cultures are used for flow cytometry.

When samples are stored for later usage, they may be stabilized by collecting the sample in a cell preparation tube such as a BD Vacutainer CPT™ (Becton, Dickinson and Company) and centrifuging the tube within 4 hours of collection, or a similar period. Use of this procedure may preserve the separation between MDSCs and non-MDSC neutrophils, which may become activated over longer periods and would thereby change their density and become intermingled with the MDSCs during later centrifugation.

In some instances, the number of cells that are measured by flow cytometry is about 1,000 cells, about 5,000 cells, about 10,000 cells, about 40,000 cells, about 100,000 cells, about 500,000 cells, about 1,000,000 cells, or more than 1,000,000 cells. In some instances, the number of cells that are measured by flow cytometry is up to about 1,000 cells, up to about 5,000 cells, up to about 10,000 cells, up to about 40,000 cells, up to about 100,000 cells, up to about 500,000 cells, up to about 1,000,000 cells, or more than 1,000,000 cells.

Cells are often labeled with a fluorophore-conjugated antibody that recognizes biomarkers associated with cells. Cells can be fixed or live cells. In some instances, a fluorophore-conjugated antibody recognizes cell surface antigens. In some cases, a fluorophore-conjugated antibody recognizes intracellular biomarkers. Often for a fluorophore-conjugated antibody to label intracellular markers, cells are fixed and permeabilized.

In general, flow cytometry involves the passage of individual cells through the path of one or more laser beams. A scattering of a beam and excitation of any fluorescent molecule attached to, or found within, a cell is detected by photomultiplier tubes to create a readable output. Often optical filters and beam splitters direct various scattered light to detectors, which generate electronic signals proportional to intensity of light signals received. Data can be collected, stored in computer memory, and cell characteristics analyzed based on fluorescent and light scattering properties. In some instances, flow cytometry involves analysis of a single sample or involves high-throughput screening, e.g. 96-well or greater microtiter plates. In some instances, the data are the measurements of the cell characteristics of the biological sample from a flow cytometer instrument.

Figure 3:
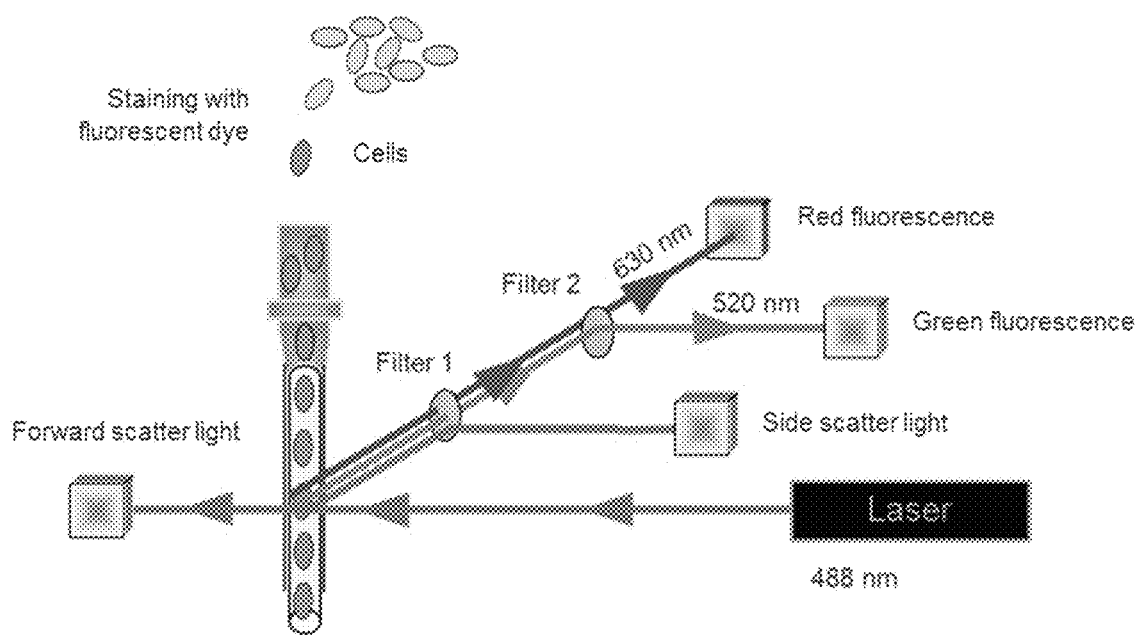
FIG. 3 is a simplified illustration of a flow cytometer. Cells can be labeled with one or more fluorescent probes and passed single-file in a stream of fluid past a laser light source. Fluorescence detectors measure the fluorescence emitted from labeled cells.

As seen in FIG. 3, cells may be labeled with one or more fluorophores and then excited by one or more lasers to emit light at the fluorophore emission frequency or frequencies. In some instances, fluorescence is measured as cells pass through multiple laser beams simultaneously. Several detection elements, e.g. fluorophore-conjugated antibodies or fluorescence markers, can be used simultaneously, so measurements made as one cell passes through a laser beam may consist of scattered light intensities as well as light intensities from each fluorophore. For example, at least 1, 2, 3, 4, 5, 6, 7, 8, 9, 10, 11, 12, 13, 14, 15, 16, 17, or more fluorescence markers are used. In some cases, a combination of fluorescence markers is used. Characterization of a single cell can comprise a set of measured light intensities that may be represented as a coordinate position in a multidimensional space (e.g., a feature coordinate space). A number of coordinate axes (the dimensions of the space) is often the number of fluorophores used plus one or more forward scatter or side scatter measurements.

Several types of fluorophores can be used as consistent with this application. Non-limiting examples are Alexa-Fluor dyes (e.g., Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, and Alexa Fluor® 750), APC, Cascade Blue, Cascade Yellow and R-phycoerythrin (PE), DyLight 405, DyLight 488, DyLight 550, DyLight 650, DyLight 680, DyLight 755, DyLight 800, FITC, Pacific Blue, PerCP, Rhodamine, Texas Red, Cy5, Cy5.5, and Cy7.

Alternately or in combination to fluorescence measurements, flow cytometry may measure at least one of cell size, cell volume, cell morphology, cell granularity, the amounts of cell components such as total DNA, newly synthesized DNA, gene expression as the amount messenger RNA for a particular gene, amounts of specific surface receptors, amounts of intracellular proteins, or signaling or binding events in cells. In some instances, cell analysis by flow cytometry on the basis of fluorescent level is combined with a determination of other flow cytometry readable outputs, such as granularity or cell size to provide a correlation between the activation level of a multiplicity of elements and other cell qualities measurable by flow cytometry for single cells.

In some instances, flow cytometry data is presented as a single parameter histogram. Alternatively, or additionally, flow cytometry data is presented as 2-dimensional (2D) plots of parameters called cytograms. Often in cytograms, two measurement parameters are depicted such as one on an x-axis and one on a y-axis. In some instances, parameters depicted comprise at least one of side scatter signals (SSCs), forward scatter signals (FSCs), and fluorescence. In some instances, data in a cytogram is displayed as at least one of a dot plot, a pseudo-color dot plot, a contour plot, or a density plot. For example, data regarding cells of interest is determined by a position of the cells of interest in a contour or density plot. The contour or density plot can represent a number of cells that share a characteristic such as expression of particular biomarkers.

Flow cytometry data is conventionally analyzed by gating. Often sub-populations of cells are gated or demarcated within a plot. Gating can be performed manually or automatically. Manual gates, by way of non-limiting example, can take the form of polygons, squares, or dividing a cytogram into quadrants or other sectional measurements. In some instances, an operator can create or manually adjust the demarcations to generate new sub-populations of cells. Alternately or in combination, gating is performed automatically. Gating can be performed, in some part, manually or in some part automatically.

In some instances of the methods and devices disclosed herein, gating is performed using a computing platform. A computing platform may be equipped with user input and output features that allow for gating of cells of interest. A computing platform typically comprises known components such as a processor, an operating system, system memory, memory storage devices, input-output controllers, input-output devices, and display devices. In some instances, a computing platform comprises a non-transitory computer-readable medium having instructions or computer code thereon for performing various computer-implemented operations.

Gating, in some instances, involves using scatter signals, for example forward scatter (FSC), to differentiate subcellular debris from cells of interest. In some instances, single cells are gated from multiple or clumps of cells. In some instances, cells in a sample can be individually gated from an analysis based on the viability of the cell. For example, gating is used to select out live cells and exclude the dead or dying cells in the population by cell staining. Exemplary stains are 4',6-diamidino-2-phenylindole (DAPI) or Hoescht stains (for example, Hoescht 33342 or 33258). In some instances, gating is applied to at least one fluorescent marker to identify cells of interest. In some instances, gating is applied to different fluorescent marker combinations to identify cells of interest. In some instances, a subset of cells is gated for further analysis or to identify cells associated with a same state.

In some instances, comparing changes in a set of flow cytometry samples is done by overlaying histograms of one parameter on a same plot. For example, arrayed flow cytometry experiments contain a reference sample against which experimental samples are compared. This reference sample can then be placed in the first position of an array, and subsequent experimental samples follow a control in a sequence. Reference samples can include normal and/or cells associated with a condition (e.g. tumor cells).

In some cases, prior to analyzing data, the cell populations of interest and the method for characterizing these populations are determined. For example, cell populations are homogenous or lineage gated in such a way as to create distinct sets considered to be homogenous for targets of interest. An example of sample-level comparison would be the identification of biomarker profiles in tumor cells of a subject and correlation of these profiles with biomarker profiles in non-diseased cells. In some instances, individual cells in a heterogeneous population are mapped. An example of this would be mapping of mixed myeloid cells under certain conditions and subsequent comparison of computationally identified cell clusters with lineage specific markers.

Alternately or in combination with flow cytometry, cells of interest are identified by other spectrophotometric means, including but not limited to mass cytometry, cytospin, or immunofluorescence. Immunofluorescence can be used to identify cell phenotypes by using an antibody that recognizes an antigen associated with a cell. Visualizing an antibody-antigen interaction can be accomplished in a number of ways. The antibody can be conjugated to an enzyme, such as peroxidase, that can catalyze a color-producing reaction. Alternately, the antibody can be tagged to a fluorophore, such as fluorescein or rhodamine.

The methods described herein are suitable for any condition for which a correlation between the cell biomarker profile of a cell and the determination of a disease predisposition, diagnosis, prognosis, and/or course of treatment in samples from individuals may be ascertained. Identification of cell surface biomarkers on cells can be used to classify one or more cells in a subject. In some instances, classification includes classifying the cell as a cell that is correlated with a clinical outcome. The clinical outcome can be prognosis and/or diagnosis of a condition, and/or staging or grading of a condition. In some instances, classification of a cell is correlated with a patient response to a treatment. In some cases, classification of a cell is correlated with minimal residual disease or emerging resistance. Alternately, classification of a cell includes correlating a response to a potential drug treatment. In some instances, classification includes classifying a sample dataset as a sample that is correlated with a clinical outcome or a condition, where the sample dataset is obtained from the measurements of cells in a biological sample. The sample dataset from a biological sample may also be referred to as biological data sample. The condition may include normal (non-tumor-bearing), cancer (malignant tumor-bearing), a stage of cancer, or other diseases. In some instances, the classification is performed on the sample dataset as multiple sample datasets may be obtained from a single biological sample, resulting in multiple classifications for the biological sample.

Often the methods and systems as described herein are used for diagnosis of disease. In some instances, a disease is cancer such as breast cancer, cervical cancer, ovarian cancer, colorectal cancer, melanoma, sarcoma, endometrial cancer, bladder cancer, renal cancer, gastric cancer, thyroid cancer, malignant lymphoma, lung cancer, prostate, cancer, liver cancer, and pancreatic cancer. In some instances, a first biomarker profile of cells of interest that corresponds to a disease state is compared to a second biomarker profile that corresponds to a non-disease state.

Flow Cytometry Data Analysis

In various embodiments, the systems, methods, media, and networks described herein comprise using a flow cytometry instrument (also referred to as a flow cytometer) to collect flow cytometry data. Flow cytometry is a technology for analyzing the physical and chemical characteristics of particles in a fluid that are passed in a stream through the beam of at least one laser. One way to analyze cell characteristics using flow cytometry is to label cells with a fluorophore and then excite the fluorophore with at least one laser to emit light at the fluorophore emission frequency. The fluorescence is measured as cells pass through one or more laser beams simultaneously. Up to thousands of cells per second can be analyzed as they pass through the laser beams in the liquid stream. Characteristics of the cells, such as their granularity, size, fluorescent response, and internal complexity, can be measured. An exemplary layout of a flow cytometry instrument is shown in FIG. 3.

Flow Cytometer Instruments

Flow cytometer instruments generally comprise three main systems: fluidics, optics, and electronics. The fluidic system may transport the cells in a stream of fluid through the laser beams where they are illuminated. The optics system may be made up of lasers which illuminate the cells in the stream as they pass through the laser light and scatter the light from the laser. When a fluorophore is present on the cell, it will fluoresce at its characteristic frequency, which fluorescence is then detected via a lensing system. The intensity of the light in the forward scatter direction and side scatter direction may be used to determine size and granularity (i.e., internal complexity) of the cell. Optical filters and beam splitters may direct the various scattered light signals to the appropriate detectors, which generate electronic signals proportional to the intensity of the light signals they receive. Data may be thereby collected on each cell, may be stored in computer memory, and then the characteristics of those cells can be analyzed based on their fluorescent and light scattering properties. The electronic system may convert the light signals detected into electronic pulses that can be processed by a computer. Information on the quantity and signal intensity of different subsets within the overall cell sample can be identified and measured.

Currently, flow cytometry can be performed on samples labeled with up to 17 or ≥17 fluorescence markers simultaneously, in addition to 6 side and forward scattering properties. Therefore, the data may include up to 17 or at least 17, 18, 19, 20, 21, 22, or 23 channels. Therefore, a single sample run can yield a large set of data for analysis.

Figure 4B:
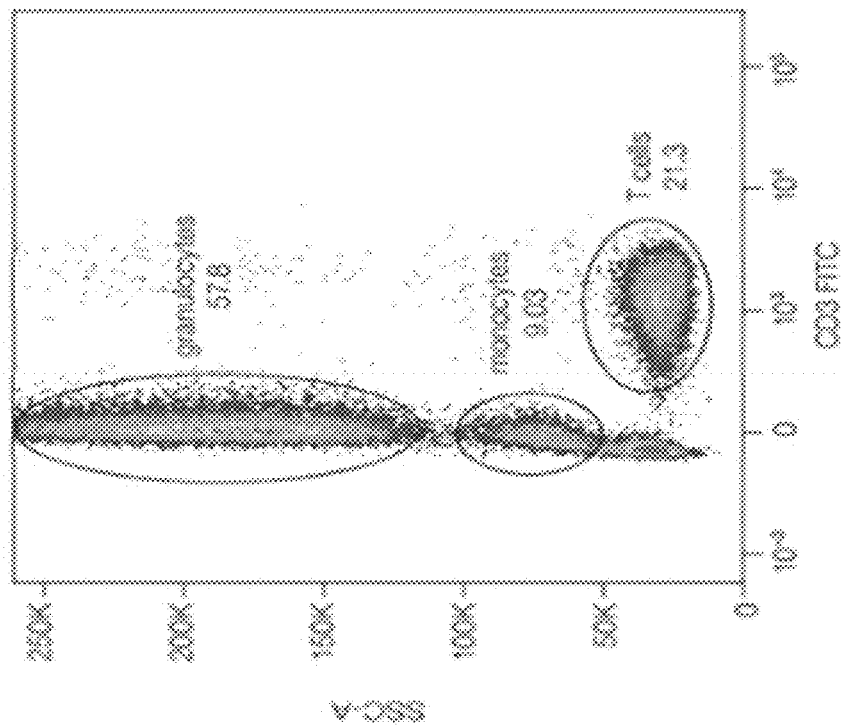
FIGS. 4A and 4B are examples of color-density flow cytometry plots. On density plots, each dot or point represents an individual cell, with increasing number of events represented by green/yellow/red colors. These reports distinguish cells based on their light scatter properties. FSC—forward scatter; SSC—side scatter; FITC—fluorescein isothiocyanate (a fluorescent label).
Figure 4A:
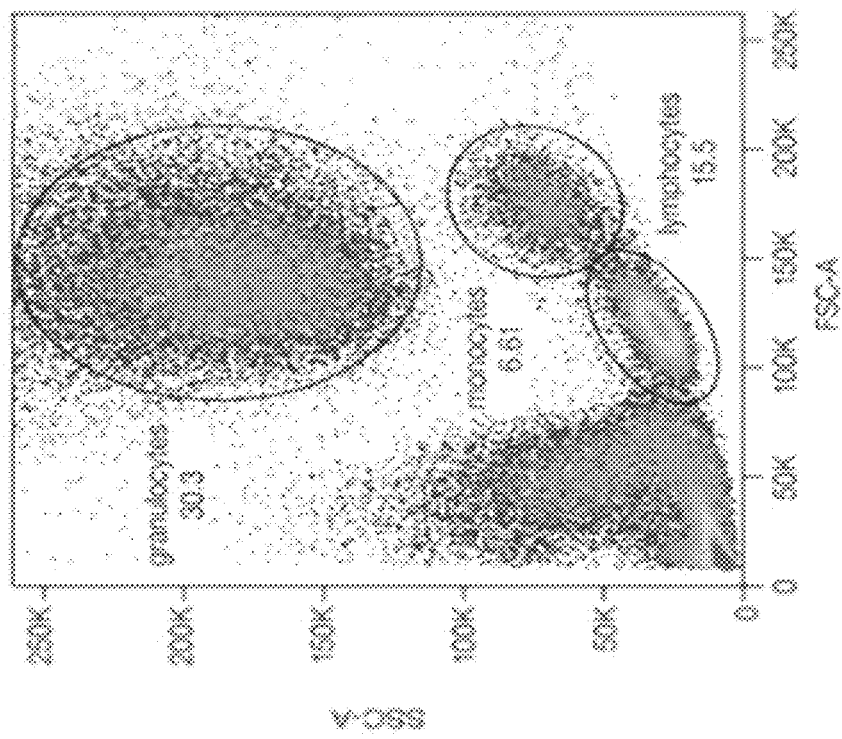

Flow cytometry data may be presented in the form of single parameter histograms or as 2-dimensional plots of parameters, generally referred to as cytograms, which display two measurement parameters, one on the x-axis and one on the y-axis, and the cell count as a cldnsity (dot) plot or contour map. FIGS. 4A and 4B show examples of 2-dimensional plots and some gates. In some embodiments, parameters are side scattering (SSC) intensity, forward scattering (FSC) intensity, or fluorescence. SSC and FSC intensity signals can be categorized as Area, Height, or Width signals (SSC-A, SSC-H, SSC-W and FSC-A, FSC-H, FSC-W) and represent the area, height, and width of the photo intensity pulse measured by the flow cytometer electronics. The area, height, and width of the forward and side scatter signals can provide information about the size and granularity, or internal structure, of a cell as it passes through the measurement lasers. In further embodiments, parameters, which consist of various characteristics of forward and side scattering intensity, and fluorescence intensity in particular channels, are used as axes for the histograms or cytograms. In some applications, biomarkers represent dimensions as well. Cytograms display the data in various forms, such as a dot plot, a pseudo-color dot plot, a contour plot, or a density plot.

The data can be used to count cells in particular populations by detection of biomarkers and light intensity scattering parameters. A biomarker is detected when the intensity of the fluorescent emitted light for that biomarker reaches a particular threshold level.

Gating

Flow cytometry data may be analyzed using a procedure called gating. A gate is a region drawn by an operator on a cytogram to selectively focus on a cell population of interest. For example, referring to FIGS. 4A and 4B, regions of interest are drawn.

Gating typically starts using the light scatter intensity properties. This allows for subcellular debris to be differentiated from the cells of interest by relative size, indicated by forward scatter. This first step is sometimes called morphology. The next step may be performed to separate out doublets and clumps of cells which are less reliable for accurate identification, leaving only the singlets. The third step in gating may select out live cells and exclude the dead or dying cells in the population. This is usually performed using a cytogram with forward scatter as the x-axis and DAPI (4',6-diamidino-2-phenylindole) staining intensity as the y-axis. DAPI stains the nucleus of the cell, which is only accessible in dead or dying cells, so cells showing significant DAPI stain may be deselected. Subsequent gating may involve the use of histograms or cytograms, repeatedly applied in different marker combinations, to eventually select only those cell populations that have all the markers of interest that identify that cell population.

Gate regions can take the form of polygons, squares, dividing the cytogram into quadrants or sectionals, and many other forms. In each case, the operator may make a decision as to where the threshold lies that separates the positive and negative populations for each marker. There are many variations that arise from individual differences in the sampled cohort, differences in the preparation of the sample after collection, and other sources. As a result, it is well known in the field that there is significant variation in the results from flow cytometry data gating, even between highly skilled operators.

Automatic Analysis

In various embodiments, the systems, methods, media, and networks described herein include using or analyzing multidimensional flow cytometry data from a flow cytometry instrument. In some embodiments, the multidimensional flow cytometry data is in at least two, three, four, five, six, or seven dimensions. The multidimensional flow cytometry data may comprise one or more of the following: forward scatter (FSC) signals, side scatter (SSC) signals, or fluorescence signals. Characteristics of the signals (e.g., amplitude, frequency, amplitude variations, frequency variations, time dependency, space dependency, etc.) may be treated as dimensions as well. In some embodiments, the fluorescence signals comprise red fluorescence signals, green fluorescence signals, or both. Any fluorescence signals with other colors may be included in embodiments.

In some embodiments, the systems, methods, media, and networks described herein include identifying a gate region in the multidimensional flow cytometry data. It is difficult to define standard operating procedures to guide human operators performing manual gating. The subjective nature of manual gating often causes bias introduced by different operators and even due to a single individual operators differing performance at different times. Automated gating minimizes the variation in gating results due to cross individual variation and performance variation over time of a single operator. Computerized algorithms for flow cytometry data analysis enables more consistent gating results than the results produced by human experts. In some embodiments, supervised algorithms are employed in an attempt to mimic manual gating decisions. Once configured, supervised gating algorithms produce results with substantially less variability than gating performed by human operators. Variation in gating results between different algorithms often exceeds 10%, so some embodiments consider ensembles of different algorithms to produce better gating results.

Artificial Neural Networks for Flow Cytometry Data Analysis

Artificial neural networks (ANNs) are a type of computational system that can learn the relationships between an input data set and a target data set. An ANN is a simplified mathematical representation of a portion of the human neural system, intended to capture its "learning" and "generalization" abilities. ANNs are a major foundation in the field of artificial intelligence. ANNs are widely applied in research because they can model highly non-linear systems in which the relationship among the variables is unknown or very complex. ANNs are trained using a data set and a target. The data set is conventionally divided into a training set, a test set, and, in some cases, a validation set. A target is specified that contains the correct classification of each sample in the data set. In particular, a type of neural network called a feed-forward back-propagation classifier can be trained on an input data set to classify input samples as belonging to a pre-defined category according to a target. The category can also refer to a disease or a condition. A set of samples from multiple categories is repeatedly presented to the ANN classifier input, and for each sample presented during training, the output generated by the ANN is compared with the desired target. The difference between the target and the set of input samples is calculated, and the ANN is modified using the back-propagation algorithm to cause the output to more closely approximate the desired target value. After a large number of training iterations, the ANN output will closely match the desired target for each sample in the input training set.

consist of symptoms, biochemical analysis, and other features such as age, sex, medical history, etc. The output will consist of the diagnosis. Some examples of the use of ANNs in medical diagnostics include (from J. Appl. Biomed. 11: 47-58, 2013 DOI 10.2478/v10136-012-0031-x ISSN 1214-0287):

| Input | Context | Output | Reference |
|---|---|---|---|
| Age, cholesterol concentration, arterial hypertension | Coronary artery disease | Diagnosis | (Atkov et al. 2012) |
| Heart sound | Valve stenosis | Diagnosis | (Uğuz 2012) |
| Hematologic profile | Chronic myeloid leukemia | Classification of leukemia | (Dey et al. 2012) |
| Cytology of effusion fluid | Carcinoma | Presence of malignant cells | (Barwad etal. 2012) |
| Electroencephalographic (EEG) recordings | Epilepsy | Prediction of seizures | (Fernandez-Blanco et al. 2012) |

Subsequently, when a new sample, not used during training, is presented to the ANN, it may generate an output classification value indicating which of the categories the new sample is most likely to fall into. The ANN is said to be able to "generalize" from its training to new, previously unseen input samples. This feature of ANNs allows them to be used to classify almost any input data which has a mathematically formulatable relationship to the category to which it can be assigned.

Figure 5A:
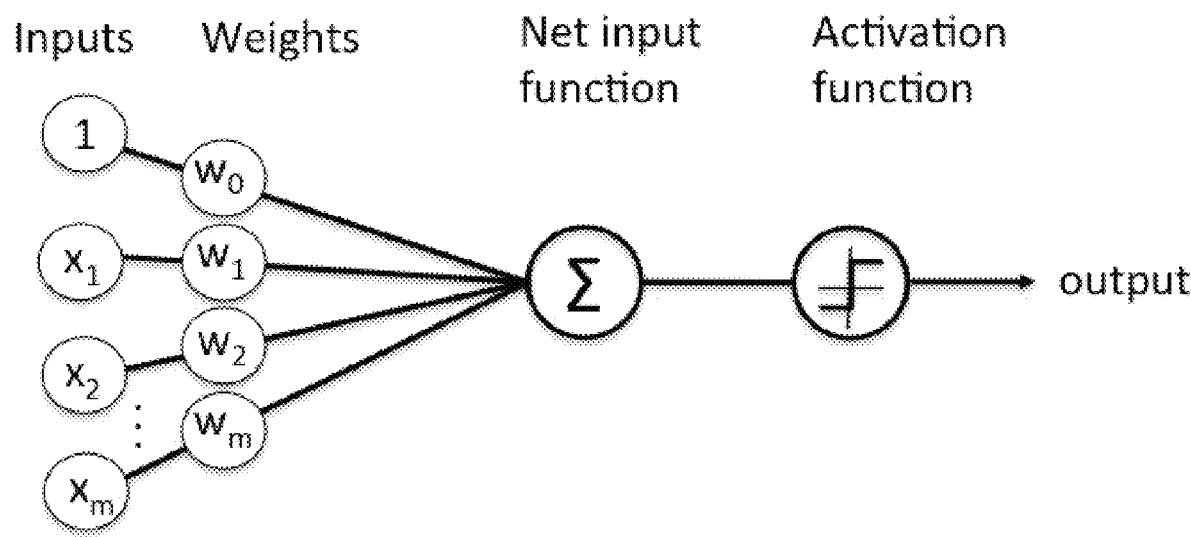
FIG. 5A illustrates an example of an artificial neuron in an artificial neural network (ANN).
Figure 5B:
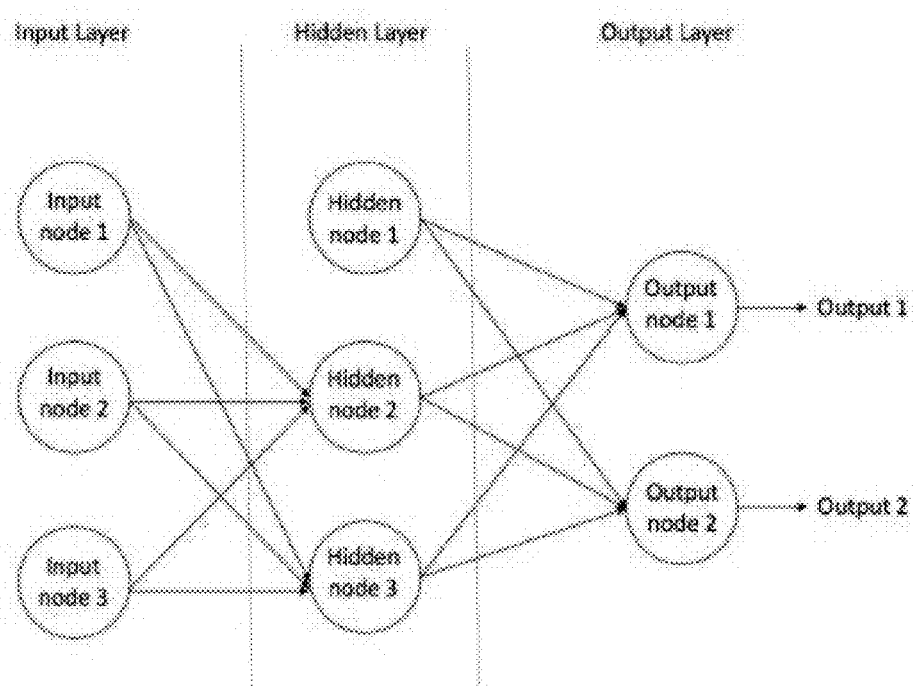
FIG. 5B illustrates an example of a simplified artificial neural network (ANN) having three layers.

A neural network is comprised of a series of layers of neurons. A typical neuron in an ANN is shown in FIG. 5A. As illustrated in FIG. 5B, there is an input layer, to which data is presented; one or more internal, or "hidden," layers; and an output layer. A neuron may be connected to neurons in other layers via connections that have weights, which are parameters that control the strength of the connection. The number of neurons in each layer may be related to the complexity of the problem to be solved. The minimum number of neurons required in a layer may be determined by the problem complexity, and the maximum number may be limited by the ability of the neural network to generalize. Excessive numbers of neurons may improve performance on the training set, but may result in poorer performance on new samples. The actual number in a specific example is generally determined through a process of trial and error, following general rules well known in the art. The input neurons may receive data from the sample being presented and transmit that data to the first hidden layer through connections weights, which are modified during training. The first hidden layer may process the data and transmit its result to the next layer through a second set of weighted connections. Each subsequent layer may "pool" the results from the previous layers into more complex relationships.

Whereas conventional software programs may require writing specific instructions to perform a function, ANNs may be programmed by training them with a known sample set and allowing them to modify themselves during training so as to provide a desired output such as a classification value. After training, when they are presented with new sample data, they can generalize what they have learned during training to be able to classify the new previously unseen data.

ANNs have been applied to a number of problems in medicine, including image analysis, biochemical analysis, drug design, and diagnostics. ANNs have recently begun to be utilized for medical diagnostic problems. ANNs have the ability to identify relationships between patient data and disease and generate a diagnosis based exclusively on objective data input to the ANN. The input data will typically In general, however, these methods use as the diagnostic input data symptoms, biochemical analysis, and other features such as age, sex, medical history, etc., which are identical to the diagnostic data used by medical professionals. Disclosed herein is a novel method that presents the unprocessed data to an ANN as features in a multidimensional space, and classifies input samples according to their distribution in that multidimensional space.

Classification by Analysis of Data Distribution in a Hypervolume

Flow cytometers output data in the form of measurements of fluorescence intensity measured for each cell for each of the fluorescence channels used in a particular flow cytometer configuration. These channel values may represent the values measured for a cell in terms of laser side scatter, forward scatter, and one or more immunofluorescent markers.

Figure 7:
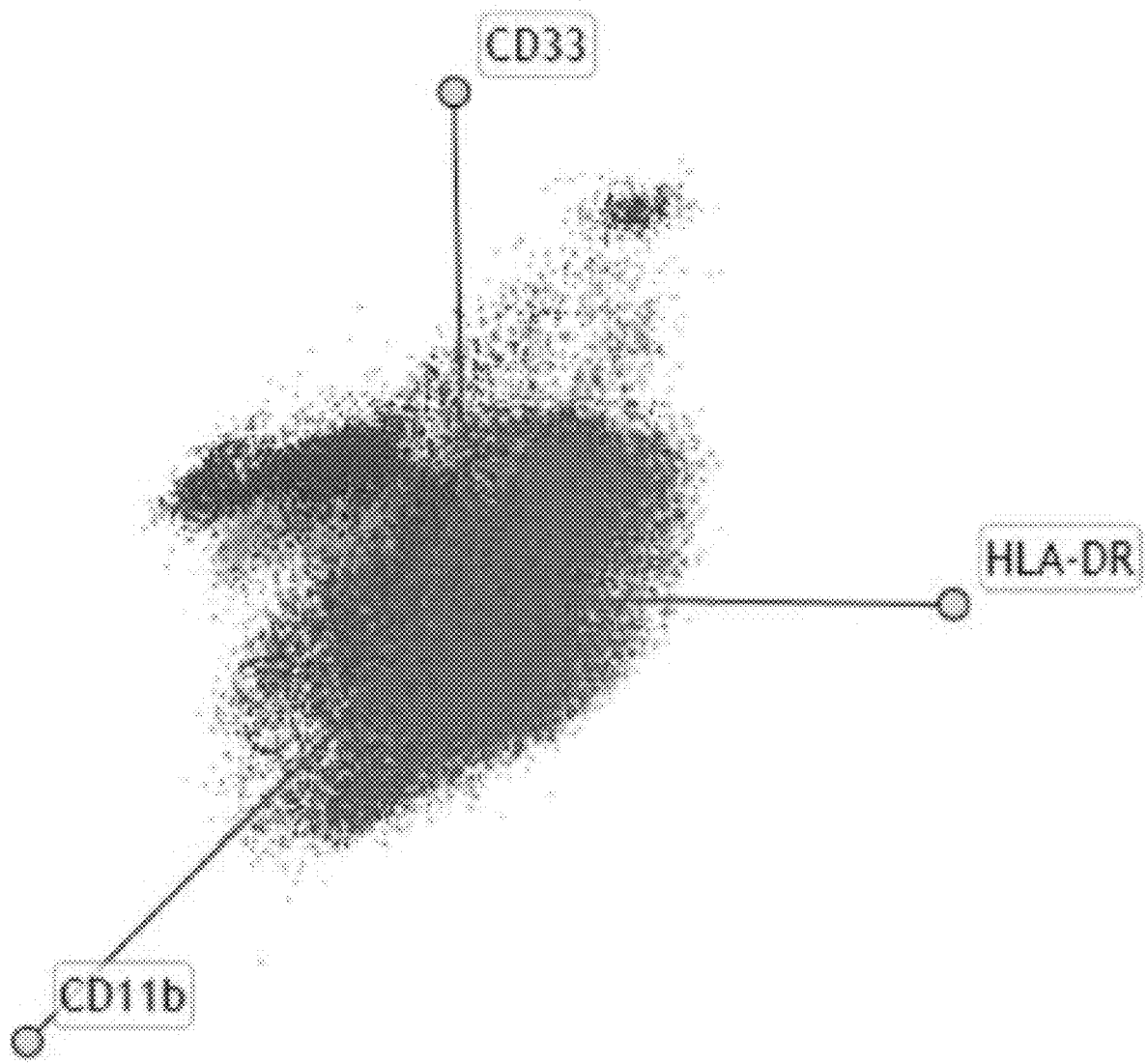
FIG. 7 illustrates an example of a distribution plot of cells marked with three biomarkers in a 3D data space.

The data produced by a flow cytometer may include a measurement in each of the flow cytometers channels for each event or cell measured. Using these measurement channel values as locations on axes defined by the various physical characteristic and fluorescent channels of the flow cytometer, each cell may have a specified location in the data space thus defined. As illustrated in 3 dimensions in FIG. 7, the cell positions in aggregate form a point cloud or clouds comprised of one or more cell populations. Similarly, cell populations having locations in higher dimensional data spaces will form distributions having higher dimensional shapes which are difficult to illustrate but are readily detectable mathematically.

A hyperspace is a coordinate space having 4 or more dimensions, each dimension having an associated coordinate axis defined by the basis vectors of the hyperspace. Each coordinate axis of a hyperspace can be sub-divided into a number of segments. The segments can be of equal length or have different lengths in different regions of the axis to enable different resolution and different size hypervoxels in different regions of the hyperspace. Different axes can have the same size segments or different size segments, which enables having different resolutions for different axes. A hyperspace can have regions which are called hypervolumes. A hypervolume can be divided into sub-volumes called hypervoxels. Each edge of a hypervoxel corresponds to a segment on one of the hyperspace coordinate axes. When a hypervolume of a hyperspace has been divided into hypervoxels, every point in that hypervolume has a location which falls into one of the hypervoxels in the hypervolume. For a point having a value for each axis of the coordinate system of a hyperspace that places that point within a hypervolume that has been divided into hypervoxels, the point will be located in a specific hypervoxel. Each channel of flow cytometry data can be used as one axis of a hyperspace that can be divided into a number of hypervoxels. In one embodiment, each axis is divided into a small plurality of segments, e.g. from 4 to 8. For example, a 3D space having 3 axes, each divided into 8 segments would have 8×8×8=512 voxels. Any point in that 3D space will be located in one of the voxels. Similarly, a hyperspace having 7 axes, each divided into 8 segments, would have $8^7$ or 2,097,152 hypervoxels, and any point in that space will be located in one of those hypervoxels. If multiple points are in the same hypervoxel, there will be a point count associated with that hypervoxel.

Flow cytometry data is generally recorded as a set of simultaneous measurements on a plurality of channels for each of a plurality (e.g., a large number) of events of interest. The events can correspond to any type of particle that can be suspended for analysis by flow cytometry. In some embodiments, a plurality of events of interest may comprise one or more cells. In some embodiments, a plurality of events of interest may be detected in a biological sample. When the events are live cells tagged with multiple antibody-fluorophore conjugates, each cell can be considered to be at a specific location in a multidimensional hyperspace where the axes of the hyperspace are the measurement channels and the location of the cell is given by the magnitude of the measurement in each channel. A count can be determined for how many cells are located in each hypervoxel. The set of all counts for every hypervoxel provides a detailed description of the distribution in hyperspace of the set of cell populations that comprised the measured sample. A neural architecture can be devised that uses as its input this set of hypervoxel counts.

Data may be presented in 2-dimensional matrix form with individual samples for training, validation, or test in columns and features presented in rows. Flow cytometry data may be exported from the flow cytometer in the form of standard format FCS files. A flow cytometry data analysis program may be used to select only live cells. This can be done manually or automatically. Flow cytometry data analysis programs that run on a PC under Windows or MacOS operating systems that are suitable and commercially available include FlowJo™ by FlowJo, LLC, FCS Express™ by De Novo Software, or Kaluza Analysis Software™ by Beckman Coulter Life Sciences.

Figure 6A:
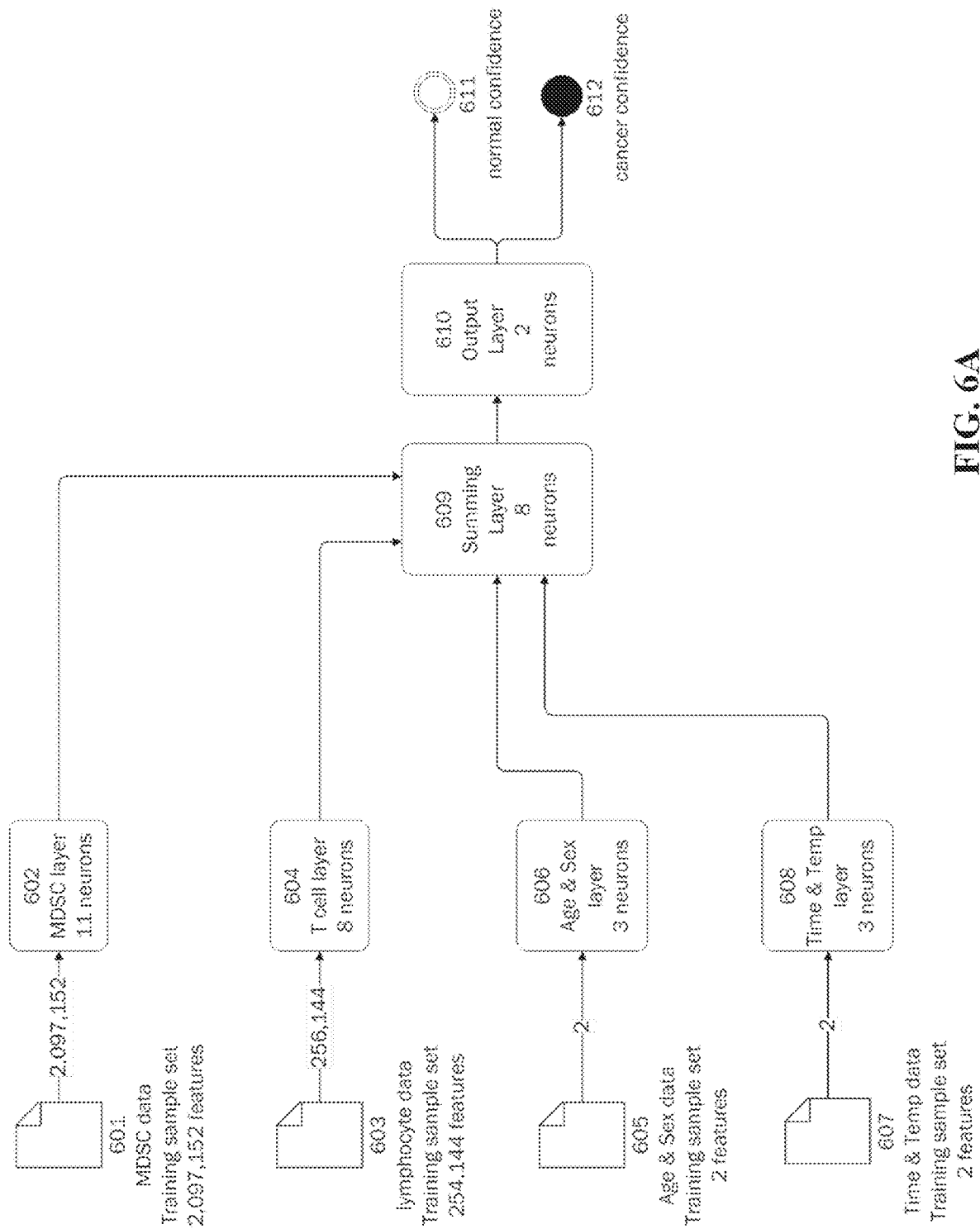
FIG. 6A illustrates an example of a primary neural network for hypervolume distribution analysis.

Multiple hyperspaces having different axes can be constructed from a sample for a single individual. For example, if a blood sample is used as the original sample source, it can be separated into a first sub-sample stained with a set of antibody-fluorophore conjugates designed to identify myeloid-derived suppressor cells (MDSCs) to produce a first populated hyperspace using flow cytometry 601, and a second sub-sample stained with a set of antibody-fluorophore conjugates designed to identify lymphocytes to produce a second populated hyperspace using flow cytometry 603. These two populated hyperspaces can be presented simultaneously to two different inputs layers 602, 604 and first hidden layers of a neural network architecture, as shown in FIG. 6A. Additional sub-samples can be stained to identify any cell population of interest, creating a plurality of hyperspaces that can be used as inputs to the neural network architecture. Additional data from sample features, including age and sex data 605 and time and temperature data 607, can presented as input layers 606, 608 to the neural network architecture. The input layers can be presented to a summing layer 609 and then to the output layer 610 of the artificial neural network to provide confidences in the classification of the sample, as normal 611 or as having cancer 612.

MDSC populations in a non-tumor-bearing donor can be elevated due to a chronic condition, but this will usually result in a simultaneous elevation in lymphocyte population. In a tumor-bearing patient, however, the elevated MDSC population will suppress the T cell population. Therefore, by allowing a neural network to have both MDSC and lymphocyte hyperspace cell population distributions available as inputs may enhance the neural network's ability to distinguish between individuals who are positive and negative for cancer.

Linear Discriminant Analysis (LDA) is commonly used as dimensionality reduction technique in the pre-processing step for neural network classification applications when there are multiple output classes, e.g., when there are a plurality of cancer types to be classified. The general LDA approach is very similar to a Principal Component Analysis, but instead of finding the component axes that maximize the variance of all samples (PCA), LDA finds the axes that maximize the separation between multiple classes, such as non-tumor-bearing subjects and tumor-bearing-subjects having various types of cancer. The goal of an LDA is to project a feature space (a dataset of n-dimensional samples) onto a smaller subspace k (where k≤n−1) while maintaining the class-discriminatory information. In general, dimensionality reduction reduces computational costs for a given classification task, but it can also be helpful to avoid overfitting by minimizing the error in parameter estimation.

Both Linear Discriminant Analysis (LDA) and Principal Component Analysis (PCA) are linear transformation techniques that are commonly used for dimensionality reduction. PCA is a "unsupervised" algorithm, since it "ignores" classes and its goal is to find the directions (the so-called principal components) that maximize the variance in a dataset. In contrast to PCA, LDA is "supervised" and computes the directions ("linear discriminants") that will represent the axes that that maximize the separation between multiple classes. It is common to use both LDA and PCA in combination, where PCA is first computed on the overall dataset for dimensionality reduction followed by LDA.

After performing PCA on the dataset, LDA is performed in five steps. First, the mean vectors m, (i=1,2) of each of the classes (non-tumor-bearing subject and tumor-bearing-subject) are computed. For 7 flow cytometer channels as axes (dimensions), this will be a 2×7 matrix whose rows are the 7 channels and whose columns are the means for each of the 7 channels. If more than two classes are to be used, for example if the artificial neural network is to be used to distinguish between non-tumor-bearing subjects and subjects who have different types of cancer, or subjects having different stages of cancer, there will be a column for each desired classification. Generally, the LDA computation proceeds as follows. The within-class scatter matrix $S_w$ is computed by the following equation:

$$S_W = \Sigma_{i=1}^c S_i$$

where the scatter matrix for every class is given by $$S_i = \Sigma_{x \in D_i}^n (x - m_i)(x - m_1)^T$$

and $m_i$ is the mean vector $$m_i = \frac{1}{n_i} \sum_{x \in D_i}^n x_k$$

The between-class scatter matrix $S_B$ is computed by the following equation:

$$S_B = \sum_{i=1}^{c} N_i (m_i - m)(m_i - m)^T$$

Where m is the overall mean, and $m_i$ and $N_i$ are the sample mean and sizes of the respective classes.

The next step is to solve the eigenvalue problem for the matrix $$S_W^{-1} S_B$$

to obtain the linear discriminants. We next select the eigenvectors thus obtained for the highest values of variance, obtaining our eigenvector matrix W, which we use to transform the original sample set into the new dataspace $$Y = X \times W,$$

where X is a matrix containing the sample data, and Y is a matrix containing the transformed samples. For each sample, all the events in the sample are thus transformed into the new dataspace. Each sample produces a transformed matrix in the same new data space. These samples are then substituted for the sample data in the raw flow cytometer dataspace, the artificial neural network is trained, and subsequent samples to be tested are transformed using the same basis vectors W.

In another embodiment, the axes of a hyperspace to be analyzed by an artificial neural network can be optimized using Discriminant Analysis of Principal Components (DAPC). DAPC is described in *A tutorial for Discriminant Analysis of Principal Components (DAPC) using adegenet 2.0.0*, Thibaut Jombart, Caitlin Collins, which is incorporated herein as reference as to this disclosure. DAPC is similar to Principal Components Analysis (PCA) in that it generates from a set of physically meaningful axes, such as the axes produced using the flow cytometer channels, a set of optimized orthogonal axes that maximize variation along an axis. DAPC differs from PCA in that PCA operates on a single population of observations, whereas DAPC operates on multiple sets of similar but differentiated populations, e.g., a non-tumor-bearing population and a tumor-bearing population, and generates a set of orthogonal axes that maximize the variation between the populations. DAPC in itself may require prior groups to be defined. However, when groups are unknown or uncertain, there is a need for identifying meaningful clusters. This can be achieved using k-means, a clustering algorithm which finds a given number (say, k) of groups maximizing the variation. In general, total variance=(variance between groups)+(variance within groups), or, denoting X as the data matrix:

$$VAR(X) = B(X) + W(X)$$

Principal Component Analysis (PCA) focuses on VAR (X). That is, it only describes the global diversity, overlooking differences between groups. On the contrary, DAPC optimizes B(X) while minimizing W(X). It finds synthetic variables, the discriminant functions, which optimizes showing differences between groups while minimizing variation within groups. DAPC in itself may require prior groups to be defined. However, groups are often unknown or uncertain, and there is a need for identifying genetic clusters before describing them. This can be accomplished using the k-means clustering algorithm which finds a set k of groups maximizing the variation between groups, B(X). To identify the optimal number of clusters, k-means is run sequentially with increasing values of k, and different clustering solutions are compared using Bayesian Information Criterion (BIC). Before running k-means, the data is transformed using conventional PCA. This transformation reduces the number of variables thereby speeding up the clustering algorithm. After determining the optimal principal components for maximizing group differences between a training set of samples from non-tumor-subjects and samples from tumor-bearing subjects, the samples observations can be mapped from their original coordinates to the DAPC derived group-difference-maximization DAPC principal components, thereby providing an optimized input data space on which to train the artificial neural network. Similarly, test samples can be mapped into the DAPC-derived principal components before being submitted to the trained artificial neural network for testing.

In one embodiment, Kernel Linear Discriminant Analysis (KLDA) is used to pre-process sample information to enhance distinctions between different classes of samples such as the non-tumor-bearing test subject class (normal) and the known cancer patient class (cancers). If two sample classes are not readily distinguishable by a linear classifier, KLDA first transforms the sample data by use of a kernel into a higher dimension space where it is possible to linearly distinguish between the populations and then reduce the dimensionality of that space into a reduced dimension space where the axes are the eigenvectors with the highest eigenvalues (principal components) with the highest variance between classes. First, the original labeled training data set X is loaded:

$$X = \{n\_samples, m\_features, C\ classes\}$$

For each class, the pairwise squared Euclidean distance is calculated in X to create a pairwise distance vector $d_{pairwise}$. Each pairwise distance vector $d_{pairwise}$ is then converted into a square matrix of pairwise distances $X_{sq\_dists}$ (1:n classes). Next, a symmetric kernel matrix is computed for each $X_{sq\_dists}$.

The kernel chosen depends on the nature of the data set. The most common kernels are the polynomial kernel, the hyperbolic tangent (sigmoid) kernel, and the Radial Basis Function (RBF) kernel. In one embodiment, the RBF kernel is selected:

$$K = e^{(-\gamma \times X_{sq\_dists})}$$

The kernel matrices are then centered:

$$K_{centered} = K - 1_n K - K 1_n + 1_n K 1_n$$

Where $1_n$=an n×n where all values are 1/n.

Next, for each class compute the eigenvectors of $K_{centered}$ and their eigenvalues:

$$K_{centered}\ \text{eigenvector, eigenvalue pairs} = (e_1, \lambda_1, e_2, \lambda_2, \ldots e_d, \lambda_d)$$

Then, for each class, sort the eigenvectors by decreasing eigenvalues and choose d eigenvectors with the largest eigenvalues to form a d×d square matrix $W_{d \times d}$ for each class (where each column represents an eigenvector). Use $W_{d \times d}$ to transform the samples onto the new subspace. This can be summarized by the equation:

$$x' = W_{d \times d}^T \times x$$

Where x is a d×1 dimensional vector representing one sample, and x' is the transformed d×1 dimensional sample in the new dataspace.

Having transformed the sample data for all the classes into a higher dimensional data space, we next proceed as in non-kernelized LDA to find the optimum reduced data space in which to present the data. Proceeding with the calculation, we compute the d-dimensional mean nivectors for each class (i.e., the means for every dimension of the data set for each class). These means will then be used to compute the within-class and between-class scatter matrices. The within class scatter matrix is given by:

$$S_W = \sum_{i=1}^{C} S_i$$

Where the within-class scatter matrix for each class is given by $$S_i = \Sigma_{x' \in D_i}{}^n (x'-m'_i)(x'-m'_i)^T$$

And the between-class scatter matrices are given by $$S_B = \Sigma_{i=1}^{C} N_i (m'_i - m')(m'_i - m')^T$$

Where m' is the overall mean, and m'$_i$ and N$_i$ are the sample mean and sizes of the respective classes. Then, the generalized eigenvalue problem is solved for the matrix given by $$S_W^{-1} S_B$$

The resulting eigenvectors are sorted by decreasing eigenvalues, and the k eigenvectors with the largest eigenvalues are selected, where k<d, to form the eigenvector matrix, wherein every column is an eigenvector. The eigenvector matrix W is then used to transform the original sample set into the new dataspace $$Y = X \times W$$

This transformed data space can then be populated with events to produce a hypervoxel data distribution which can be used to train an artificial neural network to distinguish between the labeled classes.

When new samples are to be tested, they can similarly be transformed into data space thus derived and tested by the artificial neural network.

In some embodiments, the individual hyperspaces generated from separate flow cytometer measurements can be combined to allow the neural network to more readily compare cell population distributions measured with different stain sets. For example, a MDSC measurement hyperspace may have 7 axes, each divided into 8 segments. This produces $8^7$ (2,097,152) hypervoxels, which is a large but not computationally intractable amount of data. A lymphocyte measurement hyperspace may have 6 axes, each divided into 8 segments. This produces $8^6$ (262,144) hypervoxels. One of the axes (SSC-A) may be used in both hyperspaces, leaving 12 unique axes. Since $8^{12}$ is equal to approximately $6.87^{10}$, this may require far more processing power and memory than the two individual hyperspaces processed individually. To mitigate this problem, dimensionality reduction can be performed. In some embodiments, the systems, methods, media, and networks described herein comprise performing a dimensionality reduction algorithm. Dimensionality reduction can be performed at any time during the analysis. In some embodiments, dimensionality reduction is performed at the beginning of the analysis. In some embodiments, dimensionality reduction is performed at a middle step of the analysis.

One method of dimensionality reduction is Principal Component Analysis (PCA). PCA identifies linearly independent axes, in order of decreasing variability, that can be substituted for the original axes. The axes with variability below a selected threshold can be discarded, resulting in a smaller hyperspace dimensionality while still retaining the majority of the information present in the cell distribution and hypervoxel counts. Thus, for example, the unique MDSC hyperspace axes can be reduced from, e.g., 6 dimensions to 4, and the lymphocyte hyperspace unique axes reduced from 5 to 4, resulting in a 9-dimension hyperspace containing both lymphocyte counts and MDSC counts in the same space. If the resolution is reduced from 8 divisions per axis to 5, the total number of hypervoxels in this space will be $5^9$ (1,953,125) which is more computationally tractable.

Figure 15A:
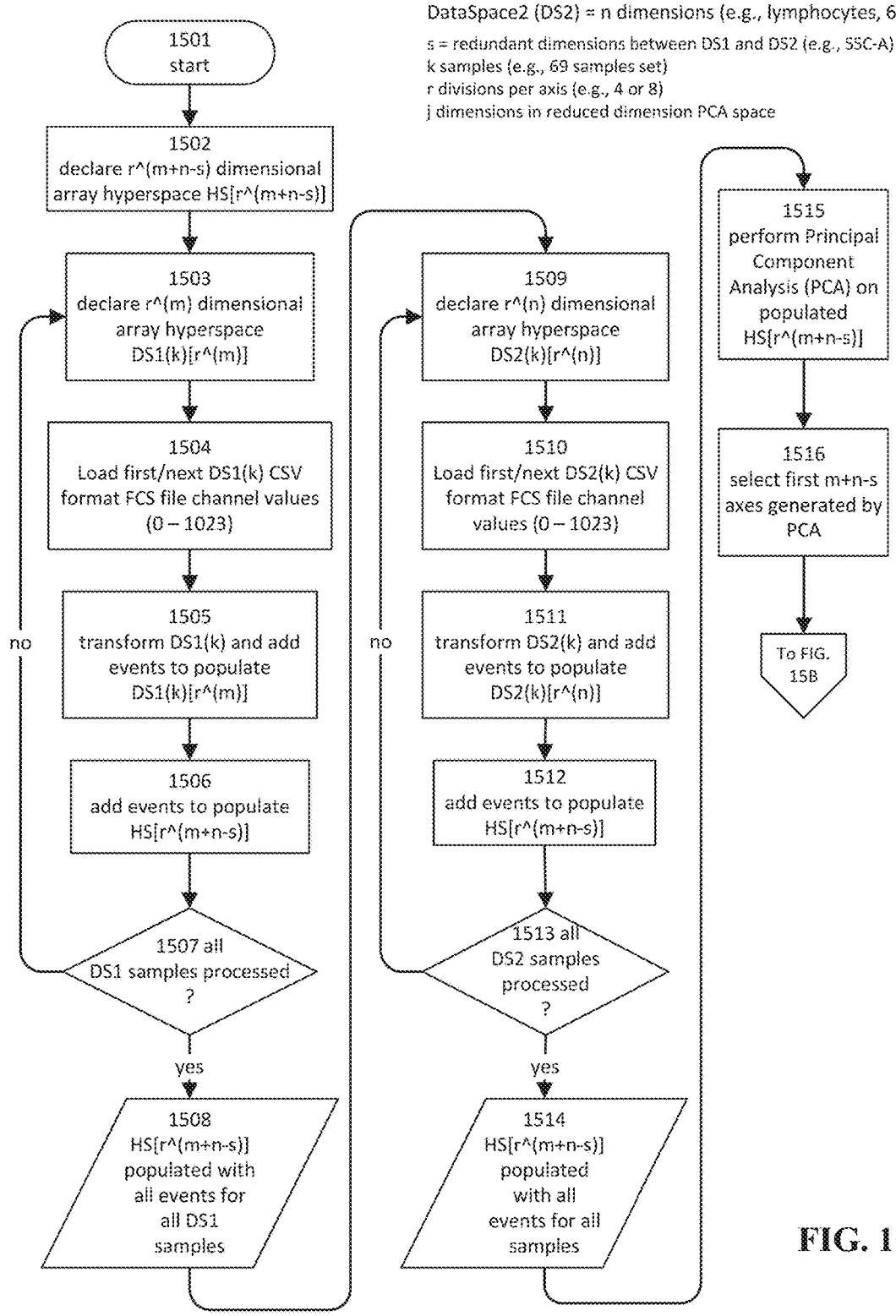
FIGS. 15A and 15B illustrate a dimensionality reduction of hypervoxel dataspaces derived from flow cytometry data.
Figure 15B:
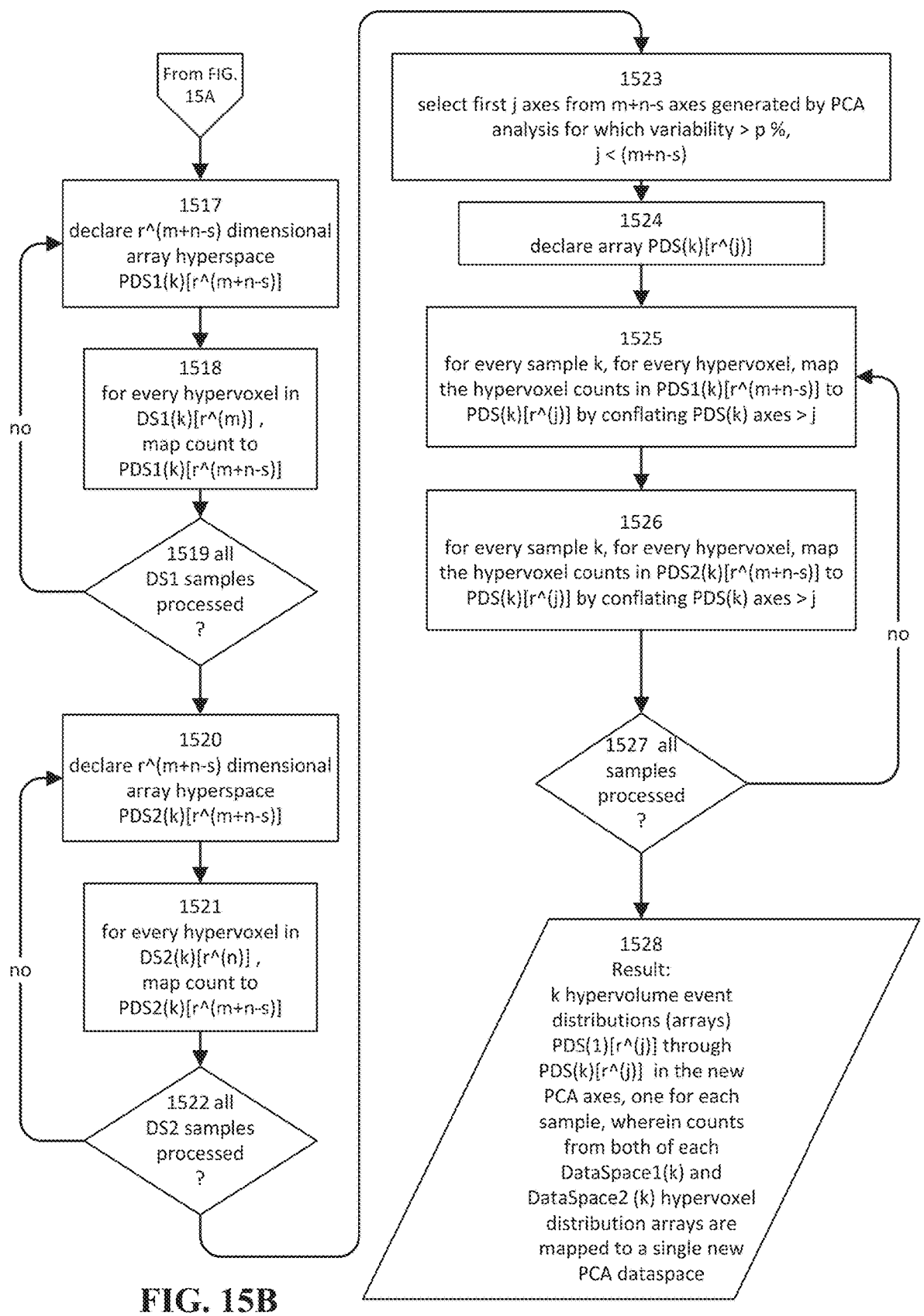

FIGS. 15A and 15B illustrate dimensionality reduction on a combined population of two sets of flow cytometry data to allow an ANN to directly compare the relationship of the two populations in a single data space that would be intractably large if the dimensions of the two data spaces were simple concatenated. At the start 1501 of the dimensionality reduction process, an array $HS[r^{(m+n-s)}]$ is declared 1502 to contain the hypervoxel count distributions from two combined dataspaces. $HS[r^{(m+n-s)}]$ is of dimension m+n−s, where m is the number of dimensions of the first dataspace to be combined, n is the number of dimensions of the second, dataspace to be combined, and s is the number of redundant dimensions, i.e., those dimensions which appear in both data sets. In the case of MDSC and lymphocyte dataspaces, only SSC-A is used in both dataspaces, and s=1. The first dataspace DS1 may be, for example, an MDSC dataspace having 7 dimensions, including one physical measurement (SSC-A) and 6 fluorescent channel measurements. For each of k samples in the DS1 dataspace having m dimensions, a dataspace $DS1_k[r^m]$ is declared 1503. The sample, having previously been reduced to the selected m columns, is loaded 1504. The individual event values in the $k^{th}$ sample in the DS1 dataspace are used to populate the hypervoxels in the $DS1_k[r^m]$ dataspace 1505, which is saved. The values in the $DS1_k[r^m]$ populated dataspace are also entered in the corresponding hypervoxel in the $HS[r^{(m+n-s)}]$ 1506. A check is performed to determine whether all of DS1 samples have been processed 1507, and steps 1503-1506 are repeated is not all of the DS1 samples have been processed while the process proceeds to step 1508 if all of the DS1 samples have been processed. For the 1 through k samples, a separate $DS1_k[r^m]$ dataspace is declared, populated, and saved, and the samples hypervoxel counts in the $DS1_k[r^m]$ are added to the corresponding hypervoxel in the $HS[r^{(m+n-s)}]$ dataspace 1508. At the conclusion of this procedure there are k+1 dataspaces, the k $DS1_k[r^m]$ individual sample hypervoxel count dataspaces and one $HS[r^{(m+n-s)}]$ hypervoxel count dataspace.

A similar procedure 1509-1514 is followed for a second dataspace DS2, which may, for example, be a lymphocyte sample set having flow cytometry data from the same k samples and being represented in n dimensions, where n is, for example, 6 dimensions, including one physical measurement (SSC-A) and 5 fluorescent channel measurements. At the conclusion of these steps, the combined dataspace HS $[r^{(m+n+s)}]$ is populated with hypervoxel counts from all k samples in the first dataspace and all k samples in the second data set.

Principal Component Analysis (PCA) is performed 1515 on the combined dataspace $HS[r^{(m+n-s)}]$ and the first m+n−s PCA generated basis vectors are retained 1516. By performing PCA on the combined total dataset, we obtain the PCA basis vectors which define the axes of maximum variability for the entire dataset. Turning to FIG. 15B, a new array $PDS1_k[r^{(m+n-)}]$ 1517 is declared for each sample in DS1. These arrays will use the PCA basis axes just generated and will be used when combining the hypervoxel counts mapped from the two source dataspaces into a combined array per sample using the new basis vectors. For each sample in DS1, the hypervoxel counts in that samples original axes hypervoxel distribution array $DS1_k[r^m]$ are mapped to the corresponding hypervoxel in $PDS1_k[r^{(m+n-s)}]$ 1518. After all the k samples in DS1 have been mapped 1519, a similar procedure is followed for DS2 1520-1522. At the conclusion of this process, we obtain 2×k hypervoxel count distributions in the PCA derived basis vectors, one for each sample in each dataspace.

The first j basis vectors are selected from the m+n−s PCA derived basis vectors 1523. To achieve dimensionality reduction, j can be less than m+n−s.

Declare array $PDS_k[r^{(j)}]$ 1524 to be used to combine the two dataspaces using the PCA derived basis vectors. For every sample k in DS1, for every hypervoxel, map the hypervoxel counts in $PDS1_k[r^{(m+n-s)}]$ to $PDS_k[r^{(j)}]$ conflating $PDS_k$ axes >j 1525. For every sample k in DS2, for every hypervoxel, map the hypervoxel counts in $PDS2_k[r^{(m+n-s)}]$ to $PDS_k[r^{(j)}]$ by conflating $PDS_k$ axes >j 1526. A check is performed to determine whether all samples have been processed 1527, and steps 1525-1526 are repeated is not all samples have been processed while the process proceeds to step 1528 if all samples have been processed. The result obtained 1528 will be k hypervolume event distributions (arrays) $PDS_1[r^{(j)}]$ through $PDS_k[r^{(j)}]$ in the new PCA axes, one for each sample, wherein counts from both of each $PDS1_k[r^{(m+n-s)}]$ and $PDS2_k[r^{(m+n-s)}]$ hypervoxel distribution arrays are mapped to a single new reduced dimensionality dataspace $PDS_k[r^{(j)}]$ using the PCA derived basis vectors.

The dimensionality reduction and dataspace combination described in the example above combines two dataspaces, but any number can be combined using a similar procedure.

This combined hyperspace can be input to the neural network as a third input, in addition to the original MDSC and lymphocyte hyperspaces, thereby allowing the neural network to have access to the full-resolution MDSC and lymphocyte hyperspaces and have access to a synthesized hyperspace optimized for comparing the population distributions of the MDSC and lymphocyte populations.

PCA can also be used to transform the representation of a single hyperspace to ensure that the data is represented in a coordinate system wherein the axes are linearly independent (e.g., a coordinate space). This will minimize redundant information, providing the neural network with a clearer signal and thereby improving neural network performance.

Bins Filter

The events collected by the flow cytometer can be grouped into a plurality of groups according to their channel values, hereinafter referred to as bins, each bin representing a sub-population associated with a specific range of measured channel values. Since the neural network can be used to analyze many of the event channels and each event channel can contain a wide range of values, the number of possible bins can be extremely large. In a non-limiting example, if nine channels are used by the neural network and each channel is divided into four ranges then the number of possible bins is 4 raised to the ninth power, or 262,144. It is recognized that as the bins become populated with the event data some bins will remain empty while others will be populated with non-useful data (e.g., cell fragments, protein debris, etc.). It is therefore desirable to apply a filter selecting only certain bins to be analyzed by the neural network. Filtering may select for bins with useful event data (e.g., cell event data). Filtering may eliminate non-useful data and improve the neural networks efficiency at learning and classifying patient data. An advantage of this method is that the number of bins retained for analysis can be reduced by approximately 90%, thereby greatly reducing training time for the neural network. In some embodiments, the number of bins can be reduced by at least 90%, 80%, 70%, 60%, or 50% by filtering as compared to total number of bins without filtering. Applying filters to select for desired bins while discarding undesired bins is computationally more efficient and less computationally expensive because of the reduction in the number of features applied to the neural network for training and testing.

Flow cytometers typically output channel data as a value between 0 and 1023 indicating the intensity of an event in that channel. This output data may represent measurements of fluorescence intensity measured for each event for each of the fluorescence channels used in a particular flow cytometer configuration. These channel values may represent the values measured for the event (often a cell) in terms of laser side scatter, forward scatter, and one or more immunofluorescent markers. The data may be in the form of a matrix, wherein each row represents a single event, often a fixed or live cell, and each column is a flow cytometer channel. A single event, such as a target cell measured by the flow cytometer, may be represented by a single row and may have a value in each of the channels being used for that test. When each channel is used as an axis in a hyperspace, the target cell may have a defined location in a specific hypervoxel in that space. If other target cells have similar measured values for each of the flow cytometer channels, they may be located in the same hypervoxel. The number of cells located in each hypervoxel can be counted and the set of all counts of all cells in each hypervoxel can be interpreted as a distribution of cell populations in a hyperspace.

In some embodiments, up to 13 measurements are taken, which include values for forward scatter area, height, and width, which are measures of cell size; side scatter area, height, and width, which are measures of cell granularity or complexity; and measurements of seven additional laser frequencies which, in some embodiments, are measurements of immunofluorescent response of 7 antigen-immunofluorescent conjugates which bind to specific complexes of differentiation (CDs) on the surface of the cells under measurement. A summary of the data dimensions is listed below.

1 FSC-A: Forward scatter area
2 FSC-H: Forward scatter height
3 FSC-W: Forward scatter width
4 SSC-A: Side scatter area
5 SSC-H: Side scatter height
6 SSC-W: Side scatter width
7 CD11b Complex of differentiation expressed on the surface of many leukocytes including monocytes, neutrophils, natural killer cells, granulocytes and macrophages.
8 CD14 expressed mainly by macrophages and (at 10-times lesser extent) by neutrophils.
9 HLA-DR (Human Leukocyte Antigen—antigen D Related) MHC class II cell surface receptor encoded by the human leukocyte antigen complex.
10 CD33 expressed on cells of myeloid lineage.
11 Lineage combination of CD3, CD19, and CD56 markers for marking T cells, B cells, NK cells, and their precursors.
12 DAPI (4',6-Diamidino-2-phenylindole dihydrochloride) is a cell permeable, fluorescent dye that binds to DNA. Used for DNA staining in agarose gels and analysis of changes in DNA during apoptosis.
13 CD15: The CD15 antibody recognizes the CD15 antigen which is expressed on human myelomonocytic cells. It is present on neutrophils, eosinophils, and some monocytes, but not on basophils or lymphocytes.

Other markers may be used, but the above set is described for purposes of illustration of this method. Measurements of each channel are made using a photo sensor in the flow cytometer instrument. The output of the photo sensor is an electrical impulse whose amplitude and duration are measured by an analog to digital converter (ADC). The ADC information is processed to yield a value from 0 to 1023 ($2^{10}$ possible values) for each channel. Each cell yields 13 such channel measurements. The data values are then compensated to account for "cross-talk" or "bleed-over" between the different channels. In a flow cytometer, the appropriate ranges of excitation and emission wavelengths are selected by bandpass filters. However, when emission spectra overlap, fluorescence from more than one fluorophore may be detected. To correct for this spectral overlap, a process of fluorescence compensation is used. This ensures that the fluorescence detected in a particular detector derives from the fluorophore that is being measured.

The 13-compensated channel data is exported from the flow cytometer in a data file in the standard FCS file format, which contains the channel data for each event measured by the flow cytometer and configuration and setting data for the sample measurement. Not all events are cells, as many events consist of cell fragments, dead cells or portions thereof, and other debris.

In one embodiment, the flow cytometry data analysis technician begins gating by displaying the data for all events on a 2-dimensional dot plot where the forward scatter area (FSC-A) is used as the X or horizontal axis and the side scatter area (SSC-A) is used for the Y or vertical axis. Larger objects will appear on the plot farther to the right, and more complex or granular objects will be located towards the top of the plot. A "comma" shaped polygon drawn by the technician manually, or generated automatically by custom computer software is used to gate the events, excluding small, non-granular debris, lysed red blood cells, and cell fragments. In one embodiment, this is referred to as the "Morphology" gate.

The events thus gated for morphology are extracted and displayed on a second plot, the "Singlets" plot. The Singlets plot again has FSC-A for the X axis, but the forward scatter height (FSC-H) is used for the vertical axis. As is well known in the art, single cells will have similar area and height signals, as they are generally spherical. They will therefore be found near a line on the plot starting at the origin and projecting therefrom at a 45° angle. Cell doublets (two cells adhering to one another) and larger clumps of cells will be displaced from this 45° line because they have dis-similar dimensions. A polygonal gate is drawn around the 45° line, including single cells and excluding doublets and clumps.

The single cells are then extracted using the Singlets gate, and displayed on a third plot, the "Live-dead" plot. The Live-dead plot again uses FSC-A for the X axis, and uses the DAPI channel signal for the Y axis. DAPI is a fluorescent stain used to stain DNA in cell nuclei. In live cells, the cell membrane remains intact and the DAPI stain may not penetrate to stain the nuclear DNA. Therefore, on the Live-dead plot, live cells will be located along the bottom of the plot due to their low (essentially nonexistent) DAPI take-up. A rectangular gate encompassing the live cells is drawn manually by the technician or generated automatically by custom computer software.

This group of cells, the "Live" group, having been gated (selected) for morphology, singlet, and live, is then exported as a matrix or spreadsheet, in a standard format such as comma separated variable (CSV), as a single file having columns representing flow cytometer channel values from 0 to 1023, wherein each row represents all the measured values for a single live cell event.

In one embodiment, the sample volume and flow cytometry settings are adjusted to yield at least 40,000 live cell readings for each sample.

Each file is then either truncated to take the first 40,000 rows (i.e., live cell events) or 40,000 events are selected randomly from a larger set, if available.

In some embodiments, manual or automated gating would continue past the Live gate. The population of Myeloid-Derived Suppressor Cells (MDSCs) includes three sub-populations: (1) e-MDSCs (early-stage MDSCs), (2) PMN-MDSCs (polymorphonuclear MDSCs), and (3) M-MDSCs (monocytic MDSCs). Each such sub-population can be isolated by subsequent gating steps, as is well known in the art and is conventionally performed regularly in studies of MDSC populations. For example, e-MDSCs can be isolated by displaying the live cell population on a plot having the Lineage marker as its X-axis and the CD14 marker as its Y-axis. The population in a quadrant (Lineage marker negative and CD14 marker negative) may be selected by gating, then displayed on a subsequent plot, for example FIG. 7 having the HLA-DR marker as the X-axis, CD11b as the Y-axis, and CD33 marker as the Z-axis. The population in the lower right of this last plot may be the eMDSC population.

Similarly, the PMN-MDSC population can be isolated by plotting the Live cell population on a plot having SSC-A on the X axis and CD14 on the Y axis. Cells negative for CD14 may be selected by gating and then displayed on a plot where CD33 is used for the X axis and CD11b is used for the Y axis. The population displayed in the upper right quadrant of this plot may be selected with a polygon gate, then extracted and displayed on a final plot having CD15 as the X axis and SSC-A as the Y axis. The PMN-MDSC population may be displayed in the middle right of this plot.

Similarly, the M-MDSC population can be isolated by plotting the Live cell population on a plot having HLA-DR as the X axis and CD14 as the Y axis. The M-MDSC population will be displayed in the upper left quadrant.

In some studies that attempt to quantify the level of cells in the MDSC population and sub-populations, the gated eMDSC, PMN-MDSC, and M-MDSC cell populations are counted, and these cell populations are recorded as, for example, percentages of live cell populations. The three values of cell counts may be used as a triplet to indicate the MDSC cell population status of the patient or non-tumor-bearing sample being measured. Differences between the cell population counts between normals (i.e., non-tumor-bearing subjects) and cancer patients (i.e., tumor-bearing subjects) at various stages of cancers may be interpreted as an indication of the cancer status of the individual under test. FIGS. 2A through 2C show that there is indeed a trend, but the distributions overlap and make it difficult or impossible to distinguish between non-tumor-bearing subjects and tumor-bearing subjects using conventional gating alone.

As can be seen from the above description of conventional gating, it can be considered to be essentially a series of projections from a multidimensional data structure to a 2-dimensional "silhouette" of the distribution of the cell population in a 13-dimensional space whose axes are the channels measured by the flow cytometer. This can be readily seen by considering that if only three channels were measured, for purposes of example CD14, CD15, and CD33, each cell could be represented at a position in 3-dimensional (3D) space where the x axis corresponded to the CD14 channel value, the y axis corresponded to the CD15 channel value, and the z axis corresponded to the CD33 value. Different cell populations having different average values of the markers may cluster in 3-dimensional "point clouds" in this 3-dimensional space. The true values in 3-space could then be projected onto a series of 2-dimensional "dot plots", which would be silhouettes of the true point cloud. Any combination of two of the three values could be selected for the 2-dimensional axes, such as CD14 vs CD15, CD14 vs CD33, or CD15 vs CD33. Each such projection would provide one view of the data, just as if a 3-dimensional object was photographed from the front, the side, and the top. It can be seen, however, that information is lost in this procedure. The three photographs would not disclose whether there was structure on the bottom of the object.

Conventional gating of flow cytometry data is analogous to taking 2-dimensional "snapshots" of data distributions having much higher dimensionality. The present subject matter utilizes the premise that additional information may be derived from the flow cytometry data if the data is used simultaneously and if a data representation is used that will preserve structure in the cell population distribution in a higher dimensional space.

In some embodiments, the data is represented in an array that records the number of cells in each voxel of the higher dimensional space. In some embodiments, the data comprises a plurality of event features (i.e. cell characteristics) for each of a plurality of events of interest (i.e. cells) of the biological sample from a flow cytometer instrument.

Figure 8A:
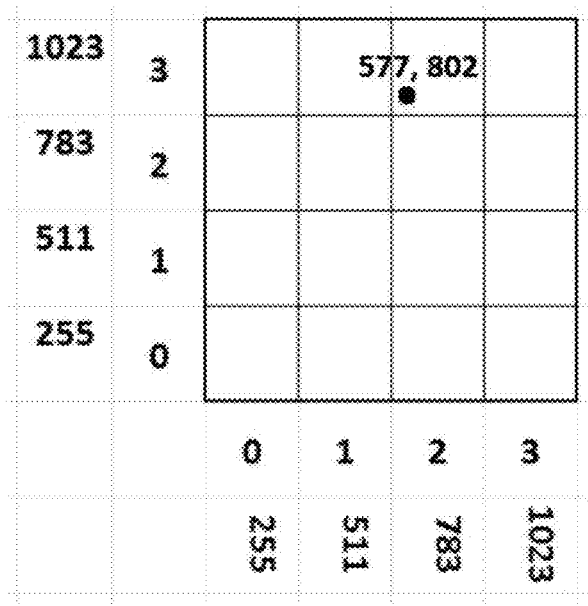
FIG. 8A illustrates an example of a cell event location in 2 dimensions.
Figure 8B:
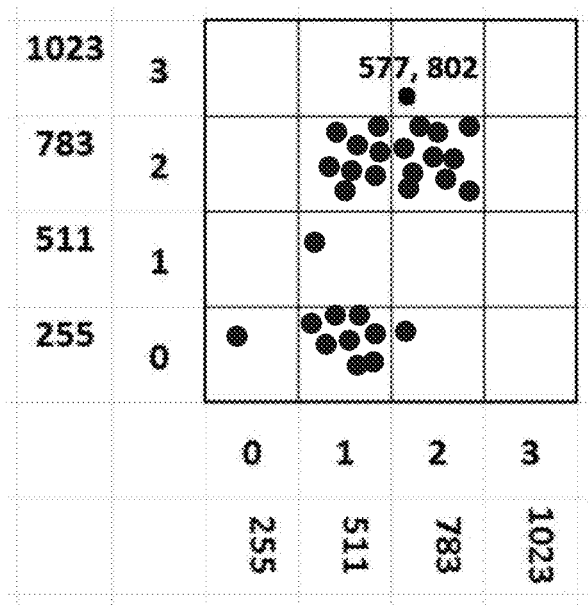
FIG. 8B illustrates an example of a cell event distribution in 2 dimensions.

The method can be demonstrated starting with a 2-dimensional plot, and 100 cell events all from the same non-tumor-bearing or tumor-bearing sample under test. Assume we have 5 non-tumor-bearing subjects and 5 tumor-bearing subjects, each of whom has contributed 100 cells. Assume the x-axis has the HLA-DR marker values from 0 to 1023, and the y axis has the CD14 marker values, again from 0 to 1023. For purposes of illustration, we will then divide the plot area into 4 by 4 (or 16) regions by dividing each axis into 4 divisions. On each axis, the first segment is from 0 to 255, the second is from 256 to 511, the third is from 512 to 783, and the fourth is from 784 to 1023. The regions are named HLA-DR 0 through HLA-DR 3, and CD14 0 through CD14 3. Assume there is a count variable, initialized at zero, associated with each of the 16 regions which represents how many cell measurement events will be located in that regions as can be determined by dividing the cell event's channel value by 256 and using the integer part of the result. As an example, consider a cell event having values of 577 for the HLA-DR (x) axis and 802 for the CD14 (y) axis. After dividing the channel values by 256 and taking the integer parts, the cell event will be located in the [2, 3] region as shown in FIGS. 8A and 8B.

Referring again to FIGS. 8A and 8B, we will add an increment of one count to the variable representing the count of all the cell events that lie in the [2, 3] region. This procedure is repeated for every cell event, at the end of which we have our 100 cell events represented by a count value associated with each of the 16 regions. The sum of all those counts will be 100. Specifically, we do not sum the values of the cell events in a particular region; rather, we simply count up the number of cells that have channel marker values that place them in that region. Regions in the centers of the point clouds will have high count values, and other regions will have counts of zero, if no cell events would plot in those regions.

After we have processed all 100 cells, we then transform our 2-dimensional 4×4 matrix of values into a 1-dimensional 16×1 column vector, where each of the tumor-bearing or non-tumor-bearing samples is represented by one column. After aggregating all 10 of the 16×1 column vectors, each row of the matrix represents a feature common across all 10 non-tumor-bearing/tumor-bearing samples, which is how many cells fell into that particular voxel for each non-tumor-bearing/tumor-bearing sample. For example, if we transpose the 4×4 count matrix into a 16×1 count vector by shifting the second column under the first, the third under the second, and the fourth under the third, the counts for each non-tumor-bearing/tumor-bearing samplethat would have fallen into the [2, 3] region will be found in the $9^{th}$ row.

We now have a representation of our 2-dimensional data distribution across our 10 samples in a 16×10 feature row vs sample column representation, which is a canonical representation for many neural network architectures and training functions.

Similarly, additional dimensions for additional channel markers, forward scatter, and side scatter channel values can be added. For example, if 7 channels were chosen, and the 4×4 resolution was retained, a 4×4×4×4×4×4×4 7-dimensional hypervolume can be transformed into a 16,384-row column vector, with each row representing the count of cell events that fell in the hypervoxel represented by that row. Also, resolution can be specified for each axis independently. For example, CD14 and CD33 may only require high vs low values to provide sufficient resolution, therefore only requiring 2 divisions of resolution along the CD14 and CD33 axes, whereas HLA-DR may require 8 divisions to provide sufficient resolution. Such a hypervolume with 8×2×2×4×4×4×4 dimensions can be transformed into an 8,192-row column vector. The appropriate number of dimensions to use, and the resolution required for each dimension, can be customized to meet the requirements of a particular analysis problem. The resolution on an axis can be coarse for part of the axis, and fine for another part, to maximize resolution in regions of interest without requiring the entire axis to have fine resolution. An axis may accept cell counts only over a section of the axis, if there is no interest in counting the number of cells having values that lie outside a particular range. The divisions can be located arbitrarily, to fit the requirements of a particular analysis.

The feature row by sample column matrix can then be used to train a neural network to distinguish between the non-tumor-bearing/tumor-bearing samplebased on the distribution in hyperspace of their cell populations. Features of the cell population distribution that are obscured or invisible using conventional gating can be utilized by the neural network to assist in classification if they show a systematic difference between non-tumor-bearing/tumor-bearing sample.

Figure 16A:
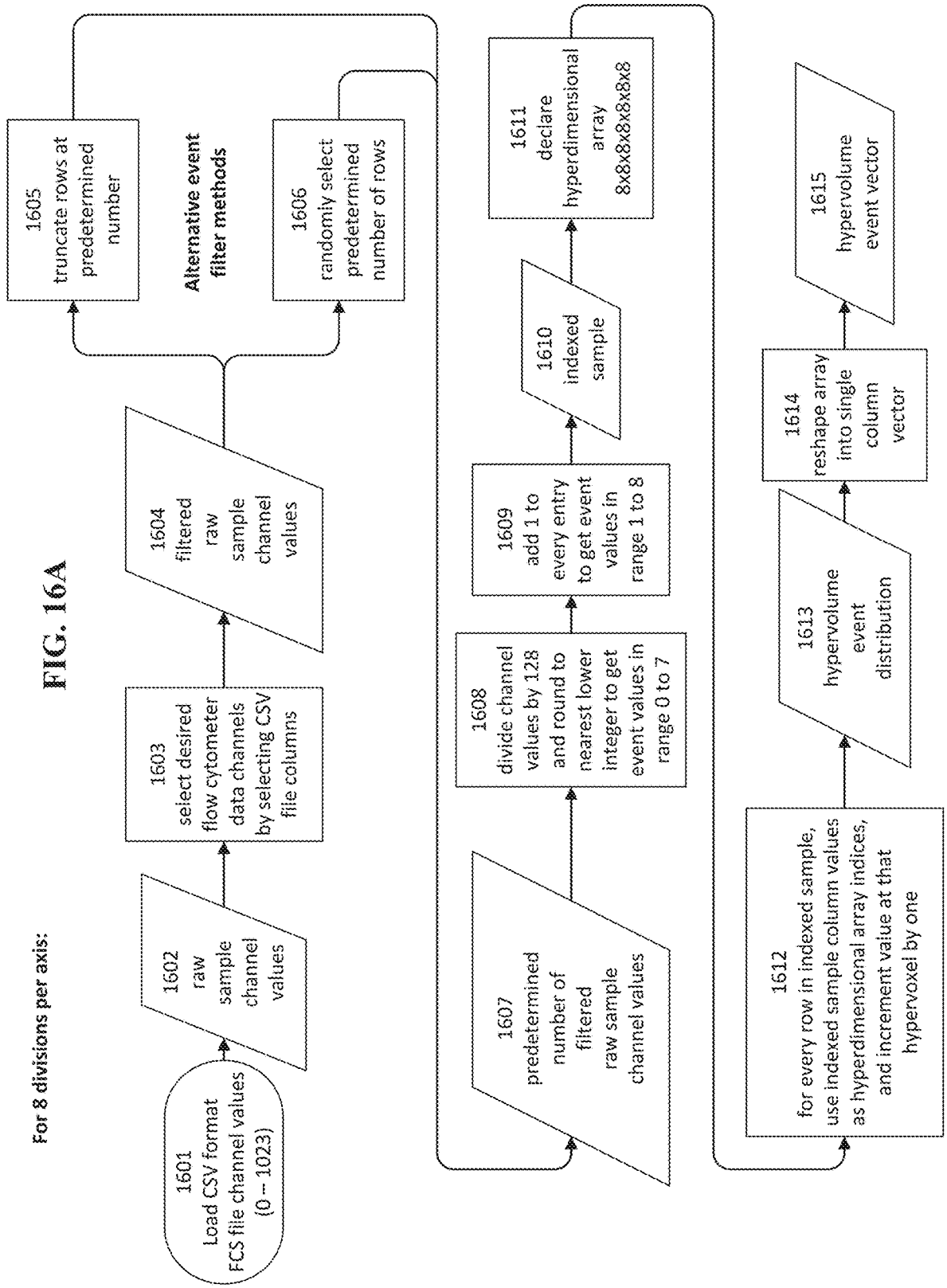
FIG. 16A and FIG. 16B illustrate a hypervoxel count population from flow cytometry data.

FIG. 16A illustrates one embodiment of populating the hypervoxels in a multidimensional space. Flow cytometry sample data that has been exported from a flow cytometer in the CSV format is loaded for processing 1601 into a raw sample channel values array 1602. Any undesired channels are excluded 1603 by selecting only the columns of interest in the array raw sample channel values array 1602, resulting in filtered raw sample channel values array 1604. When samples are exported from the flow cytometer data analysis software, such as FlowJo™, the number of events in each sample varies considerably. In some embodiments, samples can have a similar number of events for ANN training, validation, testing, and testing of naïve samples. Naïve samples are previously unseen samples that have not been applied to the artificial neural network until the neural network has completed training and its parameters have been fixed at the values achieved during training. Testing of new, previously unseen samples is referred to herein as naïve testing. This can be achieved by selecting only the first n events 1605 or by selecting n events from all events 1606, resulting in an array having a predetermined number of filtered raw sample channel values 1607. The channel values are typically exported as an integer between 0 and 1023. Representing the digital valued converted from the analog sensor value by a 10 bit analog to digital converter in the flow cytometer. This number can be divided by a factor which will result in an array having manageable dimensions. If this reduction was not performed, an array of size $1023^7$ (approximately $10^{21}$) would be required, which is far beyond current or foreseeable computer capability. For a resolution of 8 segments per axis, the raw channel value is divided by 128 1608 to yield channel values between 0 and 7. Every value thus computed is increment by 1 1609, yielding all values in the range 1 to 8, to correspond with array indices which, in this embodiment, start at 1 and not 0. This yields an indexed sample set 1610 that for every event has indices for each flow cytometer channel between 1 and 8, as a function of the original measured value.

A hyperdimensional array is declared 1611 having dimensions (resolution of each axis)$^{(number\ of\ dimensions)}$, which in this example is $8^7$. For each row in the indexed sample set, the index values in the columns are used as indices to identify a particular hypervoxel in the hyperdimensional array, and there is a count associated with that hypervoxel which is incremented each time an event in the indexed sample set is determined to be located in that hypervoxel 1612. This yields a hypervolume event distribution wherein each hypervoxel has a count representing the number of events that fell in that location 1613. This hypervolume event distribution is then reshaped 1614 into a column vector 1615 that is representative of the distribution of flow cytometer events for that sample.

Figure 16B:
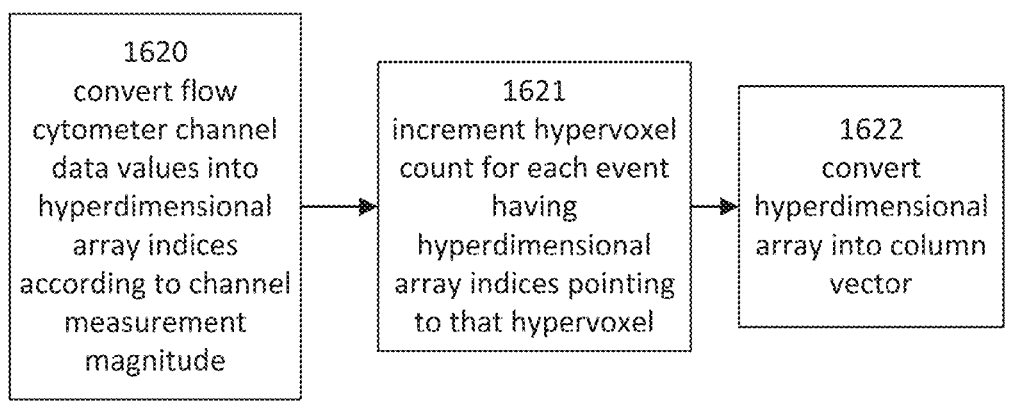

FIG. 16B illustrates one example of hypervoxel count population created from flow cytometry data. The flow cytometer channel data values are converted into hyperdimensional array indices according to channel measurement magnitude 1620, and the hypervoxel count is incremented for each event having hyperdimensional array indices pointing to that hypervoxel 1621. Then, the hyperdimensional array is converted into column vector 1622.

The above method of flow cytometry data analysis, hereinafter referred to as hypervolume distribution analysis, can be used for any flow cytometry data analysis. However, in one embodiment, this method is used to distinguish between non-tumor-bearing donors and cancer patients as a diagnostic test. Also, in another embodiment, the ANN is trained to distinguish between different types of cancer, so that instead of having two outputs indicating the ANNs classification results as "non-tumor-bearing" or "cancer", the ANN may have a plurality of outputs, one output indicating "non-tumor-bearing", and additional outputs each corresponding to a type of cancer or a disease identified by the neural network. Additionally, the ANN may be trained to identify stages of cancer, so that it may have a plurality of outputs, one output being an indication of a "non-tumor-bearing" test subject, and additional outputs, one output for each stage of each type of one or more cancer types and stages identified.

The neural network may be trained according to a training function. Training functions that are suitable for training the neural network are, among others, Levenberg-Marquardt, BFGS Quasi-Newton, Resilient Backpropagation, Scaled Conjugate Gradient, Conjugate Gradient with Powell/Beale Restarts, Fletcher-Powell Conjugate Gradient, Polak-Ribiere Conjugate Gradient, One Step Secant, and Variable Learning Rate Backpropagation.

Once the network is trained, it can be used for cancer detection or screening, cancer type determination, cancer stage determination, cancer recurrence monitoring, cancer therapy effectiveness evaluation, or cancer diagnosis confirmation testing. Periodic testing on a single subject can be used to monitor changes in a subject's cancer status over time.

The application of the neural network can be used in the early detection of other diseases, or also referred herein as conditions (e.g., diabetes, Parkinson's disease, Alzheimer's disease, pancreatitis, multiple sclerosis, hepatitis, tuberculosis, HIV). The neural network tested blood samples can be used to diagnose several diseases at once, including, for example, diabetes, Parkinson's disease, Alzheimer's disease, pancreatitis, multiple sclerosis, hepatitis, Tuberculosis, HIV and cancer. The method of using a neural network to test a blood sample offers a minimally invasive test for monitoring and diagnosing a broad spectrum of human cancers and diseases. In some embodiments, the status of a condition includes, but is not limited to, a presence of the condition, an absence of the condition, an increase in severity of the condition, a decrease in severity of the condition, a stage of the condition, a status associated with a prognosis, a response to therapy, or a status of efficacy of a therapy.

A sample may be used for training of an ANN. The training may involve applying the sample to the ANN in order to adjust the number of hidden neurons, arrangement and number of layers, interconnection weights and biases, and/or other parameters of the ANN for the condition classification determined by the ANN to match the known condition classification of the sample. The condition classification may refer to the presence or absence of a condition in the sample. The condition may refer to a disease or a stage of the disease, or a pathological condition. The presence or absence of a condition may be determined from the ANN analysis of the measurements of the sample. The condition classification may be used to generate a diagnosis of the condition in the subject. In some embodiments, a condition classification is also referred to as a status of a condition, where the condition may refer to a disease.

A sample may be used for validation of an ANN. Validation may involve applying the sample with a known classification to the partially-trained ANN and determining whether the condition classification by the ANN and the known classification match. If a high proportion of the condition classification and the known classification do not match, the ANN may undergo further training to improve its sensitivity and specificity. If a high proportion of the condition classification and the known classification match, the partially-trained ANN may have high sensitivity and specificity and may be used for testing of naïve samples. The error on the validation set is monitored during the training process to adjust the network weights and bias for the ANN being trained to improve the ANN sensitivity and specificity.

The accuracy of an ANN may be determined from at least one of specificity and sensitivity. Specificity may be determined by the proportion of the non-tumor-bearing samples that the pre-trained ANN classifies correctly. Specificity may be also referred to as true negative rate and may quantify the probability of avoiding false positives. Sensitivity may be determined by the proportion of the samples with a condition, such as a disease or stages of a disease, correctly. Sensitivity may also be referred to as true positive rate or probability of detection and may quantify the probability of avoiding false negatives. Specificity and sensitivity are determined using a set of samples with known condition classifications.

Qualification testing samples may be used for qualification testing of an ANN. Qualification testing may involve applying the samples to the trained ANN that has been frozen (i.e., its connection weights and biases have been fixed so that they do not change) to determine the condition classification. The condition classification of the qualification samples can be known prior to applying the sample to the ANN. The condition classification of the sample determined by a different test, such as a confirmation of a patient status using a biopsy analyzed by a healthcare professional (i.e. pathologist), or other highly accurate test, will be known prior to applying the sample to the ANN.

Data Augmentation

The neural network training performance can improve as the number of training samples is increased. In some embodiments, it may be desirable to have as many training samples as possible available for training. One way to optimize the utility of a limited number of training samples is by data augmentation. Data augmentation may provide for increasing the apparent number of training samples when the number of primary samples is limited.

In flow cytometry, every cell that passes through the flow cytometer can be classified as a distinct event. Each event can be independent and have values, or measurements, associated with it that may represent the light detected by each channel as a cell passes through the interrogation point of the flow cytometer. As data is acquired from the measurements of the cells passing through the flow cytometer, the data can be written to a file as a series of events. The data acquired from the measurements of a biological sample may also be referred to as the biological data sample. A series of data for such events can be used by a neural network as a training sample. The number of events collected by the flow cytometer can be proportional to size of the processed biological sample as well as the unique biological characteristics of each individual donor. The size of the processed biological sample may refer to the number of cells of the processed biological sample. In some embodiments, the distinct events captured by the flow cytometer are independent of each other, and the sequence of the data of these events can be selected without compromising the data. In some embodiments, the selection of the data is random. In some embodiments, the selection of the data is pseudo-random.

One impediment to the use of ANNs in medical applications is the desirability for an ANN to have a large number of samples on which to train. For example, depending on the application, there can be at least 100 examples of every category, or condition, the ANN is to be trained to classify. If the ANN is trained on too few samples, it may not be able to learn the full spectrum of each feature and may not perform well in subsequent trials. It may be difficult to get a sufficient quantity of samples for training, validation, and testing after training.

One approach to mitigating this problem is to utilize a form of data augmentation. A limited number of samples can be augmented by performing certain minimal transformations on the original biological data samples. For example, when training a neural network in image recognition, a set of images can be processed by having images translated and/or rotated through a plurality of rotation angles and a plurality of translation distances and directions.

One method of employing data augmentation when the input is in the form of hyperdimensional point clouds is to select subsets of a sample to form a plurality of similar but not identical point clouds for training. Using MDSC samples as an example, without data augmentation, a number of live cell events can be determined that is small enough so that the vast majority of biological data samples have at least that number of live cell events. This number can be chosen to be as large as possible without excluding too many biological data samples. For example, live cell event counts using the protocols described herein that meet this criterion can be 40,000 for MDSC, 25,000 for lymphocytes, and 30,000 for LOX-1 (OLR1). In some instances, sensitivity and specificity results after training with as few as 10,000 live cell events can be within one to two percent of the results achieved with 40,000 live cell events. In some instances, biological data samples may have live cell event counts much higher than 40,000. In some instances, each biological data sample can be divided into a number of sub-samples that will be similar, but not identical, to use for training when the number of biological samples is limited.

The augmentation of each of the primary biological samples into a plurality of related sub-samples, also referred to herein as augmented samples, can give the neural network more examples of each category, or condition, of training, validating, and testing. When two or more sub-samples are generated from the same biological sample, the samples can be referred to as sibling samples. The increase in sample size from the related sub-samples, or sibling samples, from the augmentation can provide a benefit to the neural network classifier resulting in both higher specificity and sensitivity when classifying naïve biological samples, wherein the sibling samples may comprise a selected subset of the total sample events. In some embodiments, the selection of a subset of the total sample events is random. In some embodiments, the augmentation improves the performance characteristic of the artificial neural network in detecting a condition of the naïve biological data samples, where the performance characteristic improves in at least one of sensitivity and specificity by at least 0.1% as compared to detecting the condition of the biological data sample without the augmentation process. In some embodiments, the augmentation improves the performance characteristic by at least 0.01%, 0.05%, 0.06%, 0.07%, 0.08%, 0.09%, 0.15%, 0.2%, 0.3%, 0.4%, 0.5%, 0.6%, 0.7%, 0.8%, 0.9%, or 1.0% as compared to detecting of the condition of the biological data sample without the augmentation process. Sibling samples can be different individual sub-samples from the same biological data sample. A single biological data sample can have as many sibling samples as the number of augmentations performed repeatedly on the biological data sample. The sibling samples or the sub-sample may have the same number N or a similar number to N such as N/4 to 4N of selected events as another sibling sample or another sub-sample. The sibling samples or the sub-sample may have at least N/4 selected events.

Sibling samples can offer several exemplary advantages. In cases in which multiple biological samples are used to train, test, and validate an ANN, the biological samples may yield biological data samples with different numbers of events. In some embodiments, it can be helpful to use samples with similar numbers of events or measurements. Sub-sampling can allow biological data samples with different numbers of events to be normalized to a common number of events. Where a biological data sample contains more than the number of events in a sub-sample, the use of multiple sub-samples from the same biological data sample can allow the ANN to train, test, or validate more of the events captured in the biological data sample. Thus, more data are available to the ANN and fewer events are left unanalyzed. In some embodiments, the sibling samples cover at least 50% of the biological data sample. In some embodiments, the sibling samples cover at least 55%, 60%, 65%, 70%, 75%, 80%, 85%, 90%, or 95% of the biological data. In some embodiments, at least 50% of the biological data samples are selected at least once in generating the sibling samples. In some embodiments, at least 55%, 60%, 65%, 70%, 75%, 80%, 85%, 90%, or 95% of the biological data samples are selected at least once in generating the sibling samples.

For example, biological data samples from both non-tumor-bearing individuals and individuals with cancer can be augmented to allow the neural network to better distinguish between these two categories, or conditions. Another example where augmentation is helpful is in distinguishing between patients that respond well to a therapy and patients that do not respond as well to the therapy.

In some embodiments, the number of cell events collected by a flow cytometer, also known as flow cytometer events, can exceed one hundred thousand events for a single blood sample. There is a wide variation in the number of cell events measured between different blood samples. To provide the same number of events in each sample from non-tumor-bearing individuals or individuals with cancer, the number of events selected from each sample can be less than or equal to the smallest expected number of events in any training or naïve testing sample. In some embodiments, the smallest expected number of events in any biological data sample for training or naïve testing is 20,000 to 40,000 events per sample. All the events collected by the flow cytometer do not need be included in every biological data sample presented to the neural network during training, and only a selection of the events collected may be included. The augmentation process comprises repeatedly selecting a subset of the measurements of the event features in the data, or in the biological data sample, from a biological sample from a flow cytometer to create a plurality of sub-samples or sibling samples; wherein some of the sibling samples comprise the measurements of N event features, and repeating the selecting steps to generate a plurality of sibling samples. The sibling samples are two or more sub-samples created by the augmentation process from the data from the primary biological sample or the bicilogical data sample, wherein the sibling samples have the same, similar, or different N. This augmentation process of selecting a sub-sample of the flow cytometer events and taking the N or a similar number to N events as another sub-sample or a sibling sample can be repeated many times for each of the primary biological data samples, thereby increasing the number of samples used for during training. In one example, all the events in the data from a primary biological data sample collected by the flow cytometer may be subjected to random selection, and only selected 40,000 events may be presented as a sub-sample to augment the training samples for the neural network. For example, the 40,000 events can be selected from a biological data sample having for example 100,000 total events. This selection can be repeated 40 times, creating 40 sub-samples or sibling samples from an individual primary biological data sample. Each primary biological data sample can thereby be augmented 40 times, thereby increasing the number of samples to be used in training by 40 times, significantly improving the training of the neural networks to classify naïve samples correctly. In some embodiments, the selection is random. In some embodiments, the N events may be proportional to the total events, where the N events is at most 5%, 10%, 20%, 30%, 40%, 50%, 60%, 70%, 80%, or 90% of the total event number. In some embodiments, the N events may be proportional to the total events, where the N events is less than the total events and comprises at least 1000, 2000, 3000, 4000, 5000, 10000, 20000, 30000, 40000, 50000 events. The selection may be repeated at least 10, 20, 30, 40, 50, 60, 70, 80, 90, or 100 times. The number of events captured by the flow cytometer varies for each biological sample and is proportional to the size of the biological sample. If subsequent gating is applied, the number of captured events is further reduced. N can be smaller than the minimum number of events expected from each sample to ensure that each augmented sample is sufficiently different than its sibling. Additionally, N can be large enough for the ANNs to train and converge.

During training, validation, and testing, all sibling samples or sub-samples can be segregated between the training, validation, and testing sample groups. No set of related sub-samples or sibling samples can have individual sub-samples or sibling samples in more than one of the training, validation, or testing groups. In some embodiments, the sibling samples, or the plurality of sub-samples, from the same biological data sample are used for one of training, validating, and testing during the training process of the artificial neural network.

Successive Training Process

When training neural networks, it may be common to repeat the training process many times. With each time of the training process, some of the input parameters may be changed, and additionally, the samples for training samples, test samples and validation samples may be selected. These changes are made to each neural network, because the output performance of each neural network can vary significantly. For example, some of the trained neural networks may not converge. Some of the trained networks may be subjected to data overfitting. Even a small change in the weights can lead to a significant change in the output performance of a neural network. As such, it is desirable to train many neural networks and evaluate the performance of each neural network. The performance of the neural network may inform which neural networks will be used for further analysis, where the better performing neural networks are used for further analysis. The performance of the network may be assessed by its accuracy, or in its specificity and sensitivity, against a known sample data set or a known biological data sample. Augmentation can be further applied during the successive training of the neural networks described herein. In addition to creating an augmented dataset of sibling samples or sub-samples for training, a new augmented dataset can be created for every N networks trained from augmentation of a primary biological data sample. A new augmented dataset can be created by repeating the augmentation process but using a different set of events for each sibling sample in the new set. All additionally created augmented datasets are created using data from the same primary biological samples, or the same biological data sample. During the creation of each new dataset, all the sub-samples are re-selected making each new dataset a different set of examples for the ANN to train with.

For example, if 500 networks are trained in total and a new augmented dataset can be generated for every 10 networks trained, this can result in 50 unique augmented datasets derived from 500 networks from the same primary biological data sample. These 50 unique augmented datasets can provide different dataset examples of both subjects with cancer (e.g., tumor-bearing subjects) and subjects without cancer (e.g., non-tumor-bearing subjects) that can be utilized by the neural networks and can enable the neural networks to better distinguish samples between these two categories (non-tumor-bearing or cancer). Tumor-bearing as used herein includes malignant tumor-bearing. In some embodiments, the new augmented dataset is generated for every 5, 10, 15, 20, 25, or 30 networks trained. In some embodiments, the new augmented dataset are generated for every 1%, 2%, 3%, 4%, 5%, 10%, 15%, 20%, or 25% of the total neural networks trained. In some embodiments, at least 5, 10, 20, 30, 40, 50, 60, 70, 80, 90, or 100 unique augmented datasets are generated by successive training with augmentation.

Testing a Sample Multiple Times

Augmentation can be applied in the condition classification process of naïve samples. By augmenting a naïve sample during the condition classification process, the naïve sample can be tested many times. Naïve samples may refer to biological samples or biological data samples that have not been applied to the artificial neural network previously. The condition or the status of the condition of the naïve sample may be unknown or known from a screening test or a diagnostic test. In some embodiments, the number a naïve sample is augmented corresponds to the number of times the sample is tested by the neural network as each sub-sample or sibling sample of the naïve sample is tested by the neural network. Each of these tests would be independent, and the results of each of the sub-samples or sibling samples would produce an independent result. The collective results from the neural network testing of the sub-samples or sibling samples could then be used to make a final condition classification decision on the naïve sample. For example, if a naïve sample is augmented 40 times, the sub-samples or the sibling samples from the naïve sample can be tested by the neural network for a total of 40 times. The collective results from the 40 sub-samples or sibling samples can be used to make a final condition classification decision on the naïve sample. If the condition classification results were that 37 of the sub-samples or sibling samples were classified as having a type of cancer and 3 of the sub-samples or sibling samples were classified as heathy, the final collective results from the network would be that this sample has a type of cancer. The condition classification may be determined by summing the results of testing of each of the sub-samples or sibling samples. The condition classification may be determined by majority vote of each the results of testing of each of the sub-samples or sibling samples.

Output Classifier Threshold Adjustment

A neural network can use an activation function to provide an output classification of a sample. A neural network output classifier can use a sigmoid activation function where values over a threshold belong to one output class (e.g., subjects without cancer), while values at or less the threshold belong to another output class (e.g., subjects with cancer). In some embodiments, the threshold is 0.5. In some embodiments, the threshold is 0.1, 0.2, 0.3, 0.4, 0.6, 0.7, 0.8, or 0.9. A threshold value of other than 0.5 can be used to favor either specificity or sensitivity at the expense of the other. For example, a sigmoid classifier has an output which ranges from 0 to 1, the threshold set to 0.5 treats both the sensitivity and specificity equally. However, if it desired to identify a higher percentage of cancer patients at the expense of a higher percentage of false positives, the threshold can be adjusted from 0.5 to a value greater than 0.5 and less than 1 where values below the threshold are classified as having cancer. For example, a neural network output classifier can use a sigmoid activation function where values over 0.5 belong to one class (e.g., subjects without cancer), while values 0.5 or less belong to another output class (e.g., subjects with cancer). The threshold may be adjusted from an initial threshold value to provide a preferred performance when classifying biological data samples or biological samples, for example prioritizing sensitivity at the cost of reduced specificity, or prioritizing specificity at the cost of reduced sensitivity, thereby improving the overall performance for a specific application. For example, testing of samples at a threshold other than 0.5 in classifying samples may improve the network performance for sensitivity or specificity. A transformation can be employed rescaling the network sigmoid output to give a condition classification result for a chosen threshold.

Biological samples may change over time after collection. For example, neutrophils in blood samples can become activated over time while stored in a collection tube. Activated neutrophils can be less dense than non-activated neutrophils, and can be therefore more difficult to separate from MDSC sub-populations using centrifugation. This effect can be mitigated by use of a gel-containing cell preparation tube such as a BD Vacutainer CPT™ (Becton, Dickinson and Company) and centrifuging the tube within 4 hours of collection. Alternatively, the effect of changes in biological samples over time may be compensated for by having multiple neural networks train on training sets wherein the non-tumor-bearing samples and the cancer patient samples are held for a predetermined period of time, such as, for example, 1 hour, 2 hours, 4 hours, 8 hours, 12 hours, 24 hours, or 36 hours, at a predetermined temperature, such as 0 degrees C., 4 degrees C., 15 degrees C., 20 degrees C., 23 degrees C., 25 degrees C., 30 degrees C., or 37 degrees C. Subsequently, when the data from the biological samples, or biological data samples, are to be tested by the neural network, they can be tested using the appropriate neural network that was trained on biological data samples that had been stored in the same or similar conditions, in terms of time or temperature, after collection before processing as the new test sample.

In some instances, an ensemble of similar neural networks may perform better than any single neural network. One reason for this is that neural networks have a tendency to find a local minimum of the error function during training instead of the global error minimum. The neural networks can then perform well on new test data samples that are similar to the biological data samples used for training, but not as well on other new data samples that are less similar to the biological data samples used in training. A feedforward classifier neural network will generally output a value for each category of output it has been trained on. If a neural network has been trained on two output categories, "non-tumor-bearing" and "cancer", it will put out two values, one at the "non-tumor-bearing" output and one at the "cancer" output. The two values will sum to 100%. The higher value represents the classification result, and its value indicates how "confident" the neural network is in the result. If a first neural network analyzing a first test data sample has an output of, for example, confidence of non-tumor-bearing=40% and confidence of cancer=60%, and a second neural network, analyzing the same test data sample has an output of confidence of non-tumor-bearing=99% and confidence of cancer=1%, the second network is more likely to be correct, because it is detecting a feature or features in that particular test data sample that it generalizes better on than the first network.

Figure 6B:
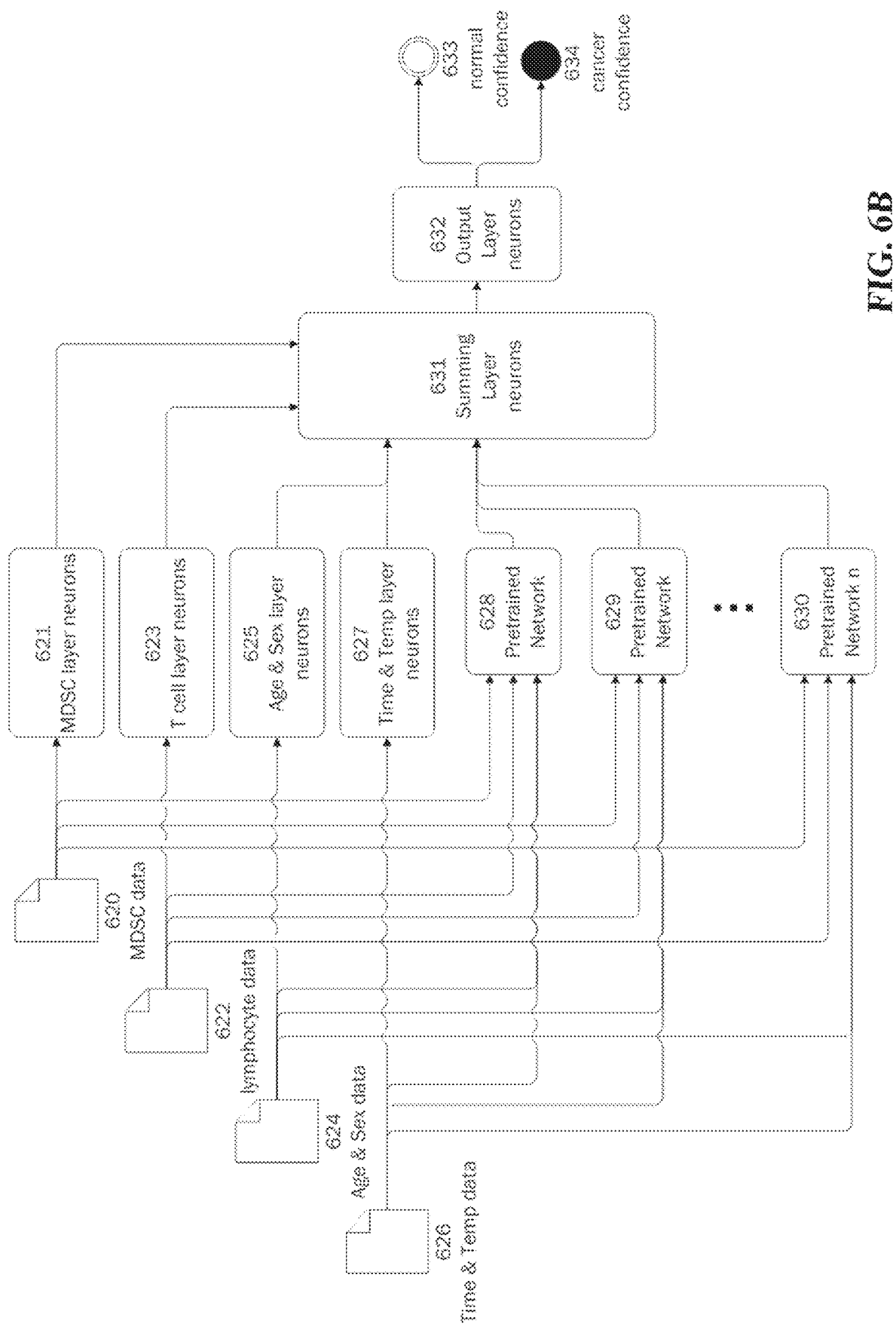
FIG. 6B illustrates a master neural network for hypervolume distribution analysis incorporating pre-trained primary networks.

One architecture for an ensemble neural network architecture is shown in FIG. 6B. Pretrained networks 1 through n 628, 629, 630 have been previously trained on a first training data set 620, 622, 624, 626, which are presented as various input layers 621, 623, 625, 627. They are then incorporated in the master neural network as shown in the FIG. 6B. The master neural network is then trained on a second training data set 620, 622, 624, 626, which are presented as various input layers 621, 623, 625, 627 and are presented to the master network and to the pretrained networks simultaneously. The input layers and the pretrained networks can be presented to a summing layer 632 and then to the output layer 632 of the artificial neural network to provide levels of confidence in the classification of the sample, as normal 633 or as having cancer 634. The master network undergoes training as usual, but the pretrained networks retain the trained parameters they received in their pretraining. The master network will learn that when presented with a new biological data sample having certain characteristics, the most accurate condition category result will be a product of its own training on the input biological data sample and by learning to give the most weight to the particular pretrained network that gives the most accurate output for that type of biological data sample. The master network will therefore have the benefit of input from a plurality of specialized networks and from its own training on a combination of a training set and the outputs from the pretrained networks.

When the master network is trained, the training data set for the master network (which may include training, validation, and test subsets depending on the training algorithm utilized) can be distinct from the training data set or sets used to train the pretrained networks. This is because the neural network configurations disclosed herein have extremely high accuracy on data samples that has been used in their training set. They effectively "memorize" any sample they have previously trained on, and one or more of the pretrained networks will have near 100% accuracy on any previously seen samples. Therefore, the master network will disregard the actual sample hypervolume input data and rely exclusively on the outputs of the pretrained networks.

Voting

Multiple trained neural networks can be collectively used to classify a naïve sample. When distinctly trained neural networks are used to classify a naïve sample, the artificial neural networks may not agree on a condition classification. In the case of a condition classification disagreement amongst the artificial neural networks, a voting process can be implemented by a master neural network to select the most probable condition classification. For example, when three distinctly trained neural networks are used to classify a naïve sample, all three networks might not agree on the condition classification results. For example, if seven separately trained neural networks were used to classify a single naïve sample and four or more of these networks agree that this sample is likely have come from a tumor-bearing sample, and three or less of the networks believe this sample to be non-tumor-bearing, then the collective voting by the master network would classify this sample as a sample from a tumor-bearing subject. The artificial neural networks can be applied to the sample dataset or biological data samples, and used to provide condition classifications, where the multiple artificial neural networks are trained separately. Each of the multiple artificial neural networks can provide an independent condition classification. The independent condition classifications by the multiple artificial neural networks can be analyzed by a master neural network to give a global classification of the biological sample, where the global classification is the most probable category, or condition, based on a frequency of the condition classifications of the sample dataset or biological data samples. The frequency of a condition classification may be determined by the number of occurrence of the condition classification as compared to the overall number of condition classifications. The frequency may be weighted by the specificity and/or sensitivity of the artificial neural network providing the condition classification, giving more weight to more accurate artificial networks. In some embodiments, the artificial neural network provides a condition classification for at least three sub-samples or sibling samples from the same biological data sample to give a global condition classification of the biological sample, where the global condition classification is the most probable category, or condition, based on a frequency of the condition classifications of the sub-samples or sibling samples. In some embodiments, the global condition classification is also referred to as global status.

The artificial neural networks used by the master network can be different in many ways. The number of network layers, number of neurons used, the training function, the method of output error calculation, the weight and bias updating method, the number of inputs, or the type of inputs, or combinations thereof can be different for each artificial neural network used in the collective voting by the master neural network. Each artificial neural network may contribute differently to the collective vote applied to the master neural network to improve the overall classification results of naïve samples. In some embodiments, at least three artificial neural networks are used by a master network where the at least three artificial networks vary in number of network layers, number of neurons used, training function, method of output error calculation, weight and bias updating method, number of inputs, type of inputs, or combinations thereof. In some embodiments, a sample may be determined to be in a global classification by the collective voting as determined by the master neural network, where the sample is classified by at least 50%, 60%, 70%, 80%, 90%, 95%, or 99% of the separately trained artificial neural networks to be in the same condition classification as the global classification.

For example, a single naïve sample may be classified by seven separately trained artificial neural networks, where four or more of the trained artificial neural networks agree that this sample is likely have come from a person with a type of cancer and three or less of the networks believe this sample to be non-tumor-bearing. Then, a collective voting by the master neural network may classify the sample as a sample with a type of cancer.

Updating Training Data

Artificial neural networks can learn very complicated examples of a condition or a disease (e.g., cancer). The accuracy at which the neural networks can classify naïve samples can additionally improve as more samples are applied during the training process. It is desirable to periodically update the neural network and improve its ability to classify new or naïve data samples by updating the training data as additional examples of a condition or disease become available. While in operation, the neural network can be used to classify the event data from a subject, also referred to as subject event data. This classified subject event data can be subsequently used by the neural network to incrementally update neural network, thereby improving the ability of the neural network to classify future naïve data samples. The network retraining and updating based on the additional data that has been accumulated can be performed in batches based on an increased number of labeled samples, for example when an additional 100 or 1,000 samples have been received and processed, or based on an elapsed calendar timer period, for example annually. In some embodiments, the continual training may be performed for a batch of at least 100, 200, 300, 400, 500, 600, 700, 800, 900, 1000, 1500, or 2000 biological samples. In some embodiments, the continual training is performed at least 1, 2, 3, 4, 5, 6, 7, 8, 9, 10, 11, or 12 times a year. In some embodiments, the continual training is performed once a year, a month, or a week. In some embodiments, the continual training may add one or more condition classifications to the artificial neural network. Subjects who have been tested and had their status of a condition predicted by the neural network can be monitored on an ongoing basis, to confirm that they are non-tumor-bearing or alternatively have cancer. Additional categories of the status of the condition may thereby be developed for very early or pre-cancerous conditions, by identifying subjects who are determined at the time of the test to be non-tumor-bearing, but develop a cancer at some time months or years after the initial test.

Predicting Therapy Responses and Treatment Monitoring

In the treatment of cancer and other conditions, some subjects may respond well to a specific type of therapy (i.e., responders) while other patients do not (i.e., non-responders). The treatment of cancer and other conditions may comprise administration of a therapy at specified dosages, frequencies, and administration routes. The therapy may comprise one or more therapies. Specific types of therapies can be costly, debilitating and/or taxing for a patient. Therefore, predicting how a subject may respond to a therapy prior to receiving the therapy would be of great value.

The neural network can be trained to accurately predict a patient's response to existing types of therapies, experimental types of therapies, and/or other types of therapies for the treatment of cancer and other diseases as well as identifying the optimum type of treatment for a patient based on the neural network analysis of their biological data sample. Additionally, the neural network can be used to continually monitor the treatment responses of patients allowing for doctors to alter patient treatment regimens as appropriate. In some embodiments, adjusting the treatment comprises changing a dose, frequency, or type of therapy, or combination thereof.

Monitoring treatment responses by comparing testing results of the biological samples (i.e. blood samples) with the neural network before treatment and on treatment would allow for better prediction of the patient's response to a known therapy and additionally allowing for the therapy to be administered to patients more efficiently resulting in a more individualized treatment with improved results.

Active Surveillance and Recurrence Monitoring

In some instances, treatment of the cancer is not practical as the risks outweigh the benefits, so the patients with cancer are put on active surveillance by a healthcare professional or a physician. These patients are closely watched and undergo numerous and frequent exams until their condition worsens and may needtherapeutic intervention. The neural network can be trained to better predict at what point the patient can begin active therapy to achieve the greatest response without invasive diagnostic or imaging procedures based upon their sample data.

Furthermore, once a patient is treated for their tumor, such as through radiation, chemotherapy, immunotherapy, surgical resection, and/or other therapy, they are regularly monitored to ensure that the tumor was eliminated, and that new tumor formation does not occur. This is known as recurrence monitoring. The neural network can be trained using biological data sample to accurately identify whether a patient's cancer has returned before exhibiting systemic symptoms of their cancer.

Use of Neural Network with Other Tests

Screening tests (e.g., mammograms, rectal exam, Prostate-Specific Antigen (PSA) test, low dose computed tomography (LDCT) tests, computed tomography (CT), and X-ray) are given routinely to subjects who appear to be healthy and are not suspected of having cancer or other disease conditions. The purpose of the screening test can be to detect a cancer and/or other pathologies as early as possible in order to improve treatment and clinical outcomes. Screening tests may be performed on a biological sample from the subject and may be the first test performed on the biological sample in a set of tests.

If the screening test reports results in abnormal results, the patient may be given a more comprehensive diagnostic test (e.g., biopsy, Cystoscopy, MRI). In some instances, the diagnostic tests can be used to confirm the diagnosis from the initial screening test and can be referred to as confirmatory tests. A diagnostic test may be stressful, emotionally taxing, uncomfortable and/or painful and expensive for the patient. Furthermore, many of the diagnostic tests may be unnecessary, and the accuracy of the screening test may be poor and the results from the diagnostic tests may turn out to be negative. It is therefore desirable to have a confirmatory test with a higher accuracy than the screening test. It is also desirable for the confirmatory test to be minimally invasive and less expensive than a diagnostic test. Testing of a biological sample by application of an artificial neural network as described herein may be used as a confirmatory test.

For example, if a screening test indicates results that are out of non-tumor-bearing range, confirmatory test can then be employed to confirm the results of the screening test, where the confirmatory test has a higher accuracy than the screening test in detecting a disease or a condition. Using the screening test and the confirmatory test in conjunction can serve to eliminate unnecessary diagnostic test, which can reduce cost and stress to the subject. A neural network testing of a blood sample can be used as a confirmatory test. The confirmatory test using a neural network can offer a minimally invasive test and reduce unnecessary diagnostic tests, costs and stress to the subject.

A proximate cause of cancer may be mutations in a subject's DNA, where the mutations may be present on DNA that control cell function. Development of diagnostic tests for cancer have been proposed, where the diagnostic test can sequence a subject's genome and compare mutations in the subject's genome to a library of mutations that have been identified as being correlated with cancer. The potential sensitivity and specificity of this test may prove to be very high. The cost of sequencing for such a test can be quite high. Reimbursement by insurance carriers may be limited until the diagnostic test has demonstrated sufficient accuracy, leading to reluctance to use the test by the diagnosticians and professionals in the health care and medical industry.

There is a need for a companion preliminary test that may be non-invasive, have a low cost, and identify the possible presence of cancer or a condition in a subject with a high sensitivity and specificity (e.g., 85% or above) to identify subjects who may be good candidates for a diagnostic test. The subsequent diagnostic test may be a DNA sequencing test. The test disclosed herein, i.e. measuring flow cytometry data using a trained neural network or networks, may be used as a companion preliminary test. The neural network can provide a further diagnostic recommendation instead or in addition to a classification of a biological sample from a subject as non-tumor-bearing or potentially cancerous or potentially having a condition. A high sensitivity and specificity for such a companion preliminary test may be at least 70%, 75%, 80%, 85%, 90%, or 95% in identifying subjects who may be good candidates for a diagnostic test.

Flow Cytometry Data Analysis using Convolutional Neural Networks

In some embodiments, the systems, methods, media, and networks described herein include using a convolutional neural network for data analysis. Convolutional Neural Networks (CNNs) are a category of Neural Networks that have proven very effective in areas such as image recognition and classification. CNNs have been successful in identifying faces, objects and traffic signs apart from powering vision in robots and self-driving cars. CNNs have been primarily used for 2D image recognition, but some work has been done using CNNs for 3D spatial recognition. CNNs derive their name from the "convolution" operator. The primary purpose of convolution is to extract features from the input image. Convolution preserves the spatial relationship between pixels by learning image features using small squares of input data. A typical application would include a number of small matrices called kernels, having dimensions of for example 5×5 pixels for use with a 100×100 pixel image. Each kernel is stepped over the entire image in a zigzag pattern, and at each step, the kernel matrix is multiplied by the underlying image data. Each kernel is trainable, and over time they converge on kernel matrix element values which, when convolved with the underlying image values, are successful at identifying primitive features in the image. Each kernel learns to identify a different primitive feature. The output of each convolution is fed forward to the next layer, which is a non-linear layer called a Rectified Linear Unit (ReLU) layer. The third layer is a pooling layer. The pooling layer aggregates primitive features identified by the kernels into more complex, higher order features. A CNN will typically have a plurality of Convolutional+ReLU+pooling layers in sequence, with a final fully connected Classification layer at the output, as is well understood in the art.

When CNNs are used for 3D shape recognition, the kernels may be cubic matrices instead of square matrices. Similarly, each ReLU and pooling layer may be 3 dimensional instead of 2 dimensional. CNNs can be expanded to as many dimensions as desired, but the number of steps and convolution calculations increases exponentially as dimensions are added. Beyond 4 or 5 dimensions, depending on the resolution of the input hyperspace and the size of the kernels, the calculations required may become excessively time consuming.

Figure 9:
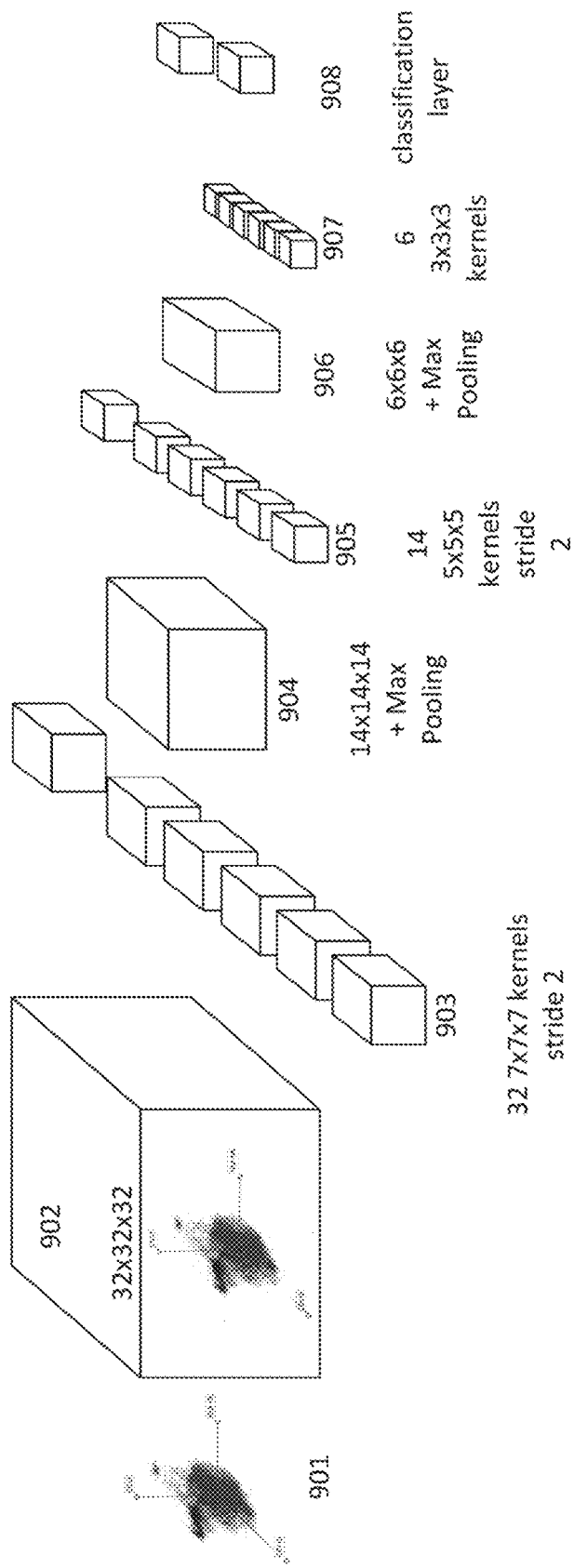
FIG. 9 illustrates an example of a 3D convolutional neural network data analysis flow for 3D objects.

Convolutional neural network architectures developed for 3D shape recognition can be adapted to operate on 3D spaces having voxels populated with flow cytometer data event or cell counts. For purposes of illustration, some of the descriptions herein use 3-dimensional shape recognition to explain the automatic operations; however, the technology can be readily extended to higher-dimensional shape recognition. One example of a 3D CNN for shape recognition is shown in FIG. 9. Flow cytometry measurements of live cells or other discrete events are used to generate a 3D point cloud of measurement events 901. In one embodiment, the point locations are used to generate a 32×32×32 voxel occupancy space 902 wherein each voxel is tagged with the number of live cells or other events having measured flow cytometers for a given channel that cause them to be located in a particular voxel of a 3D space formed by axes which are representations of flow cytometer channel values. In one embodiment, 32 7×7×7 kernels or filters 903 are convolved with the occupancy space 902 to learn indicative occupancy distributions in the occupancy space 902 during training. The outputs of the first kernel set 903 are fully connected to a first 14×14×14 max pooling layer 904. A second set of 14 5×5×5 kernels 905 is convolved with max pooling layer 904 and fully connected to a second 6×6×6 max pooling layer 906. A third set of 6 3×3×3 kernels 907 is convolved with max pooling layer 906 and is fully connected to classification layer 908. The convolved kernel outputs can be processed by an ReLU non-linear layer, or other non-linear function such as tanh or sigmoid can be used instead.

In some embodiments, the algorithm optionally converts the description to a standard medical 3-dimensional imaging format like NIfTI or other standard 3D data representation format.

The CNN can be pretrained in a low-dimension low-resolution data space, such as a 3-dimensional 16×16×16 resolution data space. Additional dimensions may be added to the data space and the CNN one at a time, with the CNN continuing to train, having retained the values learned from the lower dimension pre-training. This minimizes the training effort, which would be extremely time consuming in, for example, a hyperspace having 16 divisions per axis and 4 dimensions. For example, a kernel of dimension $8^4$ stepping through a hyperspace having $16^4$ hypervoxels with a stride of 2 pixels would may require 390,625 steps. Each step may require $8^4$ or 4,096 floating point calculations. Pre-training on reduced dimension data sets may substantially reduce the required number of epochs for training. To increase computational speed, calculations can be performed with a local networked system of computers or an online computational service such as Amazon Web Services High Performance Computing (AWS HPC), which allows calculations to be performed using thousands of Xeon processors and thousands of Graphics Processor Units (GPUs) simultaneously. Use of online services such as AWS HPC may allow dimensionality to increase to 5 or more dimensions in the hyperspace.

Figure 10:
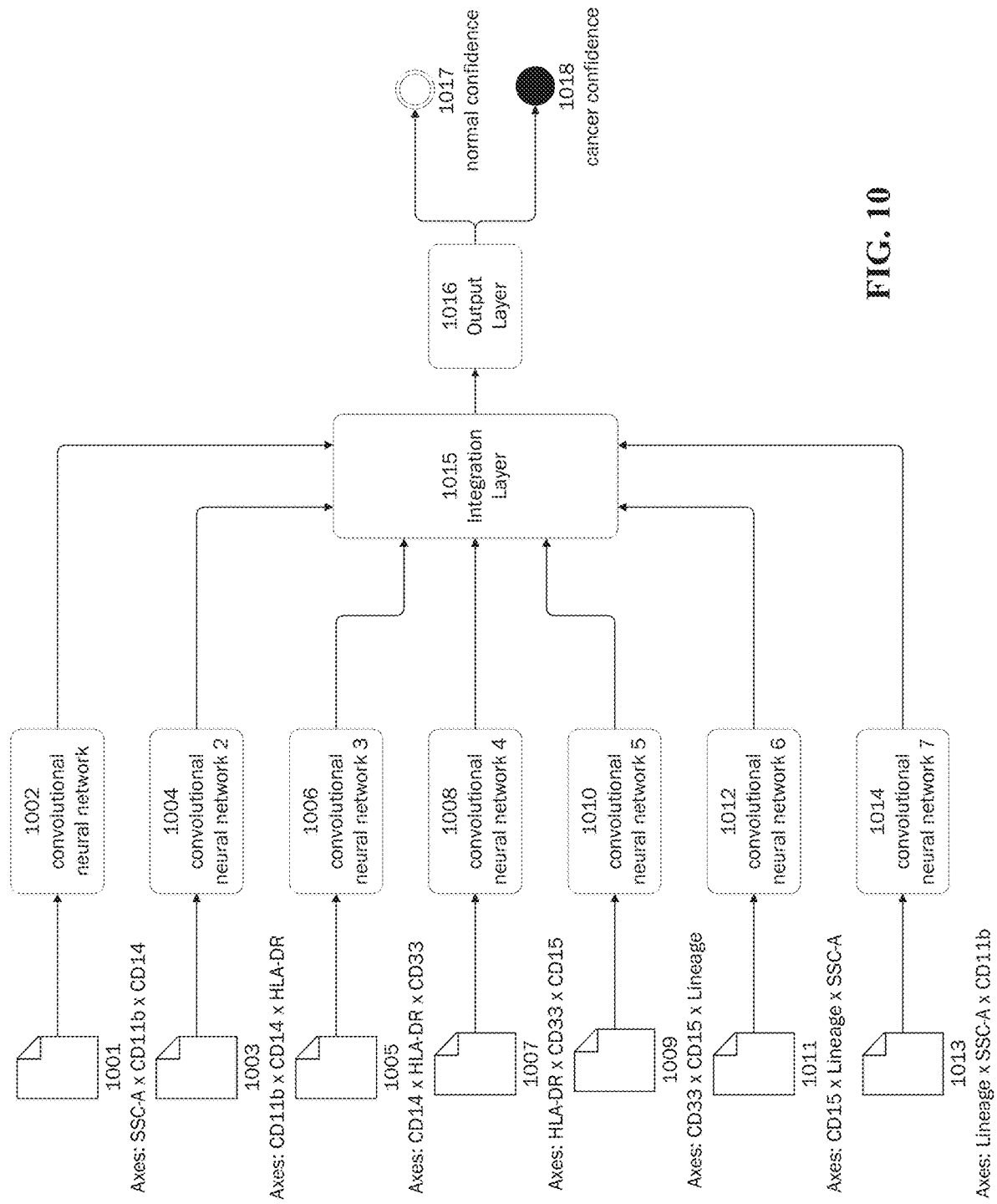
FIG. 10 illustrates an example of creating projection views of an object and using multiple convolutional neural networks for analysis.

Referring to FIG. 10, in some embodiments, an ensemble of at least two deep convolutional neural networks, each ensemble looking at a different 3-dimensional "projection" of a higher-dimensional structure, may be used to avoid the computational cost of going directly to 4-dimensional, 5-dimensional, or higher-dimensional processing. Seven 3-dimensional data spaces 1001, 1003, 1005, 1007, 1009, 1011, 1013 are generated from flow cytometry data that has been transformed into 3D voxel counts as described above. The axes of the 3D data spaces are taken 3 at a time from the 7 or more dimensions produced by the flow cytometer data. The first data space 1001 uses axes SSC-A, CD11b, and CD14. The second data space 1003 uses axes CD11b, CD14, and HLA-DR. Each next data space eliminates one previously used axis and adds a new axis. A separate 3D convolutional neural network 1002, 1004, 1006, 1008, 1010, 1012, 1014 processes the data from each 3D data space. The integration, or pooling, layer 1015 integrates the results from each convolutional neural network, presents the results to the output layer 1016, and produces a final result which is a classification confidence value at outputs 1017 and 1018 indicating the networks classification result.

Figure 11:
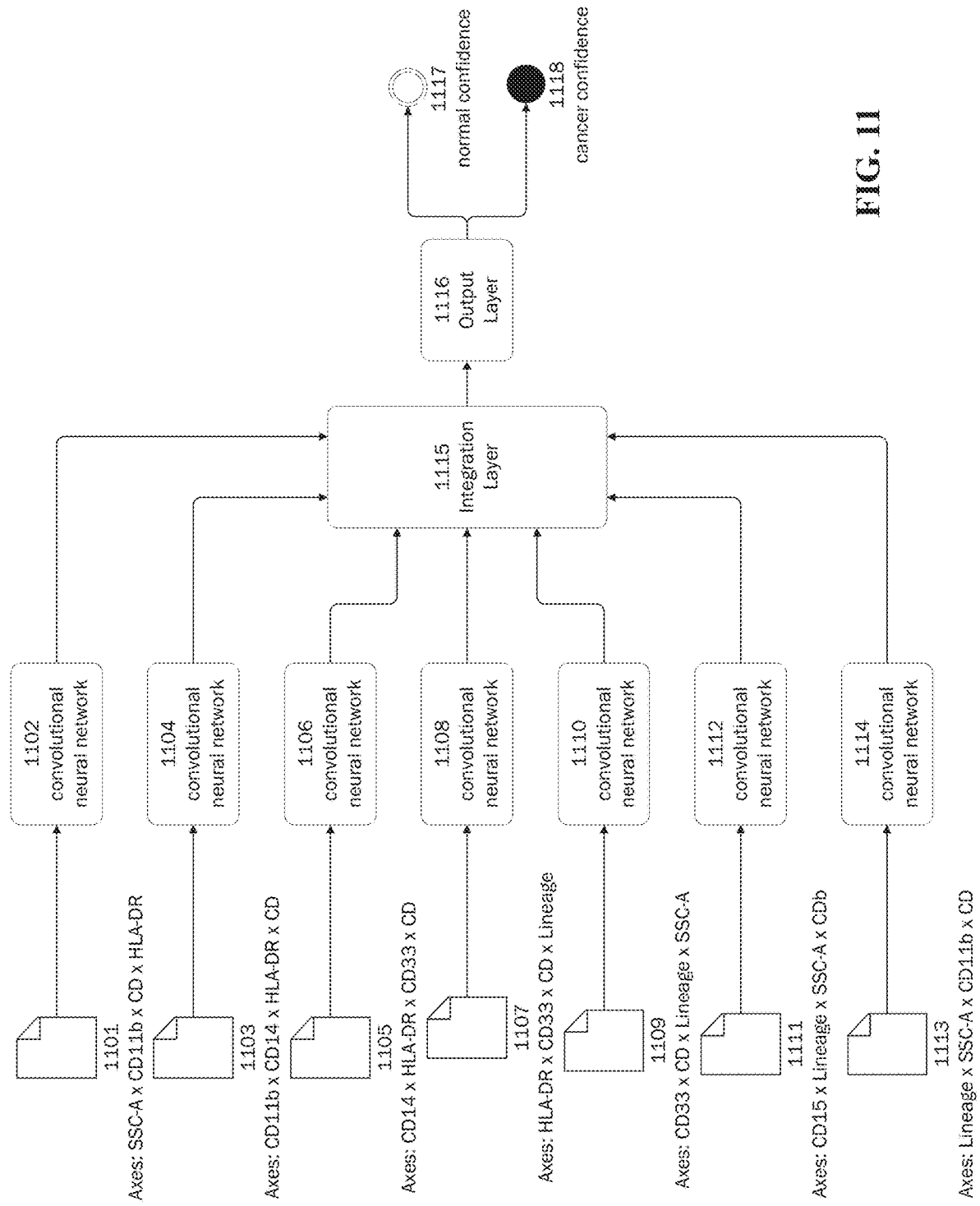
FIG. 11 illustrates an example of a convolutional neural network architecture for processing multiple reduced dimension subsets of a higher dimension data space.

FIG. 11 shows an example of employing seven convolutional neural networks 1102, 1104, 1106, 1108, 1110, 1112, 1114; each network handles a 4-dimensional projection of the flow cytometry data occupancy space 1101, 1103, 1105,

1107, 1109, 1111, 1113. This approach is an alternative for high-resolution multidimensional representations if flow cytometry data includes more than 5 markers/dimensions. As described above, results may be presented to the integration layer 1115, output layer 1116, and produces a final result which is a classification confidence value at outputs 1117 and 1118 indicating the networks classification result.

In some embodiments, the systems, methods, media, and networks described herein comprise performing a dimensionality reduction (e.g., a dimensionality reduction algorithm). Dimensionality reduction can be performed at any time during the analysis. In some embodiments, dimensionality reduction is performed at the beginning of the analysis. In some embodiments, dimensionality reduction is performed at a middle step of the analysis.

In some embodiments, the convolutional neural network comprises a multidimensional kernel having the same number of dimensions as the hyperspace it is convolved with. In some embodiments, the convolutional neural network comprises a multi-layered network. In some embodiments, the identifying the cell population distribution comprises rotating the multidimensional flow cytometry data. In some embodiments, identifying the cell population distribution comprises creating a 2-dimensional projection view of the multidimensional flow cytometry data. In some embodiments, identifying the cell population distribution comprises creating a 3-dimensional projection view of the multidimensional flow cytometry data. In some embodiments, identifying the cell population distribution comprises pooling a plurality of rotated views.

In some embodiments, identifying the cell population distribution comprises a two pass approach. The two-pass approach comprises a first pass identifying locations containing features of interest in a first resolution environment. The two-pass approach comprises a second pass performing classification in a second resolution environment, wherein the second resolution is higher than the first resolution.

In some embodiments, identifying the cell population distribution comprises identifying a preliminary gating region based on one or more of the following: morphology, singlets, and a CD14 marker.

In some embodiments, identifying the cell population distribution comprises a training step. The training step comprises comparing samples in at least two different biological conditions. At least two different biological conditions comprise a non-tumor-bearing state and a cancer state. In some embodiments, the training step comprises correlating the cell population distribution with a manually gated region. In some embodiments, the training step further comprises validating the identified cell population distribution with the manually gated region using clinical data.

In some embodiments, identifying the cell population distribution is performed on a computing platform with a plurality of processors. In some embodiments, a processor comprises a computer processor, a graphic processing unit, an FPGA-based processor, and/or an ASIC. In some embodiments, the computing platform comprises a client-server computing platform, for instance, Microsoft CNTK which has a 3-dimensional capability and is client-server based. In some embodiments, the computing platform comprises a client-server computing platform, for instance, Amazon Web Services High Performance Computing, which allows simultaneous use of thousands of processors and/or GPUs and is client-server based. Some embodiments utilize tens of servers or more, with multiple processors per server.

In some applications, a sample is acquired from a subject with cancer. The cancer may be selected from a group consisting of breast cancer, cervical cancer, ovarian cancer, colorectal cancer, melanoma, sarcoma, endometrial cancer, bladder cancer, renal cancer, gastric cancer, thyroid cancer, malignant lymphoma, lung cancer, prostate, cancer, liver cancer, and pancreatic cancer.

In various embodiments, the systems, methods, media, and networks described herein include selecting a cell population based on the cell population distribution in a multidimensional data space defined by axes which are the measurement channels of a flow cytometer instrument. The cell population to be selected may comprise myeloid-derived suppressor cells (MDSCs). The cell population to be selected may be dependent on the presence of at least one, two, or three cell markers, selected from the group consisting of CCR2, CXCR4, CXCR2, CD1d, CD1d1, CD11a, CD11b, CD11c, CD14, CD15, CD16, CD16a, CD16b, CD16low, CD31, CD32, CD32a, CD32b, CD32b/c, CD32c, CD33, CD34, CD38, CD39, CD44, CD45, CD49d, CD62L, CD62b, CD80, CD115, CD162, CD301a, CD301a/b, CD301b, Complement Component C5a R1, EMR1, F4/80, Galectin-3, gp130, Gf-1, HLA-DR-, ICAM-1/CD54, IL1RI, IL4Rα, IL-6Rα, LOX-1 (OLR1), M-CSFR, nitric oxide, KIT, LIN−, MHC I, PD-L1, TIE2, Transferrin R, VEGFR1, VEGFR2, and Integrin α4β1.

In some embodiments, the cell population to be selected may be dependent on the presence of at least one, two, or three cell markers, selected from the group consisting of CD86, B7-H4, CD11c, CD14, CD21, CD23, CD34, CD35, CD40, CD117, HLA-Dr, and Ly6.

In some instances, the cell population to be selected may be dependent on the presence of at least one, two, or three cell markers, selected from the group consisting of CD3, CD14, SSEA-1CD16, CD33, HLA-DR, CD19, CD56, LOX-1 (OLR1), and CD11b. In some instances, the cell population to be selected may be dependent on the presence of at least one, two, or three cell markers, selected from the group consisting of CD3, CD19, CD56, CD4, and CD8.

In some embodiments, the cell population to be selected may be dependent on the presence of myeloid-derived suppressor cells (MDSC), selected from the group consisting of polymorphonuclear MDSC (PMN-MDSC), granulocytic MDSC (G-MDSC), monocytic MDSC (M-MDSC), and early-stage MDSC (e-MDSC).

In some embodiments, the cell population to be selected is dependent on the presence of cell markers for myeloid-derived suppressor cells (MDSC) selected from the group consisting of CD14-/CD11b+/CD15+, CD14-/CD11b+/CD66+, CD11b+/CD14+/HLA-DR(low) or −/CD15−, and CD11b+/CD14+/HLA-DR(low) or −/CD15− (where (low) indicates a low cell population, + indicates a high population, and − or − indicates a negative cell population).

In some embodiments, the cell population to be selected is dependent on the presence of cell markers for myeloid-derived suppressor cells (MDSC) selected from the group consisting of CD14−/CD11b+/CD15+/LOX-1 (OLR1), CD14−/CD11b+/CD66+/LOX-1 (OLR1), CD11b+/CD14+/HLA-DR(low) or −−/CD15−, and CD11b+/CD14+/HLA-DR(low) or −/CD15−. In some embodiments, the cell population to be selected is dependent on the presence of cell markers for myeloid-derived suppressor cells (MDSC) selected from the group consisting of CD14+/CD124+, CD15+/CD124+, Lin−/HLA-DR−/CD33+, CD14+/HLA-DR(low)/−, CD15+/CD14−/CD11b+, CD15+/FSClow/SSC (high), CD15−/CD14+/CD33high/HLA-DRlow, CD15+/CD33high, CD14−/CD15−/CD33(high), and Lin−/HLA-DR(low)/CD11b+ (where (high) indicates a high cell population). In some embodiments, the cell population to be selected is dependent on the presence of cell markers for myeloid-derived suppressor cells (MDSC) selected from the group consisting of B lymphocytes, T lymphocytes, Natural killer cells (NK cells), and combinations thereof.

In some embodiments, the cell population to be selected is dependent on the presence of myeloblast lineage cells, selected from the group consisting of eosinophils, basophils, neutrophils, and combinations thereof.

In some embodiments, the cell population to be selected is dependent on the presence of neural stem cell lineage cells, selected from the group consisting of neurons, astrocytes, oligodendrocytes, and combinations thereof.

In some embodiments, the cell population to be selected is dependent on the presence of endodermal stem cells lineage cells, selected from the group consisting liver stem cells, hepatocytes, pancreatic stem cells, islet cells, intestinal stem cells, intestinal cells, and combinations thereof.

In some embodiments, the cell population to be selected is dependent on the presence of mesenchymal stem cell lineage cells, selected from the group consisting of adipocytes, stromal cells, fibroblasts, myoblasts, skeletal myocytes, cardiomyocytes, smooth muscle myocytes, osteoblasts, chondroblasts, chondrocytes, osteocytes, and combinations thereof.

In some embodiments, the cell population to be selected is dependent on the presence of circulating tumor cells (CTCs), selected from the group consisting of traditional CTCs, cytokeratin negative (CK−) CTCs, apoptotic CTCs, small CTCs, and combinations thereof.

Enhanced Neural Network Architectures

The systems and methods described herein can be used alone or in combination with other diagnostic methods for improved performance. The above described methods for analyzing MDSC or MDSC and T cell hypervolume distributions can be combined with the results of an additional test such as a prostate specific antigen (PSA) test, PSMA-(prostate specific membrane antigen), a CEA—(Carcino-embryonic antigen) test, a CA-125—(Cancer antigen 125) test, cancer antigen 19-9 (CA19-9) test, prolactin (PRL) test, hepatocyte growth factor (HGF) test, osteopenia (OPN) test, myeloperoxidase (MPO) test, tissue inhibitor of metalloproteinases 1 (TIMP-1) test, a PBMC to neutrophil ratio test, or other protein, nucleic acid and other biomarkers test. The results of the additional test may be used as an additional input to the neural network or an algorithmic calculation can be performed that utilizes the MDSC or MDSC and lymphocyte sample test results output of the flow data hypervolume distribution neural network in combination with the additional test results to improve diagnostic results. The results of one or more of any conventional cancer diagnostic or screening test may be combined with the neural network sample test output, or may be used as another input to the neural network for improved test output performance.

3D convolutional neural networks are well known in the art. They are frequently used for shape recognition in 3-dimensional spaces, and may be used in 4-dimensional spaces, which include the three spatial dimensions plus a time dimension, in applications such as self-driving cars and robotics.

Lung nodule detection using convolutional neural networks has been extensively studied. Both 2D images such as X-ray images and 3D images such as computed tomography (CT) scans have been used as input. These systems have been shown to perform well, but may have difficulty distinguishing between malignant tumors and benign nodules.

Figure 14:
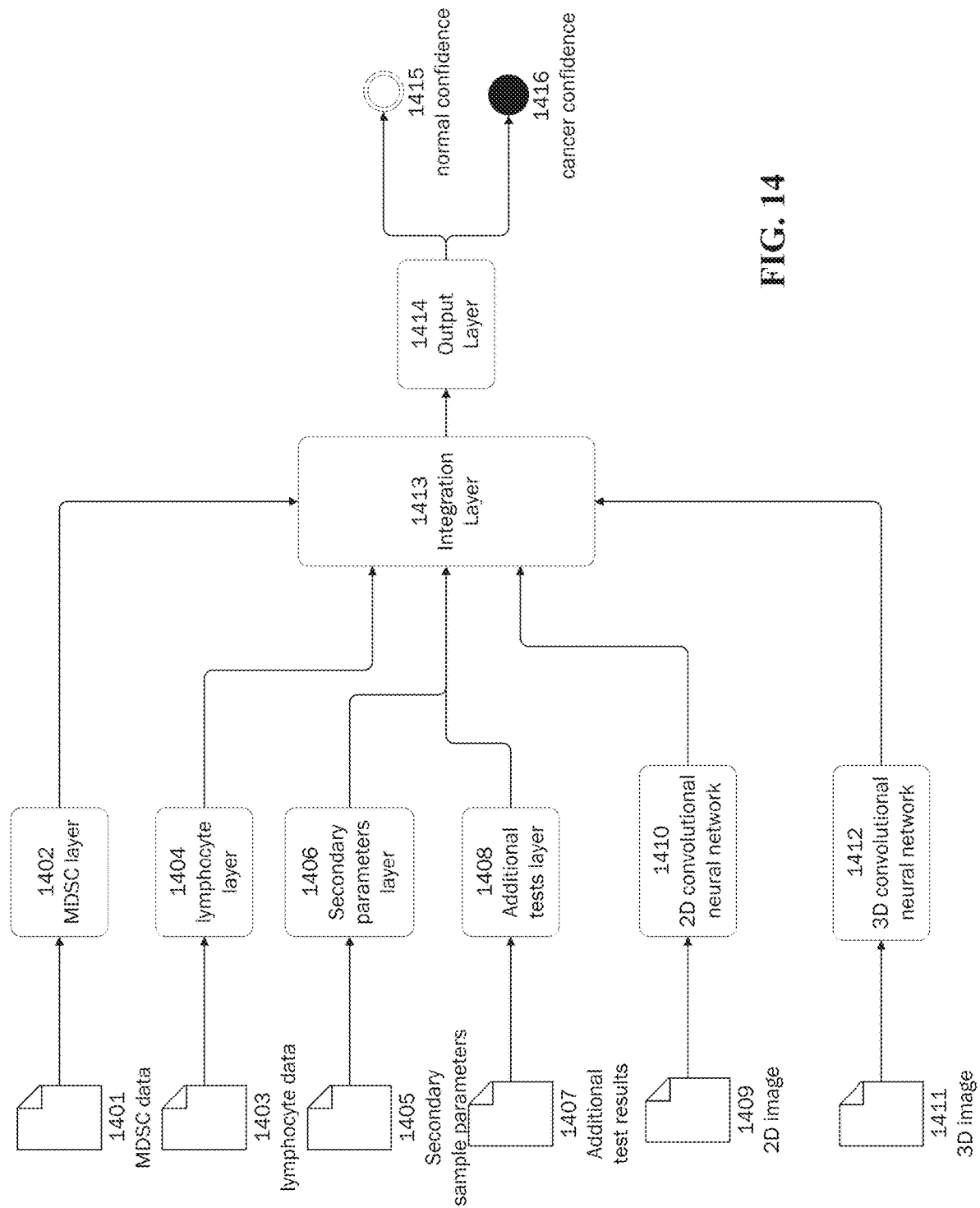
FIG. 14 illustrates an enhanced neural network for analyzing additional diagnostic indicators and types of input in addition to flow cytometry data.

As shown in FIG. 14, neural network hypervoxel distribution analysis of flow cytometry data can be combined with other forms of diagnostic data to improve sensitivity and specificity. MDSC data 1401 and lymphocyte data 1403 are processed by MDSC layer 1402 and lymphocyte layer 1404 respectively. Layers 1402 and 1404 may be replaced by a master network including pre-trained neural networks as shown in FIG. 6B. Secondary parameters 1405, such as age and sex of the test subject, time from sample collection to centrifugation or other processing, flow cytometry instrument parameters, and other data germane to the test conditions may be provided to the neural network at 1406. Additional test results 1407 such as test results for PSA, PSMA-(prostate specific membrane antigen), CEA (Carcino-embryonic antigen), CA-125 (Cancer antigen 125), cancer antigen 19-9 (CA19-9), prolactin (PRL), hepatocyte growth factor (HGF), osteopenia (OPN), myeloperoxidase (MPO), tissue inhibitor of metalloproteinases 1 (TIMP-1), or other protein, nucleic acid and other biomarkers may also be provided to the neural network at 1408.

2D image data 1409 such as a lung X-ray or other X-ray or other 2D image data may be provided to a 2D convolutional neural network input 1410. The 2D CNN 1410 may be trained to recognize diagnostically useful features in x-rays, skin photographs, or other 2D image data. The output of CNN 1410 may be used as an additional input to the integration layer 1413 to assist in test sample classification by the output layer 1414 to non-tumor-bearing confidence 1415 or cancer confidence 1416.

3D image data 1411 such as a Computed Tomography (CT) scan or MRI, NMI, imaging, or other 3D image data may be provided to a 3D convolutional neural network input 1412. The 3D CNN 1412 may be trained to recognize diagnostically useful features in CT scans, MRI images, NMI images, or other 3D image data. The output of CNN 1412 may be used as an additional input to the integration layer 1413 to assist in test sample classification.

Multiplex Assays

Cancer protein biomarkers are substances whose relative quantity and/or localization may be different between tumor-bearing and non-tumor-bearing subjects. They are of significant interest since they can reveal prognostic, diagnostic, predictive, pharmacodynamics, and/or recurrence information. In a standard laboratory setting, an enzyme-linked immunosorbent assay (ELISA) is commonly used to measure the amounts of a specific protein biomarker present in a sample. ELISAs may be time consuming and laborious, especially when investigating several biomarkers, making them unfavorable for large screenings of numerous biomarkers. Commonly, the types of biomarkers measured in these assays are cytokines, chemokines, and/or growth factors which are found in a blood sample.

In order to improve upon detection efficiency, multiplex assays have been developed and allow for simultaneous analysis of numerous biomarkers. One type of such a multiplex assay utilizes a bead-based flow cytometric platform, which allows for the simultaneous detection of multiple biomarkers with greater efficiency, speed, and a larger dynamic detection range than traditional ELISAs. These platforms, such as the Bio-Plex® 200 or Luminex 200®, can be important tools in the clinical setting for use in screening and early detection, patient monitoring, and/or predicting treatment responses. Like ELISAs, these multiplex assays can be based upon the capture sandwich immunoassay format. In these assays, a blood sample can be incubated with capture antibody-coupled beads of interest and followed by incubation with a biotinylated-detection antibody and a streptavidin-reporter dye conjugate with in-between washing. The beads can be subsequently passed through an array reader which measures the fluorescence or other indicators of the bound reporter dye corresponding to the concentration.

Recently, Cohen et al. developed a blood test, called CancerSEEK, that is capable of detecting eight common cancer types by measuring the levels of circulating protein biomarkers and the number of mutations in cell-free DNA. Specifically, through multiplex analysis, they found that 8 out of the 39 proteins tested proved to be useful for discriminating cancer patients from non-tumor-bearing donors. Elevations of cancer antigen 125 (CA-125), carcinoembryonic antigen (CEA), cancer antigen 19-9 (CA19-9), prolactin (PRL), hepatocyte growth factor (HGF), osteopontin (OPN), myeloperoxidase (MPO), and/or tissue inhibitor of metalloproteinases 1 (TIMP-1) along with the presence of specific tumor mutations led to a positive CancerSEEK result. By combining the measurement of these biomarkers with the number of mutations found in cell-free DNA, this test can detect the presence of cancer and also can indicate the site of origin for the cancer. This may support the idea that known tumor biomarkers can be incorporated, at some level, into any viable early cancer detection assay.

The results of a multiplex assay of markers for proteins or other constituents in a biological sample or samples can be used as an additional input to an artificial neural network which also analyzes flow cytometry data to make a prediction of the category of the sample being analyzed. The results of the multiplex assay can be used in conjunction with or as an alternative to ELISA.

Network

In various embodiments, any system or component thereof described herein comprises and/or is operably connected to a computer network. In some instances, the computer network comprises one or more computers operably connected to one or more flow cytometry data storage systems. The flow cytometry data storage systems retain an archive of all samples acquired at a local site, wherein operably connected may be wireless or physical. In many implementations, the computer network comprises a plurality of computers and/or devices which are connected by physical or wireless means. A computer of the network may be located remotely from the acquisition device. In some instances, the computer network comprises one or more acquisition computers for controlling the acquisition of a flow cytometry sample. In exemplary embodiments, the computer network is configured to control the acquisition of flow cytometry data acquired locally, wherein the data may be saved or exported directly from the acquiring flow cytometer instrument. In some instances, the network comprises one or more displays for viewing the acquired data. In some embodiments, one or more of the displays is a component of a viewing terminal of the network. A viewing terminal may be located remotely from the acquisition device. A computer, in various implementations, comprises software. In some embodiments, the computer network comprises the internet. In some embodiments, the computer network comprises a web browser.

Multiple client location terminals may perform any of the methods described herein. The central system server manages operations and distributes and updates the convolutional neural network model software or other neural network model software used at the terminals. The central system server will receive and store flow cytometry data, patient status, and test result data from the client terminals. Flow cytometry data from all clients can be used to continually re-train a convolutional or other neural network model at the server. Improvements to the model may result in an updated convolutional or other neural network model being distributed to the client terminals. In this way, all data available to the system as a whole can be used to optimize the deep learning convolutional or other neural network image analysis model.

In some embodiments, a computing system comprises one or more client systems and a server. Each client system is connected via the internet to the server. In some embodiments, any flow cytometry data of interest and their classification findings are transmitted to the server by the client system. At least some of the most interesting flow cytometry data is uploaded, from both non-tumor-bearing and cancer patients. In some embodiments, the server has a multiple-core GPU or a very powerful neural network training hardware configuration. Follow-up information is maintained on patients, and if their condition changes, that information is used to refine the classification capability of the central model. For example, if a patient goes from non-tumor-bearing to stage I cancer, at a subsequent blood test, the previous flow cytometry data can start to form a new classification, e.g., "previously non-tumor-bearing patient now having a positive diagnosis".

When the central model is sufficiently improved, it can be distributed as the next rev to the client system, after having received FDA approval, if necessary.

MDSC Enumeration from Patient Samples

In some embodiments, MDSC is used for analysis. The process is as follows. The process begins with diluting blood 1:1 with 2% fetal bovine serum (FBS) in phosphate buffered solution (PBS). A preferred embodiment uses 5 milliliters (mL or ml) of blood from a 10-mL sample that has been collected. Then, dispense 3.5 mL of Ficoll Plaque Plus into a 15 ml Filtration tube. Next, carefully layer 10 mL of diluted blood with PBS. It follows by spinning for 10 minutes (min) at 1,200 gravitational constants (x g) at room temperature. A collection of peripheral blood mononuclear cell (PBMC) layer is performed by scraping white blood cells (WBCs) near top of filter using a 1-mL pipet tip and pouring liquid into new 15-mL tube. The process further fills new 15-mL tube with cells to the top with 2% FBS, spins at 1700 revolutions per minute (rpm) for 5 min in a 40×g centrifuge, pours supernatant into the waste, and re-suspends pellet in 1 mL of magnetic-activated cell sorting (MACS) buffer. The tube is filled to top with MACS buffer, and spins at 1700 rpm for 5 min in a 40×g centrifuge. The process further pours supernatant into waste and re-suspend pellet in 1 mL of MACS buffer. Then, a new 1.5-mL Eppendorf tube is used to prepare enumeration of PBMC by dispensing 90 microliters (µl or µL) of PBS and 100 µL of Trypan Blue into tube. Then, 10 µL of cell mixture is added to the tube and invert several times, followed by loading 10 µl, into cell counter, repeating and averaging the two readings. In some embodiments, the readings multiply final average number by 10 to account for dilution, where cell counter compensates for other part of dilution. A determination on required volume of MACs buffer is performed to achieve a cell concentration of $5.0 \times 10^6$ PBMCs per mL (See example calculation below). The process may dispense 100 µl of cell mixture into the MDSC and MDSC Neg tubes, vortex quickly, store at 4° C. for >15 min, and fill tubes to the top with PBS and centrifuge sample at 1700 rpm for 5 min in 4° C. centrifuge. Finally, throw out supernatant in waste and resuspend each tube with 125 uL of DAPI buffer, and run flow cytometry.

In some embodiments, sample calculation is: $V1 \times C1 = V2 \times C2$. For instance, if the number of live cells in cell counter is $8.1 \times 10^5$ then $(8.1 \times 10^5) \times 10 = 8.1 \times 10^6$, where the multiplication by 10 accounts for dilution. 1 mL×8.1× $10^6$ cells per milliliter is equal to Z mL×5.0×10⁶. Then Z is equal to 1.62. Finally, Z deducts 1.0 mL to determine that 0.62 mL are currently suspended in. That means, the process may add 0.62 mL to current sample of cells to achieve desired concentration. If Z is less than 1, then V1×C1=V2× C2 spin down again at a speed (e.g., up to 1000 rpm, 1100 rpm, 1200 rpm, 1300 rpm, 1400 rpm, 1500 rpm, 1600 rpm, 1700 rpm, or 1800 rpm) for a period (e.g., 1 min, 2 min, 3 min, 4 min, 5 min, 6 min, 7 min, 8 min, 9 min, or 10 min), followed by discarding supernatant and resuspending in appropriate amount of MACs buffer.

Digital Processing Device

In some embodiments, the platforms, systems, media, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones (e.g., iPhone or Android phone), tablet computers (e.g., iPad), personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and may require power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 12:
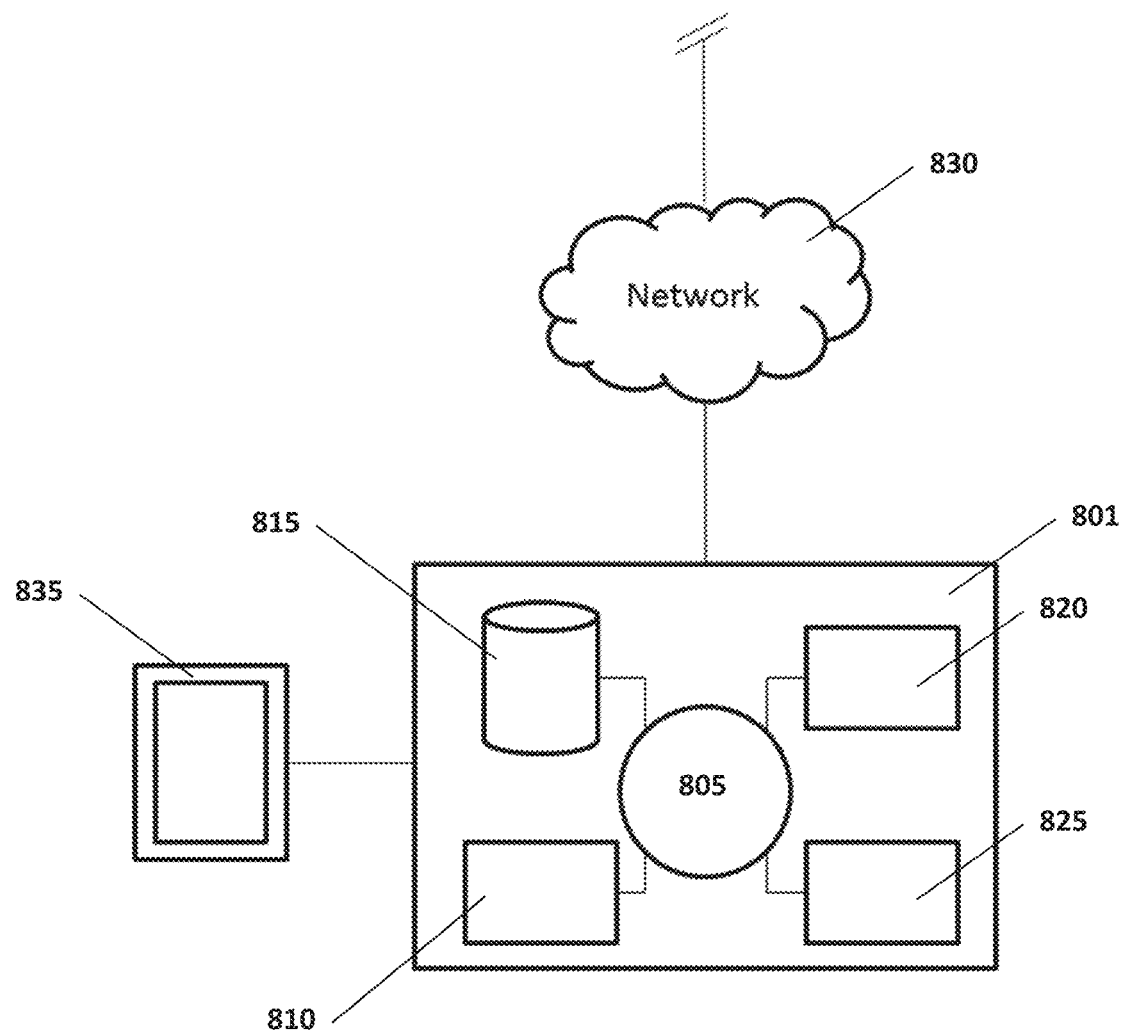
FIG. 12 illustrates an example of a computing system for analyzing flow cytometry data.

Referring to FIG. 12, in a particular embodiment, an exemplary digital processing device 801 is programmed or otherwise configured to perform flow cytometry data analysis. The device 801 can be connected to a flow cytometry instrument 835 or a measurement device. The device 801 can regulate various aspects of the data analysis of the present disclosure, such as, for example, convolutional neural networks. In this embodiment, the digital processing device 801 includes a central processing unit (CPU, also "processor" and "computer processor" herein) 805, which can be a single core or multi core processor, or a plurality of processors for parallel processing. The digital processing device 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The digital processing device 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the device 801, can implement a peer-to-peer network, which may enable devices coupled to the device 801 to behave as a client or a server.

Continuing to refer to FIG. 12, the CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and write back. The CPU 805 can be part of a circuit, such as an integrated circuit. One or more other components of the device 801 can be included in the circuit. In some cases, the circuit is an application specific integrated circuit (ASIC) or a field programmable gate array (FPGA).

Continuing to refer to FIG. 12, the storage unit 815 can store files, such as drivers, libraries and saved programs. The storage unit 815 can store user data, e.g., user preferences and user programs. The digital processing device 801 in some cases can include one or more additional data storage units that are external, such as located on a remote server that is in communication through an intranet or the Internet.

Continuing to refer to FIG. 12, the digital processing device 801 can communicate with one or more remote computer systems through the network 830. For instance, the device 801 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

Non-Transitory Computer Readable Storage Medium

In some embodiments, the platforms, systems, media, and methods disclosed herein comprise one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are, available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS Browser, Mozilla® Firefox for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of flow cytometry information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

System Operation

Figure 13:
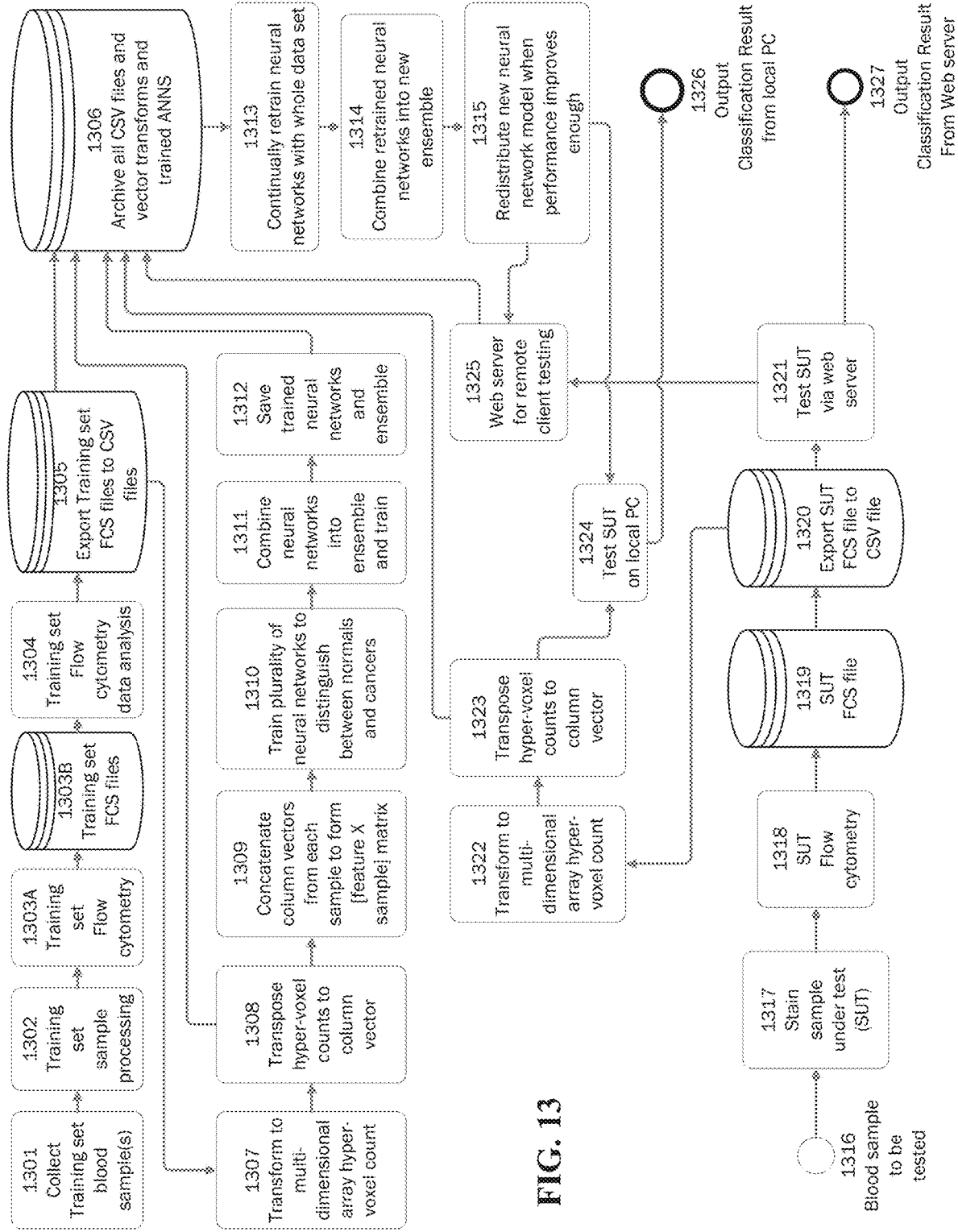
FIG. 13 illustrates an overall system operation of a diagnostic test system utilizing methods disclosed herein.

FIG. 13 shows one embodiment of a system employing artificial neural networks for cancer diagnosis utilizing methods disclosed herein. First, the system can be trained using a training database of samples. Accordingly, a set of blood samples is acquired from a set of non-tumor-bearing sample subjects and a set of known cancer patients 1301. These samples can be classified into as many categories as are desired, as long as there are a sufficient number of samples in each category for the ANN to train with sufficient accuracy to meet the sensitivity and specificity goals of the system. The required number of samples can be determined by repeatedly training the system with an increasing number of samples of each category in the training set until sensitivity and specificity no longer improve significantly as more samples are added. In this type of ANN application, the number of samples needed may be somewhere between 50 and 150.

The set of samples acquired may be centrifuged and stained 1302 according to the staining protocols disclosed above, or similar protocols appropriate to prepare samples for MDSC and if desired, lymphocyte flow cytometry analysis (e.g., as is known in the art). Flow cytometry analysis is performed on the samples 1303A on a flow cytometer instrument such as a BD Biosciences FACSCelesta™ or other flow cytometer. The flow cytometer will output data files in the FCS format or other appropriate format 1303B which are then processed using flow cytometry data analysis software 1304. Flow cytometry data analysis programs that run on a PC under Windows or MacOS operating systems that are suitable and commercially available include FlowJo™ by FlowJo, LLC, FCS Express™ by De Novo Software, or Kaluza Analysis Software™ by Beckman Coulter Life Sciences. The FCS files are manually or preferably automatically gated to yield the live cell subset of events as described above. The live cell populations are then exported to a data repository 1305 in a standard format such as Comma Separated Variable (CSV).

A software algorithm 1307 then converts a predetermined number of live cell events such as 10,000 to 50,000 live cell events to hypervoxel counts as described above. The hypervoxel counts are initially stored in a hyperdimensional array and are then converted to a column vector 1308 for each of the sample data spaces being used (e.g., 7-D MDSC, 6-D lymphocyte, or other cell population or populations). This software can be written in any appropriate software language such as C, C++, Python, Ruby or other language or may be developed in a development SDK environment such as Matlab, as is well known in the art. The column vectors thus generated from each sample in a data space are then saved in a data repository 1306 and also concatenated creating a 2 dimensional matrix having a row for each hypervoxel and a column for each sample 1309. Additional data may be added for each sample such as age, sex, collection conditions, etc. A target vector is also prepared which identifies the cancer status or non-tumor-bearing status of each sample to be used in training.

The sample database thus acquired is divided into at least three sample sub-databases. The first sample sub-database is used to train a plurality of primary ANNs 1310. The second sample sub-database is used for final evaluation and ranking of the trained primary ANNs. When a sufficient number, typically 3 to 20, of primary ANNs have been trained to the desired degree of sensitivity and specificity as determined by testing them on the evaluation sample sub-database, they are incorporated into a master ANN ensemble 1311 which is then trained on the third sample sub-database. Once the master ANN is trained to the desired specificity and sensitivity, it is saved 1312 in archive 1306.

The ANN may need to be approved by the United States Food and Drug Administration (U.S. FDA). When appropriate, the trained ANN is deployed 1315 to remote test personal computers (PCs) 1324 for on-site testing at remote locations, such as hospitals and clinics, and is installed on a web server 1325 for online testing.

At remote sites where it is desired to perform this diagnostic test, blood samples are obtained from the test subject 1316. These samples may be centrifuged stained locally at a remote clinic 1317, or the sample may be shipped to a centralized location for processing (not shown). Flow cytometry is performed on the sample 1318 and the flow cytometer data is saved 1319, exported to comma-separated values (CSV) format 1320, transformed and transposed 1322 and 1323, and tested with the previously trained and deployed on a local PC 1324, or alternatively the CSV file is uploaded to a web server 1325 for testing to be performed online 1321. Test results are then provided either from the local PC 1326 or from the web server 1327.

Whether testing is performed locally or online, the sample data is uploaded to archive 1306. When a confirmed diagnosis is available for a sample, the sample is included in an expanded data set that is used to continually retrain neural networks 1313 with the continually increasing data set. ANN performance will continue to improve due to the increased sample size. The retrained neural networks can be combined into the new ensemble 1314. When performance has improved sufficiently, the new ANN can be "frozen" and redeployed as the next version of test network 1315.

Exemplary Embodiments

Among the embodiments provided herein are:
1. A computer-implemented method of training an artificial neural network, the method comprising: (a) performing, by a computer, an augmentation process comprising: (1) obtaining a biological data sample comprising measurements from a flow cytometer instrument of a plurality of event features for a plurality of events of interest of a biological sample; (2) generating a sub-sample, wherein the generating comprises selecting measurements of event features from a subset of the events of interest from the biological data sample; and (b) applying, by the computer, a training process to an artificial neural network, wherein the training process comprises analyzing the sub-sample. 2. The method of embodiment 1, wherein the artificial neural network is capable of continually training. 3. The method of embodiment 1, wherein step (a) further comprises: using four or more flow cytometer measurement channels to define a feature coordinate space, the feature coordinate space comprising four or more axes, each axis corresponding to a different channel of the four or more flow cytometer measurement channels, wherein each of the four or more flow cytometer measurement channels produces measurements of the event features of the sub-sample, and using the measurements of the event features of the sub-sample to define locations for the subset of events of interest in the feature coordinate space to form a distribution in the feature coordinate space indicative of an event population of interest, wherein the distribution in the feature coordinate space indicative of the event population of interest is formed by: (i) dividing each axis of the feature coordinate space into a plurality of segments, thereby dividing the coordinate space into a plurality of hypervoxels, and (ii) for each hypervoxel of the plurality of hypervoxels, determining a count of a number of events of interest comprising an event feature value that locates the event of interest in the hypervoxel. 4. The method of embodiment 1, comprising repeating step (a)(2) at least one time to generate sibling samples, wherein the sibling samples are at least two sub-samples generated from the biological data sample. 5. The method of embodiment 4, wherein the sibling samples comprise a first sibling sample and a second sibling sample, wherein the first sibling sample has a different subset of the events of interest than the second sibling sample. 6. The method of embodiment 4, wherein the sibling samples comprise a first sibling sample and a second sibling sample, wherein the first sibling sample comprises a number (N) of measurements of the biological sample and a second sibling sample, wherein the second sibling sample comprises at least N/4 measurements of the biological sample. 7. The method of embodiment 6, wherein the number (N) of measurements comprises at least 5,000 events. 8. The method of embodiment 6, wherein the number (N) of measurements is between 5,000 to 100,000 events. 9. The method of embodiment 1, wherein the method improves a performance characteristic of the artificial neural network in detecting a condition in the biological sample, wherein the performance characteristic comprises at least one of a sensitivity and a specificity of detecting the condition in the biological sample, by at least 0.1% as compared to a sensitivity and a specificity of detecting the condition in the biological sample without the augmentation process. 10. The method of embodiment 1, wherein: the augmentation process (a) further comprises: obtaining a second biological data sample comprising measurements from a flow cytometer instrument of a plurality of event features for a plurality of events of interest of a second biological sample; generating a sub-sample of the second biological data sample, wherein generating comprises selecting measurements of event features from a subset of the events of interest from the second biological data sample; and the training process further comprises analyzing the sub-sample of the second biological data sample. 11. The method of embodiment 1, further comprising: (c) determining a status of a condition in a subject by applying, by the computer, the artificial neural network to data obtained from a naïve biological sample from the subject, wherein the data comprise a plurality of event features for a plurality of events from the subject; and (d) generating, by the computer, a report comprising the status of the condition in the subject. 12. The method of embodiment 3, further comprising: (c) determining a status of a condition in a subject by applying, by the computer, the artificial neural network to data obtained from a naïve biological sample from the subject, wherein the data comprise a plurality of event features for a plurality of events from the subject; and (d) generating, by the computer, a report comprising the status of the condition in the subject. 13. The method of embodiment 12, further comprising applying, by the computer, an artificial neural network detection structure to the distribution in the feature coordinate space indicative of the event population of interest, the detection structure employing an artificial neural network to correlate the distribution in the feature coordinate space indicative of the event population of interest with a distribution in a reference feature coordinate space indicative of a reference event population. 14. The method of embodiment 12, wherein determining the status of the condition in the subject further comprises determining, by the computer, whether the biological sample contains cells indicative of the condition in the subject. 15. The method of embodiment 12, further comprising identifying, by the computer, characteristic cell features of cells indicative of the condition. 16. The method of embodiment 12, further comprising using the status of the condition in the subject and cell feature data to further train the artificial neural network. 17. The method of embodiment 11, wherein the status of the condition comprises a presence of the condition, an absence of the condition, an increase in severity of the condition, a decrease in severity of the condition, a stage of the condition, a status associated with a prognosis, or a response to a therapy. 18. The method of embodiment 1, wherein the training process in (b) further comprises updating the artificial neural network to improve a performance characteristic of the artificial neural network. 19. The method of embodiment 1, wherein the method improves a performance characteristic of the artificial neural network in detecting a condition in the biological sample, wherein the performance characteristic comprises at least one of a sensitivity and a specificity of detecting the condition in the biological sample by at least 0.1% as compared to a sensitivity and a specificity of detecting the condition in the biological sample without the augmentation process. 20. The method of embodiment 2, wherein a sibling sample is used for one of training, validating, and testing during the training process of the artificial neural network. 21. The method of embodiment 4, wherein the sibling samples are used for one of training, validating, and testing during the training process of the artificial neural network. 22. The method of embodiment 1, wherein the artificial neural network is a previously trained artificial neural network. 23. The method of embodiment 1, wherein selecting measurements of event features from the subset of the events of interest from the biological data sample comprises randomly selecting a measurement of an event feature from the subset of events of interest. 24. The method of embodiment 1, wherein the augmentation process is performed in at least two successive training processes of the artificial neural network. 25. The method of embodiment 24, wherein an additional sibling sample is generated for an additional successive training process of the artificial neural network. 26. The method of embodiment 25, wherein the additional sibling sample is generated for every M artificial neural networks trained, wherein M is at least 5. 27. The method of embodiment 25, wherein the additional sibling sample is generated for every M artificial neural networks trained, wherein M is between 3 and 30. 28. The method of embodiment 1, wherein the artificial neural network comprises a convolutional neural network. 29. The method of embodiment 3, further comprising applying a dimensionality reduction algorithm to the feature coordinate space to (a) generate a computed coordinate space and (b) map each of the plurality of events of interest from a location in the feature coordinate space to a corresponding location in the computed coordinate space. 30. The method of embodiment 29, wherein the dimensionality reduction algorithm comprises a principal component analysis. 31. The method of embodiment 1, wherein the events of interest comprise one or more cells, the event features comprise one or more cell features, and the event population of interest comprises one or more cell populations of interest. 32. The method of embodiment 31, wherein the one or more cell features are selected from the group consisting of a morphological feature, a cell marker, a protein concentration, a lipid content, an axial light loss, an optical phase, an optical loss, and combinations thereof; and wherein the one or more cell populations of interest are selected from the group consisting of polymorphonuclear myeloid derived suppressor cells (PMN-MDSCs), monocytic MDSCs (M-MDSCs), early-stage MDSCs (e-MDSCs), granulocytic MDSCs (g-MDSCs), and combinations thereof. 33. A computer-implemented method of using a trained artificial neural network to determine a status of a condition of a subject, the method comprising: (a) performing, by a computer, an analysis of a biological sample from a subject, the analysis comprising: (1) obtaining a biological data sample comprising measurements obtained from a flow cytometer instrument of a plurality of event features for a plurality of events of interest from the biological sample; (b) determining a status of a condition of the subject by applying, by the computer, an artificial neural network to the biological data sample. 34. The method of embodiment 33, the method further comprising performing, by the computer, an augmentation process comprising: (a)(2) generating a sub-sample, wherein the generating comprises selecting measurements of event features from a subset of the events of interest; and (a)(3) repeating step (a)(2) to generate sibling samples, wherein the sibling samples are two or more sub-samples from the biological data sample. 35. The method of embodiment 34, wherein step (a) further comprises: using four or more flow cytometer measurement channels to define a feature coordinate space, the feature coordinate space comprising four or more axes, each axis corresponding to a different channel of the four or more flow cytometer measurement channels, wherein each of the four or more flow cytometer measurement channels produces measurements of the event features of the sub-sample, and using the measurements of the event features of the sub-sample to define locations for the subset of events of interest in the feature coordinate space to form a distribution in the feature coordinate space indicative of an event population of interest, wherein the distribution in the feature coordinate space indicative of the event population of interest is formed by: (i) dividing each axis of the feature coordinate space into a plurality of segments, thereby dividing the coordinate space into a plurality of hypervoxels, and (ii) for each hypervoxel of the plurality of hypervoxels, determining a count of a number of events of interest comprising an event feature value that locates the event of interest in the hypervoxel. 36. The method of embodiment 35, further comprising applying a dimensionality reduction algorithm to the feature coordinate space to (a) generate a computed coordinate space and (b) map each of the plurality of events of interest from a location in the feature coordinate space to a corresponding location in the computed coordinate space. 37. The method of embodiment 36, wherein the dimensionality reduction algorithm comprises a principal component analysis. 38. The method of embodiment 33, wherein the events of interest comprise one or more cells, the event features comprise one or more cell features, and the event population of interest comprises one or more cell populations of interest. 39. The method of embodiment 38, wherein the one or more cell features are selected from the group consisting of a morphological feature, a cell marker, a protein concentration, a lipid content, an axial light loss, an optical phase, an optical loss, and combinations thereof; and wherein the one or more cell populations of interest are selected from the group consisting of polymorphonuclear myeloid derived suppressor cells (PMN-MDSCs), monocytic MDSCs (M-MDSCs), early-stage MDSCs (e-MDSCs), granulocytic MDSCs (g-MDSCs), and combinations thereof. 40. The method of embodiment 33, wherein applying comprises comprising applying, by the computer, an artificial neural network detection structure to the distribution in the feature coordinate space indicative of the event population of interest, the detection structure employing an artificial neural network to correlate the distribution in the feature coordinate space indicative of the event population of interest with a distribution in a reference feature coordinate space indicative of a reference event population. 41. The method of embodiment 33, wherein determining the status of the condition in the subject further comprises determining, by the computer, whether the biological sample contains cells indicative of the condition in the subject. 42. The method of embodiment 33, further comprising identifying, by the computer, characteristic cell features of cells indicative of the condition. 43. The method of embodiment 33, wherein the artificial neural network is capable of continually training. 44. The method of embodiment 33, further comprising using the status of the condition in the subject and cell feature data to further train the artificial neural network. 45. The method of embodiment 34, wherein the sibling samples comprise a first sibling sample and a second sibling sample, wherein the first sibling sample comprises a number (N) of measurements of the biological sample and the second sibling sample comprises at least N/4 measurements of the biological sample. 46. The method of embodiment 45, wherein the number (N) of measurements is at least 5,000 events. 47. The method of embodiment 45, wherein the number (N) of measurements is between 5,000 and 100,000 events. 48. The method of embodiment 34, wherein a plurality of sibling samples are tested by the artificial neural network, wherein the testing provides a status of a condition, wherein the status of the condition indicates a presence or an absence of a disease condition. 49. The method of embodiment 34, wherein the status of the condition of a first sibling sample of a plurality of sibling samples is determined independently of the status of the condition of a second sibling sample of the plurality of sibling samples from the same biological data sample, wherein the statuses of the condition for the plurality of the sibling samples are provided by the same artificial neural network. 50. The method of embodiment 34, wherein the artificial neural network provides the status of the condition for at least three sibling samples from the same biological data sample to give a global status category of the biological data sample, wherein the global status category comprises the most probable category based on a frequency of the statuses of the condition of the sibling samples. 51. The method of embodiment 34, wherein the artificial neural network is one of at least three artificial neural networks that are used by a master network where the at least three artificial networks vary in at least one of number of network layers, number of neurons used, training function, method of output error calculation, weight and bias updating method, number of inputs, type of inputs, and combinations thereof. 52. The method of embodiment 33, the method further comprising (c) identifying, by the computer, characteristic event features indicative of the status of the condition, thereby providing the status of the condition of the biological data sample and diagnosing the status of the condition in the subject. 53. The method of embodiment 52, the method further comprising (d) automatically generating, by the computer, a report comprising the status of the condition and a treatment recommendation for the status of the condition in the subject, wherein the generating is based on characteristic event features indicative of the status of the condition. 54. The method of embodiment 33, wherein the artificial neural network is a previously trained artificial neural network. 55. The method of embodiment 34, wherein the selecting measurements of event features from a subset of the events of interest comprises randomly selecting a measurement of an event feature from the subset of events of interest. 56. The method of embodiment 33, wherein the status of the condition comprises a presence of the condition, an absence of the condition, an increase in severity of the condition, a decrease in severity of the condition, a stage of the condition, a status associated with a prognosis, or a response to a therapy. 57. The method of embodiment 33, wherein multiple artificial neural networks are applied to the biological data sample and used to provide multiple statuses of the condition, wherein the multiple artificial neural networks are trained separately, wherein the multiple artificial neural networks provide an independent status of the condition. 58. The method of embodiment 57, wherein the statuses of the condition by the multiple artificial neural networks are analyzed by a master neural network to give a global status category of the biological sample, wherein the global status category is the most probable category based on a frequency of the statuses of the condition of the biological data sample. 59. The method of embodiment 58, wherein the multiple artificial neural networks used by the master neural network vary in number of network layers, number of neurons used, training function, method of output error calculation, weight and bias updating method, number of inputs, type of inputs, or combinations thereof 60. The method of embodiment 33, wherein the artificial neural network comprises a network output classifier, the network output classifier comprising a sigmoid activation function, wherein the sigmoid activation function comprising a network sigmoid output value over a threshold is classified into a first status and the value at or below the threshold is classified into a second status. 61. The method of embodiment 60, wherein the threshold is between 0.3 and 0.7. 62. The method of embodiment 61, wherein the threshold is 0.5. 63. The method of embodiment 60, wherein a transformation is applied, the transformation rescaling the network sigmoid output value to give the status of the condition for a chosen threshold. 64. The method of embodiment 60, wherein the network output classifier is adjusted to improve at least one of sensitivity and specificity of the biological sample by at least 0.1% as compared to classification without the network output classifier adjustment. 65. The method of embodiment 33, wherein the analysis of the biological sample from the subject further comprises: (a)(2) grouping the measurements of the plurality of event features into a plurality of bins, a bin representing a subset associated with a range of measured values; (a)(3) applying a filter to the plurality of bins, wherein application of the filter comprises: (i) identifying the bins populated with no measurements and the bins populated with measurements of undesired event features; and (ii) creating a biological data sample of desired bins, wherein the bins identified in (i) are removed from the biological data sample prior to training the artificial neural network. 66. The method of embodiment 65, wherein a number of the plurality of bins in the biological data sample is reduced by at least 50%. 67. A computer-implemented method of applying an artificial neural network to a biological data sample from a biological sample from a subject to generate a status of a condition and a treatment recommendation, the method comprising: (a) performing, by a computer, analysis of a biological data sample from a biological sample from a subject, the analysis comprising: (1) obtaining the biological data sample from measurements obtained from a flow cytometer instrument of a plurality of event features for a plurality of events of interest in the biological sample; (b) applying, by the computer, an artificial neural network to the biological data sample, wherein the artificial neural network provides a status of a condition in the subject. 68.The method of embodiment 67, wherein the method further comprises automatically generating, by the computer, a report comprising the status of the condition in the subject. 69. The method of embodiment 67, wherein the method further comprises generating, by the computer, a treatment recommendation for the condition in the subject, wherein the generating is based on identification of cell features indicative of the condition. 70. The method of embodiment 67, wherein the status of the condition comprises a presence of the condition, an absence of the condition, an increase in severity of the condition, a decrease in severity of the condition, a stage of the condition, a status associated With a prognosis, or a response to a therapy. 71. The method of embodiment 67, wherein the biological data sample comprises measurements from the biological sample from the subject collected at a first time point and wherein the method further comprises repeating steps (a) and (b) on at least a second biological sample from the subject collected at one or more subsequent time points. 72. The method of embodiment 71, wherein the status of the condition collected at the first time point provides a baseline status of the subject and the status of the condition of the second biological sample is monitored for a change from the baseline status. 73. The method of embodiment 71, wherein the baseline status indicates a diagnosis of the condition in the subject and the status of the condition of the second biological sample is used to monitor a response of the subject to a treatment for the condition in the subject, wherein the response is used to adjust the treatment, wherein the adjusting the treatment comprises changing a dose, frequency, type of treatment, or combination thereof. 74. The method of embodiment 67, wherein the artificial neural network further provides a prediction of a response of the subject to a treatment based on the analysis of the biological data sample. 75. The method of embodiment 67, wherein the artificial neural network is capable of continually training. 76. The method of embodiment 67, wherein the artificial neural network is a previously trained artificial neural network. 77. The method of embodiment 67, wherein providing a status of a condition in the subject comprises providing a diagnosis. 78. The method of embodiment 67, wherein the condition comprises cancer, diabetes, Parkinson's disease, Alzheimer's disease, pancreatitis, multiple sclerosis, hepatitis, tuberculosis, or HIV, or combinations thereof. 79. The method of embodiment 67, wherein the method is performed in conjunction with a screening test for the condition. 80. The method of embodiment 79, wherein the screening test comprises a mammogram, a rectal exam, a prostate-specific antigen test, a computed tomography, an X-ray, or combinations thereof. 81. The method of embodiment 67, wherein the method further comprises a DNA sequencing diagnostic test for the condition, wherein the DNA sequencing diagnostic test identifies the status of the condition or mutations indicative of the condition. 82. The method of embodiment 67, wherein the method further comprises assessing the events for biomarkers of the condition. 83. The method of embodiment 67, wherein the biological data sample further comprises data of a result of a biomarker assay, wherein the biomarker assay detects biomarkers of the condition. 84. The method of embodiment 67, wherein the artificial neural network comprises a convolutional neural network. 85. A computer-implemented method of updating an artificial neural network for generating a status of a condition of a biological sample, the method comprising:(a) obtaining a biological data sample, the biological data sample comprising measurements obtained from a flow cytometer instrument of a plurality of event features for a plurality of events of interest in a biological sample; (b) performing, by a computer, an analysis of measurements of the biological sample, the analysis comprising applying, by the computer, a training process to an artificial neural network; (c) updating the artificial neural network by iteratively performing steps (a) and (b) with a biological data sample from at least one additional biological sample. 86. The method of embodiment 85, wherein the method further comprises using the updated artificial neural networks to provide a status of a condition of at least one additional biological sample. 87. The method of embodiment 86, wherein the method further comprises automatically generating, by the computer, a report comprising the status of the condition. 88. The method of embodiment 86, wherein the method further comprises generating, by the computer, a treatment recommendation for the condition, wherein the generating is based on identification of the event features indicative of the condition. 89. The method of embodiment 85, wherein the updating of the artificial neural network occurs on a continual basis. 90. The method of embodiment 85, wherein the at least one additional biological sample comprises at least 100 biological data samples. 91. The method of embodiment 85, wherein the method is performed at least one time a year. 92. The method of embodiment 85, wherein the updating adds biological data samples from one or more biological samples to the training process. 93. The method of embodiment 85, wherein the method further comprises performing an augmentation process to the biological data sample to generate a sub-sample before performing the analysis of measurement, wherein generating comprises selecting measurements of event features from the events of interest from the biological data sample. 94. A computer-implemented method of updating an artificial neural network for a status of a condition of a biological sample, the method comprising: (a) obtaining a biological data sample, the biological data sample comprising measurements obtained from a flow cytometer instrument of a plurality of event features for a plurality of events of interest in a biological sample; (b) performing an augmentation process on the biological data sample to generate a sub-sample before performing the analysis of measurement, wherein generating comprises selecting measurements of event features of the events of interest from the biological data sample; (c) performing, by a computer, analysis of the sub-sample, the analysis comprising applying, by the computer, a training process to an artificial neural network; (d) updating the artificial neural network by iteratively performing steps (a) to (c) with at least one additional biological data sample. 95. The method of embodiment 94, wherein the method further comprises using the updated artificial neural network to provide a status of a condition of the biological data sample. 96. The method of embodiment 94, wherein updating the artificial neural network occurs on a continual basis. 97. The method of embodiment 94, wherein the method further comprises automatically generating, by the computer, a report comprising a medical diagnosis. 98. The method of embodiment 94, wherein the method further comprises generating, by the computer, a treatment recommendation for the condition, wherein the generating is based on identification of the event features indicative of a condition. 99. The method of embodiment 94, wherein the at least one additional biological data sample comprises at least 100 biological data samples. 100. The method of embodiment 94, wherein the updating is performed at least one time a year. 101. The method of embodiment 94, wherein the updating adds biological data samples from one or more biological samples to the training process.

EXAMPLES

Example 1

MDSC Detection

Populations of MDSCs are identified in patients with cancer by flow cytometry and convoluted neural networks.

A peripheral blood sample from a patient with cancer is taken. The blood sample is centrifuged to pellet the cells. The cells are resuspended to a concentration of $10^7$ cells/mL (cells per mL) in Phosphate Buffer Solution (PBS).

Cells are then labeled with anti-human monoclonal antibodies. Antibodies that are used include anti-lineage-FITC (fluorescein isothiocyanate), including anti-CD3, -CD14, -CD16, -CD19, -CD20 and -CD56, anti-CD33-PE, anti-HLA-DR-ECD, anti-CD11b-PE-Cy5, anti-CD14-PE, anti-CD15-PE-Cy5, anti-CD33-PE-Cy7. Cells are then analyzed by flow cytometry with at least $4\times10^4$ events acquired for analysis.

Following the initial FSC/SSC discrimination, the gate is set on DR$^-$/LIN$^-$ cells. Subpopulations are then gated to identify MDSCs, including CD14$^-$, CD11b$^+$, CD15$^+$, CD66$^+$, CD14$^+$, CD15$^-$, and their combinations.

The Matlab 2016b matrix calculation software was used to perform the calculations. The Matlab Neural Network Toolbox and Parallel Computing Toolbox were used for proof of principle calculations. The Bayesian regularization backpropagation produced the best results. The model was trained using 15 normals (e.g., non-tumor-bearing subjects) and 25 cancers (e.g., subjects with cancer). The model automatically used the remaining samples in the model set (16 normals and 25 cancers) to test itself.

In some embodiments, additional technical elements are considered. For example, more dimensions (e.g., start with SSC-A) are taken into account; higher resolution is selected or one or more selected axes; using focused resolution for higher resolution in critical areas; create an ensemble architecture; perform dimension reduction of input vectors by principal component analysis; utilize k-means clustering; utilize self-organizing maps; train and test on a specific cancer type to derive optimal analysis architecture.

Results of Testing

In the model test set, the model had a specificity of 81.2% and a sensitivity of 80.0% (13/16 normals correct, 20/25 cancers correct). For all 81 samples in the model set, the model had a specificity of 90.3% and a sensitivity of 90.0% (28/31 normals correct, 45/50 cancers correct). The model was frozen and used to test the held out 4 cancers and 3 normals. 100% (7/7) tested correctly. Therefore, for new samples not used to train the model, it had a specificity of 84.2% (16/19) and a sensitivity of 82.7% (24/29). For the total sample set (81 model set +7 held out set (34 normals, 54 cancers) total=88 samples) the model had a specificity of 91.2% (31/34) and a sensitivity 90.7% (49/54).

Blood samples (e.g., biological samples) were obtained from 31 non-tumor-bearing donors (e.g., non-tumor-bearing subjects) and 50 cancer patients (e.g., subjects with cancer), shown in Tables 1 and 2, respectively.

TABLE 1

Non-tumor-bearing/Normal Donors

Total Healthy Donors: 31

| Sample ID | Date collected | Age | Sex |
|---|---|---|---|
| HD 134 | 29 Sep. 2016 | 39 | F |
| HD 31 | 29 Sep. 2016 | 52 | F |
| HD 501 | 29 Sep. 2016 | 61 | M |
| HD 323v2 | 30 Sep. 2016 | 57 | M |
| HD 469v2 | 5 Oct. 2016 | 59 | M |
| HD 452 | 12 Oct. 2016 | 70 | F |
| HD 462 | 12 Oct. 2016 | 67 | M |
| HD 310 | 17 Oct. 2016 | 48 | F |
| HD 13v2 | 19 Oct. 2016 | 52 | F |

TABLE 1-continued

Non-tumor-bearing/Normal Donors

Total Healthy Donors: 31

| Sample ID | Date collected | Age | Sex |
|---|---|---|---|
| HD 13v2 | 19 Oct. 2016 | 52 | F |
| HD 412 | 25 Oct. 2016 | 58 | F |
| HD 27 | 26 Oct. 2016 | 56 | M |
| HD 277 | 26 Oct. 2016 | 48 | F |
| HD 494 | 26 Oct. 2016 | 52 | M |
| HD 120 | 1 Nov. 2016 | 50 | F |
| HD 616 | 1 Nov. 2016 | 45 | F |
| HD 597 | 4 Nov. 2016 | 52 | M |
| HD 383 | 7 Nov. 2016 | 58 | M |
| HD 619 | 8 Nov. 2016 | 51 | F |
| HD 29 | 9 Nov. 2016 | 60 | F |
| HD 552 | 9 Nov. 2016 | 63 | N/A |
| HD 476 | 10 Nov. 2016 | 29 | F |
| HD 590 | 10 Nov. 2016 | 59 | F |
| HD 611 | 14 Nov. 2016 | 31 | F |
| HD 615 | 14 Nov. 2016 | 38 | F |
| HD 383v2 | 15 Nov. 2016 | 58 | M |
| HD 271 | 16 Nov. 2016 | 43 | M |
| HD 524v2 | 16 Nov. 2016 | 49 | F |
| HD 494v2 | 17 Nov. 2016 | 52 | M |
| HD 605 | 17 Nov. 2016 | 29 | F |
| HD 571 | 21 Nov. 2016 | 51 | F |

TABLE 2

Cancer Patients

Total Cancer Patients: 50

| Sample ID | Date collected | Cancer Type | Cancer Stage |
|---|---|---|---|
| VH-022 | 13 Sep. 2016 | Breast | |
| VH-027 | 22 Sep. 2016 | Breast | 2 |
| VH-028 | 22 Sep. 2016 | Breast | 1a |
| VH-030 | 22 Sep. 2016 | Breast | |
| TB-16-208 | 29 Sep. 2016 | Colon | |
| VH-033 | 29 Sep. 2016 | Breast | 1a |
| VH-034 | 29 Sep. 2016 | Breast | 2a |
| VH-035 | 3 Oct. 2016 | Breast | 1 |
| VH-036 | 3 Oct. 2016 | Breast | 0 |
| VH-037 | 4 Oct. 2016 | Breast | 2b |
| VH-038 | 5 Oct. 2016 | Breast | 1a |
| VH-039 | 5 Oct. 2016 | Breast | 3a |
| VH-040 | 5 Oct. 2016 | Liver | 4 |
| VH-043 | 7 Oct. 2016 | Pancreatic | 4 |
| TB-16-218 | 10 Oct. 2016 | Vulva | |
| VH-044 | 10 Oct. 2016 | Breast | |
| TB-16-222 | 11 Oct. 2016 | Vulva | |
| VH-045 | 11 Oct. 2016 | Cervix | 3b |
| TB430 | 12 Oct. 2016 | Breast | 3b |
| VH-046 | 12 Oct. 2016 | Esophagus | 3a |
| VH-047 | 12 Oct. 2016 | Breast | |
| TB431 | 13 Oct. 2016 | Breast | 4 |
| VH-048 | 13 Oct. 2016 | Breast | 1 |
| VH-049 | 14 Oct. 2016 | Breast | |
| VH-050 | 14 Oct. 2016 | Breast | 1 |
| TB-16-224 | 18 Oct. 2016 | Thyroid | |
| TB-16-228 | 19 Oct. 2016 | Tongue | |
| VH-051 | 20 Oct. 2016 | Breast | |
| VH-052 | 20 Oct. 2016 | Breast | |
| VH-053 | 24 Oct. 2016 | Breast | |
| TB-16-23 3 | 25 Oct. 2016 | Head and neck | |
| TB-16-234 | 25 Oct. 2016 | Breast | |
| TB-16-237 | 27 Oct. 2016 | Endometrial | |
| TB-16-239 | 1 Nov. 2016 | Head and neck | |
| TB-16-247 | 3 Nov. 2016 | Lung | |
| TB-16-248 | 4 Nov. 2016 | Colon | |
| TB-16-249 | 4 Nov. 2016 | Colon | |
| TB 16-254 | 7 Nov. 2016 | Breast | 2a |
| TB 16-256 | 9 Nov. 2016 | Lung | 4 |
| VH-054 | 14 Nov. 2016 | Breast | |

TABLE 2-continued

Cancer Patients

Total Cancer Patients: 50

| Sample ID | Date collected | Cancer Type | Cancer Stage |
|---|---|---|---|
| VH-055 | 15 Nov. 2016 | Breast | |
| TB 16-265 | 16 Nov. 2016 | Breast | 3b |
| TB 16-268 | 16 Nov. 2016 | Lung | 3b |
| VH-056 | 16 Nov. 2016 | Breast | |
| TB 16-270 | 17 Nov. 2016 | Lung | 4 |
| VH-057 | 18 Nov. 2016 | Breast | |
| VH-058 | 18 Nov. 2016 | Breast | |
| TB 16-273 | 21 Nov. 2016 | Lung | 2b |
| TB 16-274 | 21 Nov. 2016 | Brain | |
| VH-059 | 22 Nov. 2016 | Breast | |

Samples from non-tumor-bearing donors and cancer patients were qualified by requiring (1) a Live cell count of 40,000 or greater (2) correct staining and (3) correct compensation. All samples that met these criteria were used for training or testing. The flow cytometry data was manually gated to produce a population of Live cells as described above. 13 channels of data were available from the flow cytometry output FCS files. These were FSC-A, FSC-H, FSC-W, SSC-A, SSC-H, SSC-W, CD11b, CD14, HLA-DR, CD33, Lineage, DAPI, and CD15. Of these 13, 6 were selected for the first configuration for testing. These were CD11b, CD14, HLA-DR, CD33, Lineage, and CD15. Each axis was divided into 4 divisions as described above. This resulted in a 4×4×4×4×4×4 hypervolume. Counts were accumulated indicating how many of the 40,000 cells in each sample fell in each hypervoxel. The 4×4×4×4×4×4 hypervolume count values in each hypervoxel were then transformed into a 4,096×1 column vector for each sample. Of the 81 total non-tumor-bearing donor and cancer patient samples, 50%, or approximately 40 were selected at random for training, while the remainder of the 81 samples were held out for test. Additionally, 3 non-tumor-bearing donors and 4 cancer patients samples were manually held out for final confirmation testing. The neural network architecture used was a supervised learning neural network feedforward architecture using the training functions of Levenberg-Marquardt backpropagation, Bayesian regularization backpropagation, and scaled conjugate gradient backpropagation.

Example 2

MDSC Detection with Recombinant Antibodies

Blood samples were collected from tumor bearing and non-tumor bearing individuals. Each blood sample was processed and prepared for flow cytometry analysis; this includes being stained with recombinant monoclonal antibodies conjugated to different fluorophores. Four panels were used, and the panels included:
Panel 1: Peripheral Blood Mononuclear Cell Staining for MDSC
Panel 2: Peripheral Blood Mononuclear Cell Staining for Lymphocytes
Panel 3: Whole Blood Staining for MDSC for MDSC
Panel 4: Whole Blood Staining for MDSC for Lymphocytes
Prior to analyses by the flow cytometer, the four panels were processed for staining with antibodies. The recombinant monoclonal antibodies used in the staining process for Panel 1 and Panel 3 include: recombinant PE anti-human CD3, recombinant APC-Vio770 anti-human CD14, recombinant PE-Vio770 anti-human CD15 (SSEA-1), recombinant PE-Vio615 anti-human CD16, recombinant VioBright 515 anti-human CD33, recombinant PerCP-Vio700 anti-human HLA-DR, recombinant PE anti-human CD19, recombinant PE anti-human CD56, recombinant APC anti-human LOX-1 (OLR1), and recombinant VioGreen anti-human CD11b. The recombinant monoclonal antibodies used in the staining process for Panel 2 and Panel 4 include: recombinant PE-Vio770 anti-human CD3, recombinant APC anti-human CD19, recombinant VioBright 515 anti-human CD56, recombinant PE anti-human CD4, and recombinant APC-Vio770 anti-human CD8.

Matlab R2017a matrix calculation software was used to perform the calculations on flow cytometer data exports. The Matlab Neural Network Toolbox and Parallel Computing Toolbox were used for network training calculations using the scaled conjugate gradient algorithm.

The events collected by the flow cytometer were grouped into a plurality of bins, each bin representing a sub-population associated with a specific range of measured channel values. A selection of bins was chosen to eliminate the presence of non-useful data in the bins and to improve the neural networks efficiency at learning and classifying patient data. A filter was applied to the selected bins, which were analyzed by the neural network.

Testing Results

In total, 163 blood samples (e.g., biological samples) were obtained from 82 non-tumor-bearing donors (e.g., non-tumor-bearing subjects) and 81 cancer patients (e.g., subjects with cancer). The model was trained using samples from 110 subjects, 55 non-tumor-bearing subjects and 55 cancer patients. Fifty-three of the samples were not used not to train the model, which included 27 non-tumor-bearing donors and 26 cancer patients. For all 163 samples, the model had a specificity of 95.1% and a sensitivity of 88.9% (78/82 non-tumor-bearings correct, 72/81 cancers correct). The 53 samples not used to train the model had a specificity of 88.9% (24/27) and a sensitivity of 88.5% (23/26).

What is claimed is:
1. A computer-implemented method of training an artificial neural network, the method comprising:
(a) performing, by a computer, an analysis process comprising:
(1) obtaining a biological data sample comprising measurements from a flow cytometer instrument of a plurality of event features for a plurality of events of interest in a biological sample;
(2) using four or more flow cytometer measurement channels to define a feature coordinate space, the feature coordinate space comprising four or more axes, each axis corresponding to a different channel of the four or more flow cytometer measurement channels, wherein the four or more flow cytometer measurement channels produces measurements of the plurality of event features contained in the biological data sample;
(3) using the measurements of the plurality of event features for the plurality of events of interest contained in the biological data sample to define locations for the plurality of events of interest in the feature coordinate space to form a distribution in the feature coordinate space indicative of an event population of interest, wherein the distribution in the feature coordinate space indicative of the event population of interest in the biological data sample is formed by:

(i) dividing each axis of the feature coordinate space into a plurality of segments, thereby dividing the feature coordinate space into a plurality of hypervoxels; and (ii) determining counts of a number of events of interest in hypervoxels of the plurality of hypervoxels;

(b) filtering the hypervoxels to select a subset of the plurality of hypervoxels; and (c) applying, by the computer, a training process to an artificial neural network, wherein the training process comprises:

(1) applying, by the computer, an artificial neural network detection structure to the subset of the plurality of hypervoxels, the detection structure employing the artificial neural network to predict, by the computer, a predicted classification of the biological sample; and (2) training the artificial neural network comprising comparing the predicted classification of the biological sample to a known classification of the biological sample.

2. The method of claim 1, wherein filtering comprises discarding hypervoxels populated with at least one of cell fragments and protein debris.

3. The method of claim 1, wherein filtering comprises selecting a subset of hypervoxels containing cell event data.

4. The method of claim 1, wherein filtering comprises reducing the number of hypervoxels by at least 90% as compared to total number of hypervoxels without filtering.

5. The method of claim 1, further comprising applying a dimensionality reduction algorithm to the feature coordinate space.

6. The method of claim 5, wherein the dimensionality reduction algorithm comprises a principal component analysis.

7. The method of claim 6, wherein the principal component analysis comprises identifying at least one axis with variability below a selected threshold and reducing a number of dimensions of the feature coordinate space by discarding the at least one identified axis.

8. The method of claim 1, wherein determining the classification of the biological sample comprises determining whether the biological sample contains cells indicative of the classification of the biological sample.

9. The method of claim 1, wherein the classification of the biological sample comprises a status of a condition of a subject.

10. The method of claim 9, wherein the condition is selected from the group consisting of cancer, diabetes, Parkinson's disease, Alzheimer's disease, pancreatitis, multiple sclerosis, hepatitis, tuberculosis, and HIV.

11. The method of claim 10, wherein the condition is a cancer selected from the group consisting of breast cancer, cervical cancer, ovarian cancer, colorectal cancer, melanoma, sarcoma, endometrial cancer, bladder cancer, renal cancer, gastric cancer, thyroid cancer, malignant lymphoma, lung cancer, prostate cancer, liver cancer, esophageal cancer, thyroid cancer, head and neck cancer, endometrial cancer, and pancreatic cancer.

12. The method of claim 9, wherein the status of the condition comprises a presence of the condition, an absence of the condition, a confirmation of the presence of the condition, a confirmation of the absence of the condition, an increase in severity of the condition, a decrease in severity of the condition, a stage of the condition, a status associated with a prognosis, or a response to a therapy.

13. The method of claim 1, wherein the biological sample is from blood, bone marrow, a solid tumor, or a tissue.

14. The method of claim 1, wherein the plurality of events of interest comprise cells and the plurality of event features are selected from the group consisting of a morphological feature, a cell marker, a protein concentration, a lipid content, an axial light loss, an optical phase, an optical loss, and combinations thereof.

15. The method of claim 14, wherein the cells comprise at least one of myeloid-derived suppressor cells (MDSCs), Natural killer cells, T lymphocytes, and B lymphocytes.

16. The method of claim 15, wherein the cells comprise MDSCs.

17. The method of claim 16, wherein the MDSCs include at least one of polymorphonuclear MDSCs (PMN-MDSCs), monocytic MDSCs (M-MDSCs), early-stage MDSCs (e-MDSCs), and granulocytic MDSCs (g-MDSCs).

18. The method of claim 14, wherein the plurality of event features comprises at least one cell marker selected from the group consisting of CD14, CD15, CD33, and HLA-DR.

19. The method of claim 18 wherein the at least one cell marker comprises CD14, CD15, CD33, and HLA-DR.

20. The method of claim 19, wherein the at least one cell marker further comprises CD45, CD3, CD19, CD56, CD16, and CD11b.

21. The method of claim 14, wherein the plurality of event features comprises at least one cell marker selected from the group consisting of CD3, CD19, and CD56.

22. The method of claim 21, wherein the at least one cell marker comprises CD3, CD19, and CD56.

23. The method of claim 14, wherein the plurality of event features comprises at least one cell marker selected from the group consisting of CD3, CD4, CD8, and CD45.

24. The method of claim 23, wherein the at least one cell marker comprises CD3, CD4, CD8, CD45.

25. The method of claim 1, wherein the detection structure is capable of detecting at least one of a shift, a rotation, or a change in shape in the event population of interest within the feature coordinate space relative to a reference event population within the reference feature coordinate space.

26. The method of claim 1, wherein applying, by the computer, the artificial neural network to the counts of the number of events of interest in the subset of the plurality of hypervoxels comprises identifying, by the computer, characteristic cell features of cells indicative of the condition.

27. A computer-implemented method of using a trained artificial neural network to determine a status of a condition of a subject, the method comprising:

(a) performing, by a computer, an analysis of a biological sample from a subject, the analysis comprising:

(1) obtaining a biological data sample comprising measurements obtained from a flow cytometer instrument of a plurality of event features for a plurality of events of interest from the biological sample;

(2) using four or more flow cytometer measurement channels to define a feature coordinate space, the feature coordinate space comprising four or more axes, each axis corresponding to a different channel of the four or more flow cytometer measurement channels, wherein each of the four or more flow cytometer measurement channels produces measurements of the plurality of event features, and (3) using the measurements of the plurality of event features for the plurality of events of interest from the biological sample to define locations for the plurality of events of interest in the feature coordinate space to form a distribution in the feature coordinate space indicative of an event population of interest, wherein the distribution in the feature coordinate space indicative of the event population of interest is formed by:
- (i) dividing each axis of the feature coordinate space into a plurality of segments, thereby dividing the feature coordinate space into a plurality of hypervoxels;
- (ii) determining counts of a number of events of interest in hypervoxels of the plurality of hypervoxels; and (b) filtering the hypervoxels to select a subset of the plurality of hypervoxels; and (c) applying, by the computer, an artificial neural network to the counts of the number of events of interest in the subset of the plurality of hypervoxels to determine the status of the condition of the subject.

28. The method of claim 27, wherein filtering comprises discarding hypervoxels populated with at least one of cell fragments and protein debris.

29. The method of claim 27, wherein filtering comprises selecting a subset of hypervoxels containing cell event data from the plurality of hypervoxels.

30. The method of claim 27, wherein filtering comprises selecting a subset of the plurality of hypervoxels corresponding to a subset of a plurality of hypervoxels used to train the artificial neural network.

31. The method of claim 27, wherein filtering comprises reducing the number of hypervoxels by at least 90% as compared to a total number of hypervoxels without filtering.

32. The method of claim 27, wherein the condition is selected from the group consisting of cancer, diabetes, Parkinson's disease, Alzheimer's disease, pancreatitis, multiple sclerosis, hepatitis, tuberculosis, and HIV.

33. The method of claim 32, wherein the condition is a cancer selected from the group consisting of breast cancer, cervical cancer, ovarian cancer, colorectal cancer, melanoma, sarcoma, endometrial cancer, bladder cancer, renal cancer, gastric cancer, thyroid cancer, malignant lymphoma, lung cancer, prostate cancer, liver cancer, esophageal cancer, thyroid cancer, head and neck cancer, endometrial cancer, and pancreatic cancer.

34. The method of claim 27, wherein the status of the condition comprises a presence of the condition, an absence of the condition, a confirmation of the presence of the condition, a confirmation of the absence of the condition, an increase in severity of the condition, a decrease in severity of the condition, a stage of the condition, a recurrence of the condition, a status associated with a prognosis, or a response to a therapy.

35. The method of claim 27, wherein the biological sample is from blood, bone marrow, or tissue.

36. The method of claim 27, wherein the plurality of events of interest comprise cells and the plurality of event features are selected from the group consisting of a morphological feature, a cell marker, a protein concentration, a lipid content, an axial light loss, an optical phase, an optical loss, and combinations thereof.

37. The method of claim 36, wherein the cells comprise at least one of myeloid-derived suppressor cells (MDSCs), Natural killer cells, T lymphocytes, and B lymphocytes.

38. The method of claim 37, wherein the cells comprise MDSCs.

39. The method of claim 38, wherein the MDSCs include polymorphonuclear MDSCs (PMN-MDSCs), monocytic MDSCs (M-MDSCs), early-stage MDSCs (e-MDSCs), granulocytic MDSCs (g-MDSCs), and combinations thereof.

40. The method of claim 36, wherein the plurality of event features comprises a cell marker selected from the group consisting of CD14, CD15, CD33, and HLA-DR.

41. The method of claim 40 wherein the at least one cell marker comprises CD14, CD15, CD33, and HLA-DR.

42. The method of claim 41, wherein the at least one cell marker further comprises CD45, CD3, CD19, CD56, CD16, and CD11b.

43. The method of claim 36, wherein the plurality of event features comprises at least one cell marker selected from the group consisting of CD3, CD19, and CD56.

44. The method of claim 43, wherein the at least one cell marker comprises CD3, CD19, and CD56.

45. The method of claim 36, wherein the plurality of event features comprises at least one cell marker selected from the group consisting of CD3, CD4, CD8, and CD45.

46. The method of claim 45, wherein the at least one cell marker comprises CD3, CD4, CD8, CD45.

47. The method of claim 27, wherein the detection structure is capable of detecting at least one of a shift, a rotation, or a change in shape in the event population of interest within the feature coordinate space relative to a reference event population within the reference feature coordinate space.

48. The method of claim 27, wherein applying, by the computer, the artificial neural network to the counts of the number of events of interest in the subset of the plurality of hypervoxels comprises identifying, by the computer, characteristic cell features of cells indicative of the condition.

49. The method of claim 27, wherein the artificial neural network provides a status of the condition for at least three sibling samples from the biological data sample to give a global status category of the biological data sample, wherein the global status category comprises the most probable category.

* * * * *